US010689687B2

(12) United States Patent
Nolan et al.

(10) Patent No.: US 10,689,687 B2
(45) Date of Patent: *Jun. 23, 2020

(54) DETECTION OF TARGET NUCLEIC ACIDS IN A CELLULAR SAMPLE

(71) Applicant: The Board of Trustees of the Leland Stanford Junior University, Stanford, CA (US)

(72) Inventors: Garry P. Nolan, Redwood City, CA (US); Yury Goltsev, Stanford, CA (US); Quan Nguyen, San Ramon, CA (US); Yunqing Ma, San Jose, CA (US); Chunfai Lai, Fremont, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 129 days.

This patent is subject to a terminal disclaimer.

(21) Appl. No.: 15/691,580

(22) Filed: Aug. 30, 2017

(65) Prior Publication Data

US 2017/0362642 A1  Dec. 21, 2017

Related U.S. Application Data

(63) Continuation of application No. 14/045,698, filed on Oct. 3, 2013, now Pat. No. 9,783,841.

(60) Provisional application No. 61/709,896, filed on Oct. 4, 2012.

(51) Int. Cl.
| *C12Q 1/68* | (2018.01) |
| *C07H 21/00* | (2006.01) |
| *C12Q 1/6813* | (2018.01) |
| *C12Q 1/6841* | (2018.01) |

(52) U.S. Cl.
CPC ......... *C12Q 1/6813* (2013.01); *C12Q 1/6841* (2013.01)

(58) Field of Classification Search
CPC .................................. C12Q 1/68; C07H 21/00
See application file for complete search history.

(56) References Cited

U.S. PATENT DOCUMENTS

| 4,868,105 | A | 9/1989 | Urdea et al. |
| 4,888,278 | A | 12/1989 | Singer et al. |
| 5,021,335 | A | 6/1991 | Tecott et al. |
| 5,093,232 | A | 3/1992 | Urdea et al. |
| 5,124,246 | A | 6/1992 | Urdea et al. |
| 5,196,182 | A | 3/1993 | Ryan |
| 5,635,352 | A | 6/1997 | Urdea et al. |
| 5,681,697 | A | 10/1997 | Urdea et al. |
| 5,681,702 | A | 10/1997 | Collins et al. |
| 5,712,383 | A | 1/1998 | Sheridan et al. |
| 5,747,244 | A | 5/1998 | Sheridan et al. |
| 5,780,227 | A | 7/1998 | Sheridan et al. |
| 5,849,481 | A | 12/1998 | Urdea et al. |
| 5,888,733 | A * | 3/1999 | Hyldig-Nielsen ... C12O 1/6841 435/6.11 |
| 6,096,716 | A | 8/2000 | Hayes et al. |
| 6,232,462 | B1 | 5/2001 | Collins et al. |
| 6,232,465 | B1 | 5/2001 | Hiatt et al. |
| 7,033,758 | B2 | 4/2006 | Kenny et al. |
| 7,709,198 | B2 | 5/2010 | Luo et al. |
| 7,803,541 | B2 | 9/2010 | Luo et al. |
| 7,927,798 | B2 | 4/2011 | Zheng et al. |
| 8,017,360 | B2 | 9/2011 | Luo et al. |
| 8,063,196 | B2 | 11/2011 | Zheng et al. |
| 8,114,681 | B2 | 2/2012 | Martin et al. |
| 8,628,918 | B2 | 1/2014 | Luo et al. |
| 8,632,970 | B2 | 1/2014 | Luo et al. |
| 9,783,841 | B2 * | 10/2017 | Nolan ................... C12Q 1/6841 |
| 10,295,540 | B1 * | 5/2019 | Buturovic ............ G01N 33/574 |
| 2001/0008760 | A1 * | 7/2001 | King ................ G01N 33/56983 435/5 |
| 2001/0026916 | A1 * | 10/2001 | Ginsberg ............. C12Q 1/6883 435/6.16 |
| 2002/0045196 | A1 * | 4/2002 | Mahoney ............. C12N 5/0605 435/7.21 |
| 2002/0094577 | A1 * | 7/2002 | Guirguis .................. G01N 1/30 436/18 |
| 2002/0102584 | A1 | 8/2002 | Hester et al. |
| 2002/0137035 | A1 | 9/2002 | Stender et al. |
| 2002/0172950 | A1 | 11/2002 | Kenny et al. |
| 2003/0017444 | A1 * | 1/2003 | Levine ..................... A01N 1/02 435/2 |
| 2003/0186237 | A1 | 10/2003 | Ginsberg et al. |
| 2004/0101519 | A1 | 5/2004 | June et al. |
| 2004/0115697 | A1 | 6/2004 | Doxsey et al. |
| 2004/0234970 | A1 | 11/2004 | Yoo |

(Continued)

FOREIGN PATENT DOCUMENTS

WO  WO 2010/097655 A1  9/2010
WO  WO2012/162779  * 12/2012

OTHER PUBLICATIONS

Balis et al. Experimental Lung Research 6 (3-4) : 197-213 (Year: 1984).*
Fei et al., Anatomic localization of alternatively spliced leptin receptors (Ob-R) in mouse brain and other tissues. PNAS 94 : 7001-7005 (Year: 1997).*
Liu et al., Microfluidic fluorescence in situ hybridization and flow cytometry (microFlow -FISH) Lab on a Chip 11 : 2673 (Year: 2011).*
Pena et al, .miRNA in situ hybridization in formaldehyde and EDC-fixed tissues. Nature Methods 6(2) : 139 (Year: 2009).*
Santra et al., Blood 101(6) :2374-2376 (Year: 2003).*

(Continued)

*Primary Examiner* — Ethan C Whisenant
(74) *Attorney, Agent, or Firm* — Kyle A. Gurley; Bret E. Field; Bozicevic, Field & Francis LLP

(57) ABSTRACT

Methods of assaying cells of a cellular sample for the presence of a target nucleic acid are provided. Aspects of the methods include evaluating a cellular sample that has been contacted with a nuclease inhibitor for the presence of a target nucleic acid. Also provided are devices and kits that find use in practicing the methods described herein.

47 Claims, 29 Drawing Sheets

(56) References Cited

U.S. PATENT DOCUMENTS

| | | | |
|---|---|---|---|
| 2005/0272114 A1 | 12/2005 | Darzins et al. | |
| 2007/0020735 A1 | 1/2007 | Chen et al. | |
| 2007/0065825 A1* | 3/2007 | Stordeur | A61B 5/411 435/6.12 |
| 2007/0111960 A1 | 5/2007 | Stender et al. | |
| 2007/0299030 A1* | 12/2007 | Dmitrovsky | C12N 15/111 514/44 A |
| 2008/0038725 A1 | 2/2008 | Luo et al. | |
| 2008/0050746 A1 | 2/2008 | McMaster et al. | |
| 2008/0176242 A1 | 7/2008 | McMaster et al. | |
| 2009/0081688 A1 | 3/2009 | Luo et al. | |
| 2009/0220933 A1 | 9/2009 | Kolvraa et al. | |
| 2009/0239755 A1 | 9/2009 | Thastrup et al. | |
| 2009/0286753 A1* | 11/2009 | Kauppinen | C12N 15/111 514/44 R |
| 2009/0298709 A1 | 12/2009 | Ma | |
| 2010/0099074 A1 | 4/2010 | Nolan et al. | |
| 2010/0209397 A1 | 8/2010 | Maor | |
| 2010/0233706 A1* | 9/2010 | Tuschl | C12Q 1/6806 435/6.1 |
| 2010/0260718 A1 | 10/2010 | Ren | |
| 2011/0059861 A1 | 3/2011 | Nolan et al. | |
| 2011/0130347 A1* | 6/2011 | Golz | C07K 14/723 514/21.2 |
| 2011/0303880 A1 | 12/2011 | Mulik et al. | |
| 2012/0003648 A1 | 1/2012 | Ma et al. | |
| 2012/0004132 A1 | 1/2012 | Zhang et al. | |
| 2012/0052498 A1 | 3/2012 | Nguyen et al. | |
| 2012/0172246 A1 | 7/2012 | Nguyen et al. | |
| 2012/0178081 A1 | 7/2012 | Nguyen et al. | |
| 2012/0244209 A1* | 9/2012 | Roth | A61K 48/005 424/450 |
| 2014/0011694 A1 | 1/2014 | Couronne et al. | |
| 2014/0134650 A1 | 5/2014 | Hawtin et al. | |
| 2014/0349964 A1 | 11/2014 | Shiota et al. | |
| 2015/0018226 A1* | 1/2015 | Hansen | G01N 33/5005 506/9 |

OTHER PUBLICATIONS

Volpi et al., FISH glossary: an overview of the fluorescence in situ hybridization technique. Biotechniques 45(4) : 385-409 (Year: 2008).*
Wu et al., Microfluidically-unified cell culture, sample preparation, imaging and flow cytometry for measurement of cell signaling pathways with single cell resolution. Lab on a Chip 11 : 2823-2831 (Year: 2012).*
Naresh et al., J. of Clinical Pathology 59 : 903-911 (Year: 2006).*
Pena et al., Mature Methods 6(2) :139-141 with Supplementary Methods attached pp. 1-11 (Year: 2009).*
Bauman et al. "Flow cytometric detection of ribosomal RNA in suspended cells by fluorescent in situ hybridization," Cytometry 9: 517 (1988).
Bayer et al. "Flow cytometric detection of beta-globin mRNA in murine haemopoietic tissues using fluorescent in situ hybridization," Cytometry (1990), 11(1):132-143.
Bodenmiller et al. "Multiplexed mass cytometry profiling of cellular states perturbed by small-molecule regulators," Nature Biotechnology 30 (9) : 858 (Sep. 2012).
Bushnell et al. "ProbeDesigner: for the design of probesets for branched DNA (bDNA) signal amplification assays," Bioinformatics (1999), 15:348-355.
Cao et al. "Identification of malignant cells in multiple myeloma bone marrow with immunoglobulin VH gene probes by fluorescent in situ hybridization and flow cytometry," J. of Climnical Investigations 95 : 964 (1995).
Collins et al. "Branched DNA (bDNA) Technology for Direct Quantification of Nucleic Acids: Design and Performance," Gene Quantification (1998), 205-223.
Corporeau et al. "In situ hybridisation for flow cytometry: a molecular method for monitoring stress-gene expression in hemolymph cells of oysters," Aquat Toxicol (Sep. 2003), 64(4):427-435.

Flagella et al. "A multiplex branched DNA assay for parallel quantitative gene expression profiling," Anal Biochem (May 2006), 352(1):50-60.
Friedrich et al. "Improved enumeration of lactic acid bacteria in mesophilic dairy starter cultures by using multiplex quantitative real-time PCR and flow cytometry-fluorescence in situ hybridization," Appl Environ Microbiol (Jun. 2006), 72(6):4163-4171.
Harper et al. "In situ /Hybridization—Application to Gene Localization and RNA Detection," Cancer Genetics Cytogenetics 19 : 73 (1986).
Hoggar et al. "Localization of Leptin Receptor mRNA Splice Variantsin Murine Peripheral Tissues by RT-PCR and in Situ Hybridization," BBRC 232 :383 (1997).
Hsu et al. "Use of avidin-biotin-peroxidase complex (ABC) in immunoperoxidase techniques: a comparison between ABC and unlabeled antibody (PAP) procedures," The J. of Histochemistry and Cytochremistry 29:577 (1981).
Huang et al. "Uptake of FITC-Chitosan Nanoparticles by A549 Cells," Pharmaceutical Research 19(10) : 1488 (2002).
Jen et al. "Flow-FISH analysis and isolation of clostridial strains in an anaerobic semi-solid bio-hydrogen producing system by hydrogenase gene target," Appl Microbiol Biotechnol (Apr. 2007), 74(5):1126-1134.
Jonsson et al. Histochemie, Bd.1 S. 251-256 (1959).
Kenny et al. "Detection of viral infection and gene expression in clinical tissue specimens using branched DNA (bDNA) in situ hybridization," J Histochem Cytochem (Sep. 2002), 50(9):1219-1227.
Kottaridi et al. "Clinical performance of human papillomavirus E6, E7 mRNA flow cytometric assay compared to human papillomavirus DNA typing," Anal Quant Cytol Histol (Dec. 2011), 33(6):305-310.
Lou et al. "Polymer-Based Elemental Tags for Sensitive Bioassays," Angew. Chem. Int. Ed. 46: 6111 (2007).
Matthiesen et al. "Fast and Non-Toxic in Situ Hybridization without Blocking of Repetitive Sequences," PLoS One 7 (7) : e40675 (2012).
Mosiman et al. "In situ hybridization in flow cytometry," Methods Mol Med (2001), 55:231-253.
Mosiman et al. "Reducing cellular autofluorescence in flow cytometry: an in situ method," Cytometry (Jun. 1995), 30(3):151-156.
Mota et al. "Identification of nitrite-reducing bacteria using sequential mRNA fluorescence in situ hybridization and fluorescence-assisted cell sorting," Microb Ecol (Jul. 2012), 64(1):256-267.
Narimatsu et al. "High-throughput cervical cancer screening using intracellular human papillomavirus E6 and E7 mRNA quantification by flow cytometry," Am J Clin Pathol (May 2005), 123(5):716-723.
Nolte et al. "Branched DNA signal amplification for direct quantitation of nucleic acid sequences in clinical specimens," Adv Clin Chem (1988), 33:201-235.
Ornatsky et al. "Messenger RNA Detection in Leukemia Cell lines by Novel Metal-Tagged in situ Hybridization using Inductively Coupled," Plasma Mass Spectrometry. Translational Oncogenomics 1 :1-9 (2006).
Patterson et al. "Detection of HIV-1 DNA and messenger RNA in individual cells by PCR-driven in situ hybridization and flow cytometry," Science (May 1993), 260(5110):976-979.
Patterson et al. "Detection of HIV-1 DNA and Messenger RNA in Individual Cells by PCR-Driven in Situ Hybridization and Flow Cytometry," Science 260 : 976 (1993).
Patterson et al. "Detection of HIV-RNA-positive monocytes in peripheral blood of HIV-positive patients by simultaneous flow cytometric analysis of intracellular HIV RNA and cellular immunophenotype," Cytometry (Apr. 1998), 31(4):265-274.
Pena et al. "miRNA in situ hybridization in formaldehyde and EDC-fixed tissues," Nature Methods 6(2) : 139 (2009).
Perez De Hornedo et al. "Flow cytometric analysis of the in situ hybridization of cyclooxygenase isoforms in mesangial cells treated with cyclosporine A," Cytometry A (Mar. 2006), 69(3):161-164.
Player et al. "Single-copy Gene Detection Using Branched DNA (bDNA) in Situ Hybridization," J Histochem Cytochem (May 2001), 49(5):603-612.

(56) References Cited

OTHER PUBLICATIONS

Player et al. "Single-copy Gene Detection Using Branched DNA (bDNA) in Situ Hybridization," Journal of Histochemistry & Cytochemistry 49 (5) : 603 (2001).
QuantiGene.RTM. (2007) "2.0 Reagent System" User Manual, 32 pages.
QuantiGene.RTM. (2011) "ViewRNA ISH Cell Assay" User Manual, 72 pages.
Ravichandran et al. "Immunoglobulin VH usage analysis by fluorescent in situ hybridization and flow cytometry," J. of Immunological Methods 153:249 (1992).
Robertson et al. "LNA flow-FISH: a flow cytometry-fluorescence in situ hybridization method to detect messenger RNA using locked nucleic acid probes," Anal Biochem (Jul. 2009), 390(2):109-114.
Robertson et al. "Locked Nucleic Acid Flow Cytometry-fluorescence in situ Hybridization (LNA flow-FISH): a Method for Bacterial Small RNA Detection," J Vis Exp (Jan. 2012), (59):3655.
Robertson et al. "Monitoring viral RNA in infected cells with LNA flow-Fish," RNA (Aug. 2010),16(8):1679-1685.
Shivers et al. "Combination of Immunochemistry and In Situ Hybridization in the Same Tissue Section of Rat Pituitary," The J. of Histochemistry and Cytochemistry 34(1) :39-43 (1986).
Summersgill et al. "Fluorescence and chromogenic in situ hybridization to detect genetic aberrations in formalin-fixed paraffin embedded material, including tissue microarrays," Nature Protocols 3 (2) : 220 (2008).
The Stratagene Catalog p. 39 (1988).
Timm et al. "Fluorescent in situ hybridization en suspension (FISHES) using digoxigenin-labeled probes and flow cytometry," Biotechniques (Mar. 1992), 12(3):362-367.
Tkachuk et al. "Detection of bcr-abl Fusion in Chronic Myelogeneous Leukemia by in Situ Hybridization," Science 250 :4980 (1990).
Van Cleve et al. "Direct quantitation of HIV by flow cytometry using branched DNA signal amplification," Mol Cell Probes (Aug. 1998), 12(4):243-247.
Van Tine et al. "Simultaneous in Situ Detection of RNA, DNA, and Protein Using Tyramide-Coupled Immunofluorescence," Methods in Molecular Biology 292 :215 (2005). Edited by Paul M. Lieberman.
Viertler et al. "A New Technology for Stabilization of Biomolecules in Tissues for Combined Histological and Molecular Analyses," J. of Molecular Diagnostics 14 (5) :458 (2012).
Wallner et al. Optimizing Fluorescent In Situ Hybridization With rRNA-Targeted Oligonucleotide Probes for Flow Cytometric Identification of Microorganisms Cytometry 14 :136 (1993).
Wang et al. "Regulation of insulin preRNA splicing by glucose," PNAS USA (Apr. 1997), 94(9):4360-4365.
Weber et al. "Chromosome-wide and promoter-specific analyses identify sites of differential DNA methylation in normal and transformed human cells," Nature Genetics 37 (8) : 853 (2005).
Wilbur et al. "Quantification of HCV RNA in clinical specimens by branched DNA (bDNA) technology," Methods Mol Med (1999), 19:71-78.
Wilkinson et al. "Detection of Messenger RNA by in Situ Hybridization to Tissue Sections and Whole Mounts," Methods in Enzymology 225 :361 (1993).
Yamada et al. "Messenger RNA quantification after fluorescence-activated cell sorting using in situ hybridization," Cytometry A (Nov. 2010), 77(11):1032-1037.
Yamada et al. "Prolonged hybridization with a cRNA probe improves the signal to noise ratio for in-tube in situ hybridization for quantification of mRNA after fluorescence-activated cell sorting," Biotech Histochem (Jul. 2012), 87(5):366-371.
Zaidi et al. "Dual Fluorescent in Situ Hybridization and Immunohistochemical Detection with Tyramide Signal Amplification," J. of Histochemistry & Cytochemistry 48(10) : 1369 (2000).
Zhang et al. "Small Interfering RNA and Gene Expression Analysis Using a Multiplex Branched DNA Assay without RNA Purification," J Biomol Screen (Sep. 2005), 10(6):549-556.

\* cited by examiner

A

B

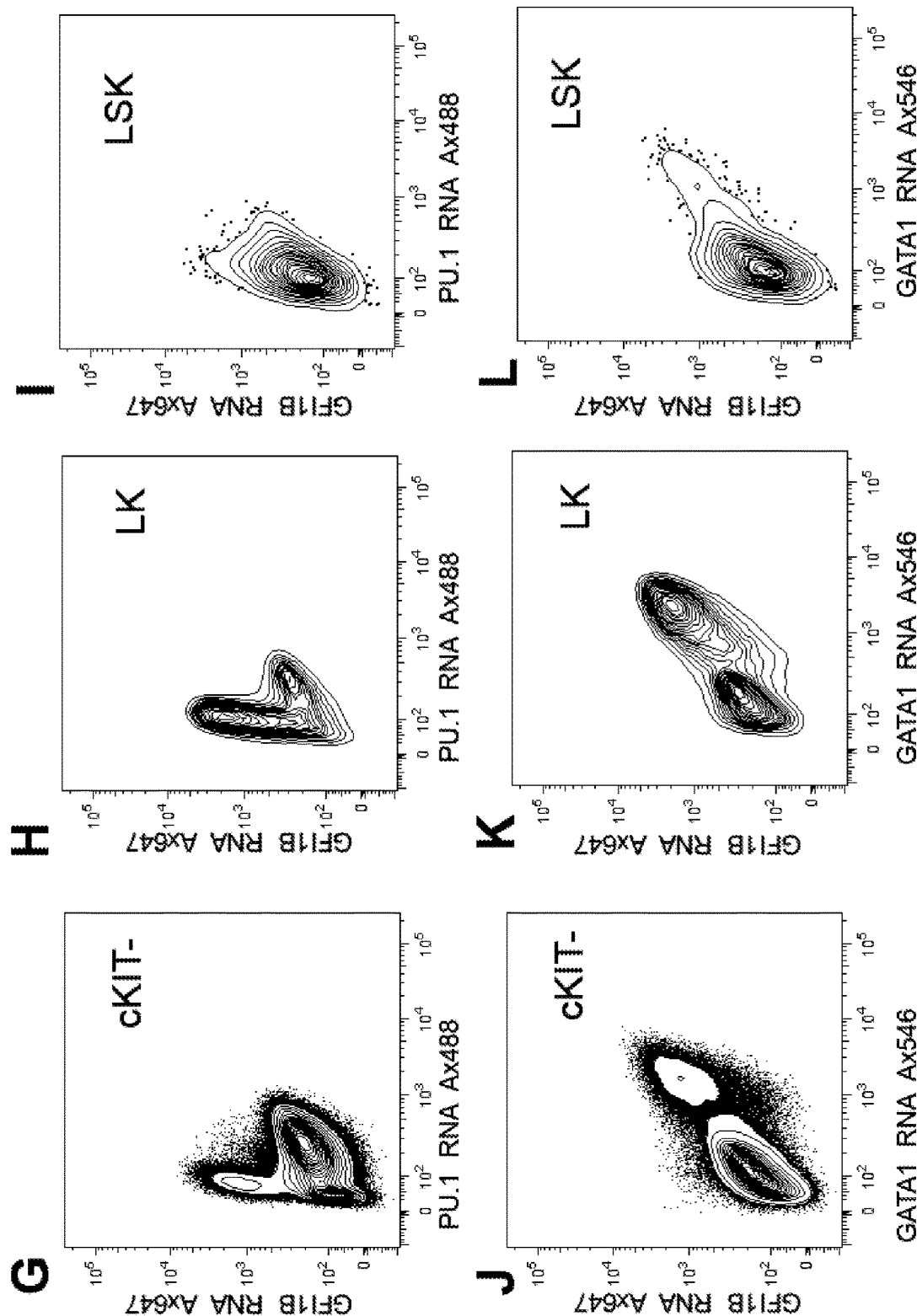

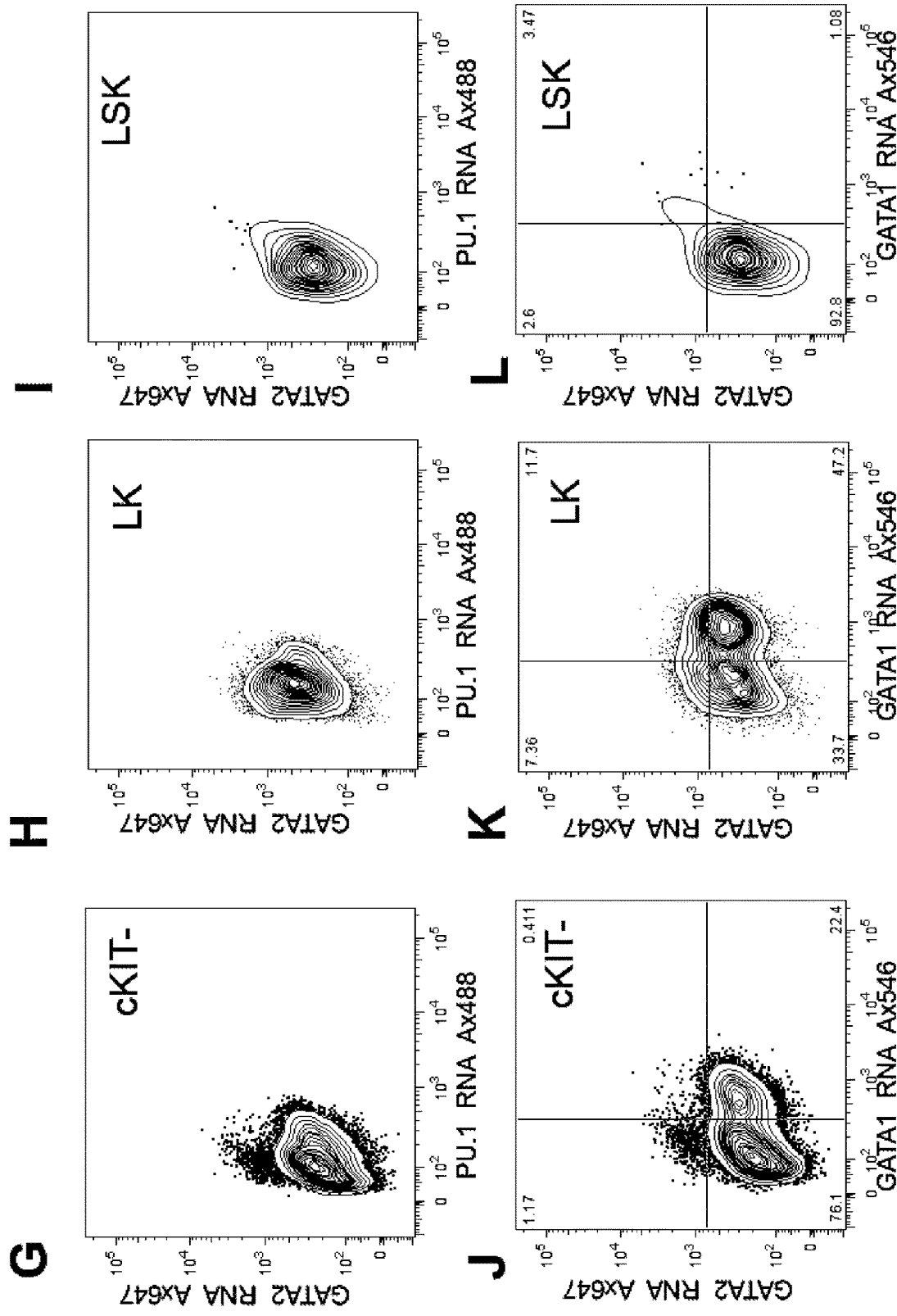

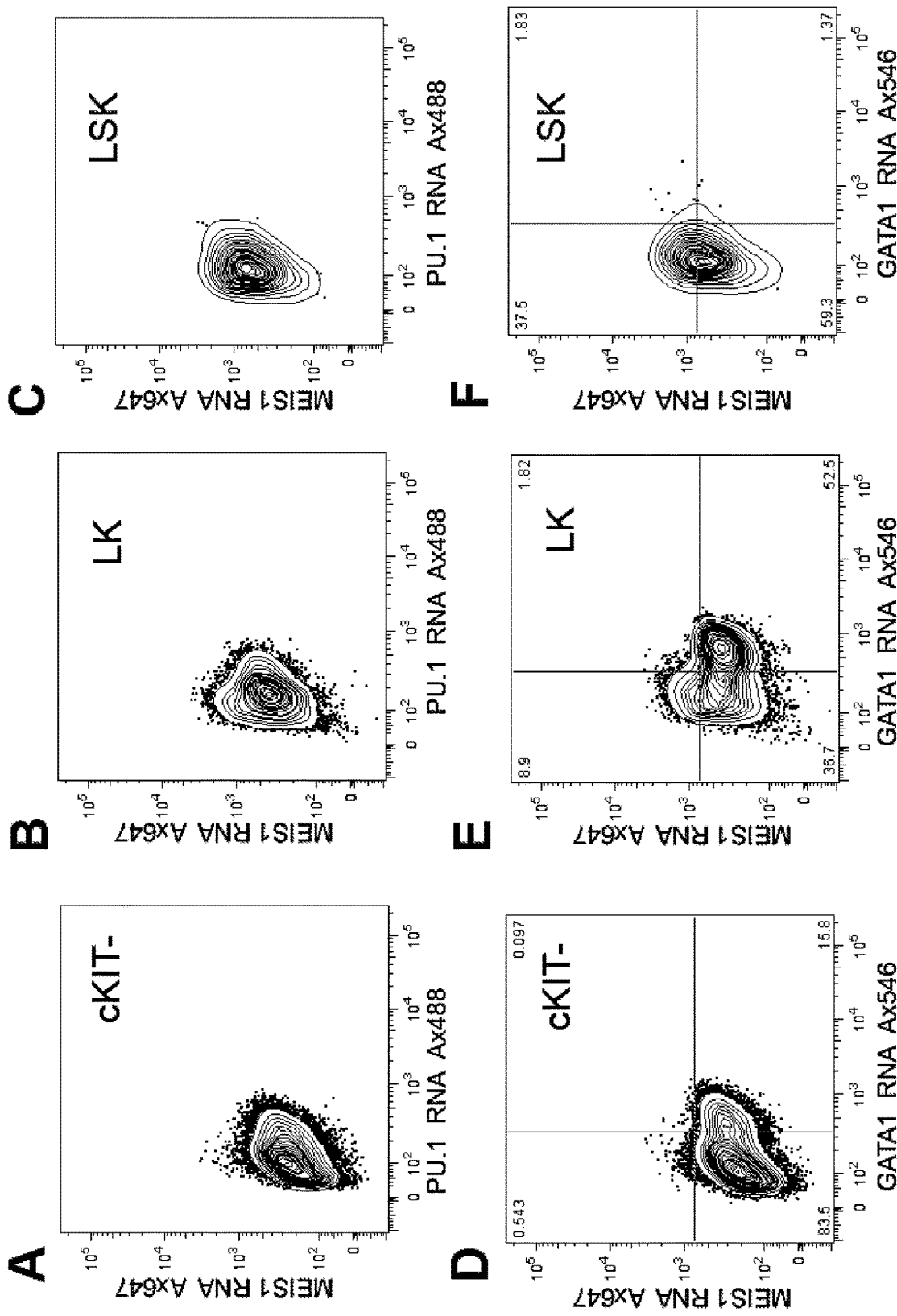

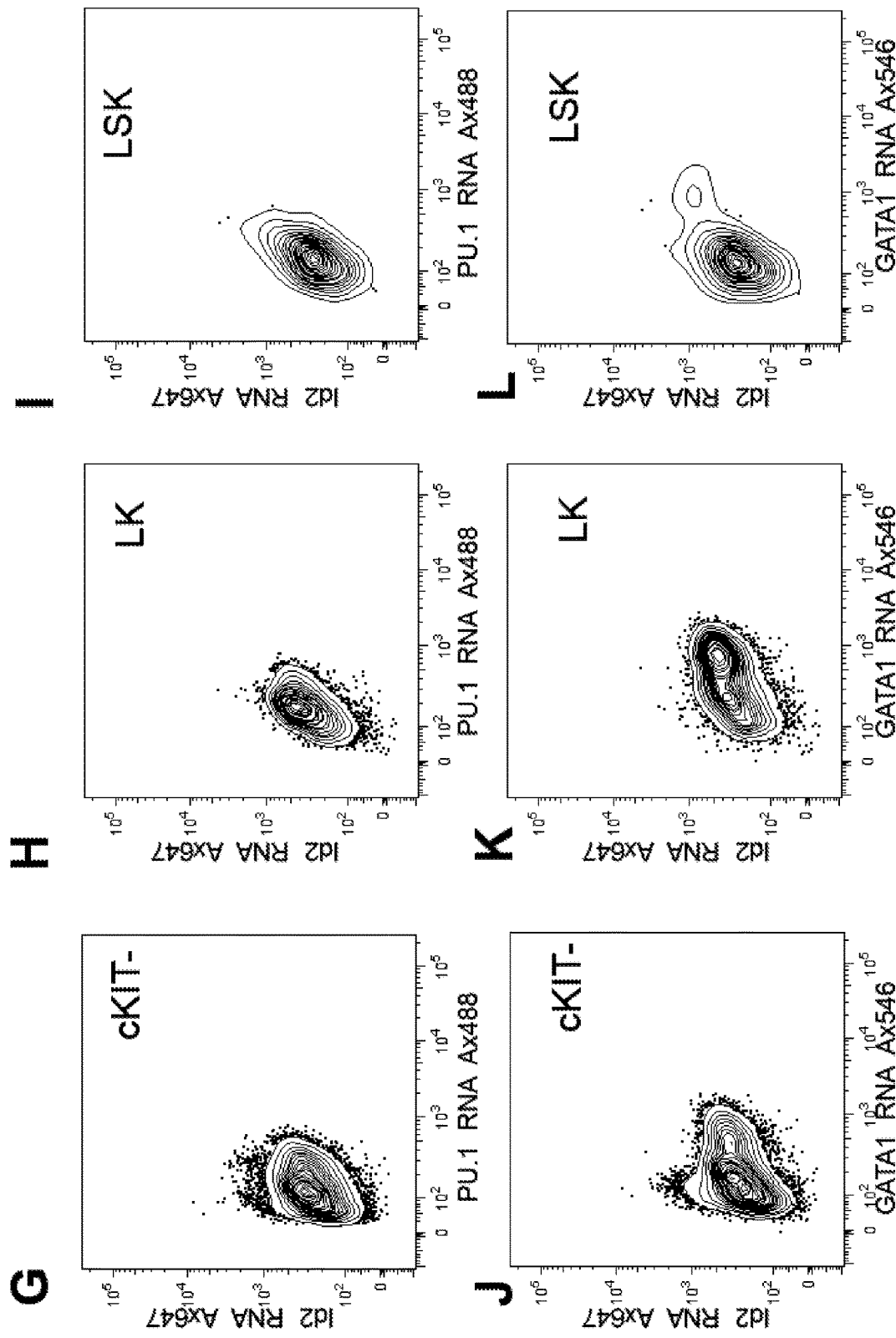

FIGURE 15 A
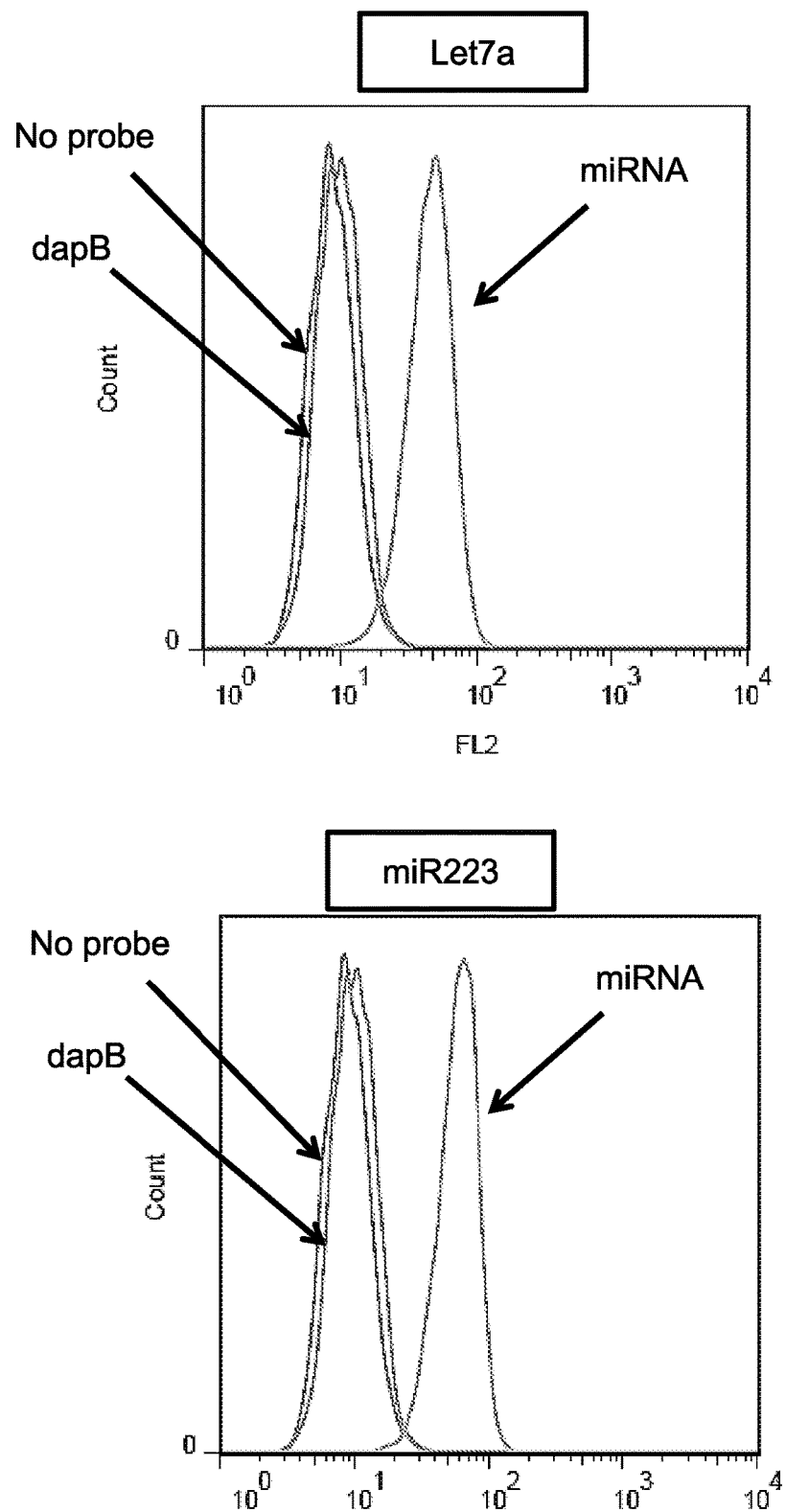
Notes:
zz design for branched nucleic acid probe (see Figure 14)
45 min Fast Red incubation Notes:
zz design for branched nucleic acid probe (see Figure 14)
45 min Fast Red incubation Notes:
zz design for branched nucleic acid probe
45 min Fast Red incubation

DETECTION OF TARGET NUCLEIC ACIDS IN A CELLULAR SAMPLE

CROSS-REFERENCE

This application is a continuation of U.S. patent application Ser. No. 14/045,698 filed on Oct. 3, 2013, which application claims the benefit of U.S. Provisional Patent Application No. 61/709,896 filed on Oct. 4, 2012; which applications are incorporated herein by reference in their entirety.

GOVERNMENT RIGHTS

This invention was made with Government support under contract CA034233 awarded by the National Institutes of Health. The Government has certain rights in the invention.

INTRODUCTION

Many disease conditions result from the aberrant behavior of individual cells, and such behavior is fundamentally the result of abnormal molecules and/or aberrant molecular interactions. Molecular markers of disease therefore provide a foothold toward understanding the molecular causes of aberrant cell behavior and facilitate the identification, quantification, and/or isolation of the aberrant cells. As such, molecular markers are an invaluable tool aiding in the early diagnosis of cancer and other debilitating conditions.

Flow cytometry, or fluorescent activated cell sorting (FACS), has enabled the rapid analysis of molecular markers in individual cells of a cell sample. In flow cytometry, cells of a cellular sample are suspended in a stream of fluid, which is passed, one cell at a time, by at least one beam of light (e.g., a laser light of a single wavelength). A number of detectors, including one or more fluorescence detectors, detect scattered light as well as light emitted from the cellular sample (e.g., fluorescence). In this way, the flow cytometer acquires data that can be used to derive information about the physical and chemical structure of each individual cell that passes through the beam(s) of light.

RNA has long been recognized as a critical class of molecular marker. Expression levels of specific RNAs are known to vary according to cell type, metabolic state, state of differentiation, state of activation or stimulation, etc. The advent of techniques for the assessment of RNA expression levels for thousands of RNAs in parallel has led to the discovery that the expression levels of many RNAs associate with various metabolic states, states of differentiation, states of stimulation, and/or disease states. Examples of such RNAs include SIRT1 (energy expenditure and insulin sensitivity), CCL3 (inflammatory response), BACE1 and PP2A (Alzheimer's disease), KIF14 (lung cancer), and MDR1 (chemotherapeutic response of primary breast tumors). Therefore, the evaluation of RNA expression in individual cells can be useful in diagnosis as well as prognosis.

SUMMARY

Methods of assaying cells of a cellular sample for the presence of a target nucleic acid are provided. Aspects of the methods include evaluating a cellular sample that has been contacted with a nuclease inhibitor for the presence of a target nucleic acid. Also provided are devices and kits that find use in practicing the methods described herein.

BRIEF DESCRIPTION OF THE FIGURES

In FIGS. 3G-I, IFNα and IRF7 RNA levels were measured by SCRF in pDCs from bone marrow activated for 11 hours in the presence of CpG.

DETAILED DESCRIPTION

Figure 1:
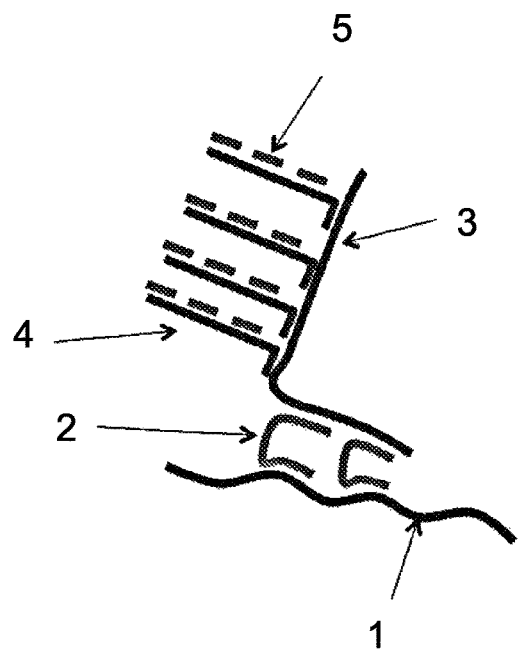
FIG. 1 illustrates a branched DNA amplification protocol according to an embodiment of the invention, which enables a broad range of cytometric RNA detection. (A) Schematic diagram depicting of one embodiment of the hybridization and amplification steps to detect a target nucleic acid. B. Genes expressed at a range of levels (GAPDH, PPIB, HPRT, POLR2A, HMBS) were detected by SCRF in U937 cells. C. SCRF had linear performance in a broad dynamic range of concentration. Plotted on the Y-axis are the average number of molecules/fluorescent signals per cells (calculated from microscopy images) and on the X-axis relative MFI ($MFI_{gene}/MFI_{no\ probe}$) D. Cells analyzed in B were examined by fluorescence microscopy. Blue indicates nuclear stain (DAPI). Green corresponds to signal from branched DNA amplification of individual transcripts.
Figure 1:
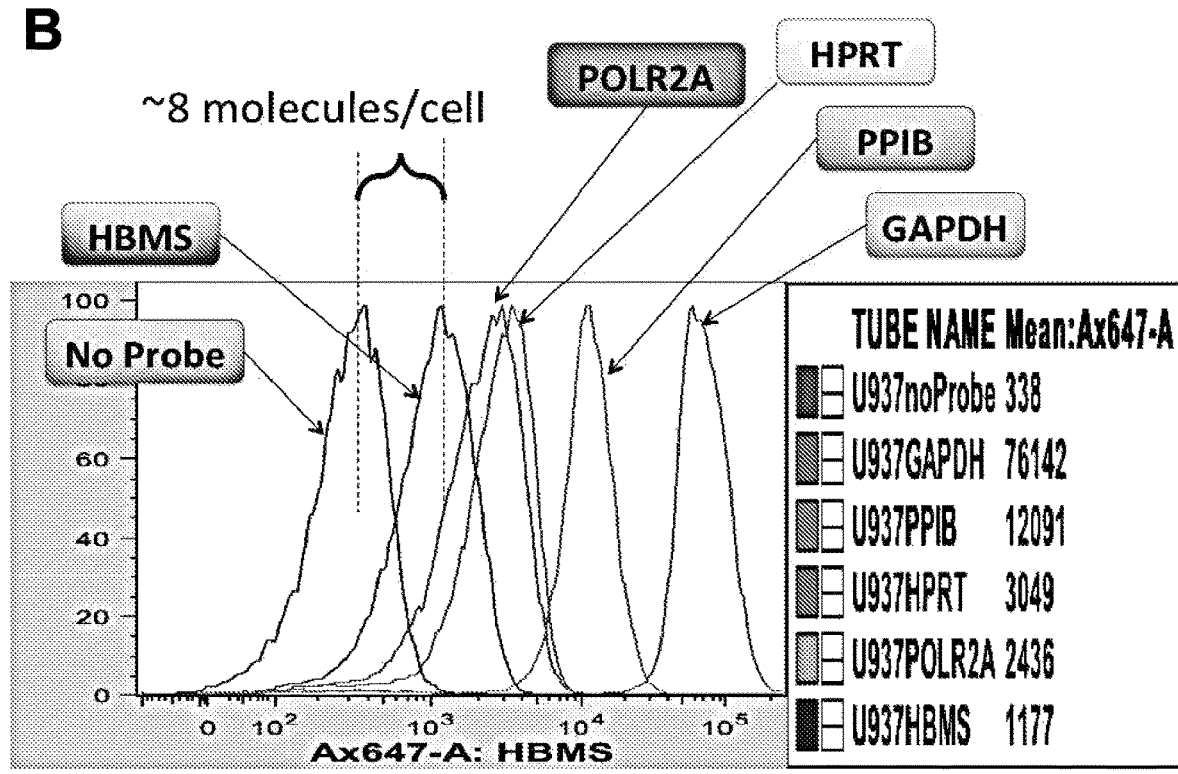
Figure 1:
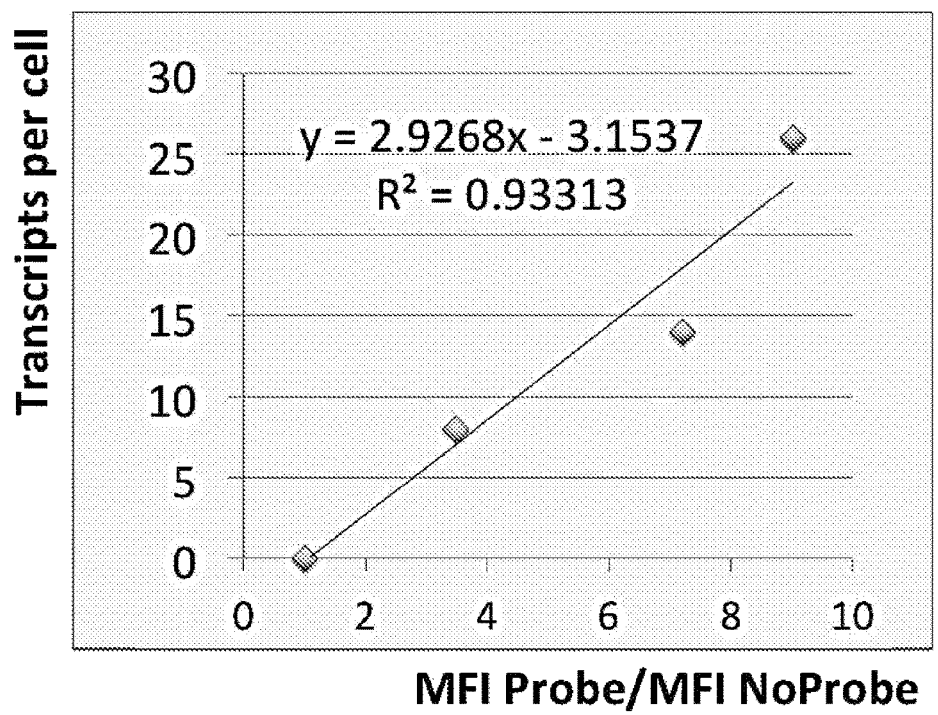
Figure 1:
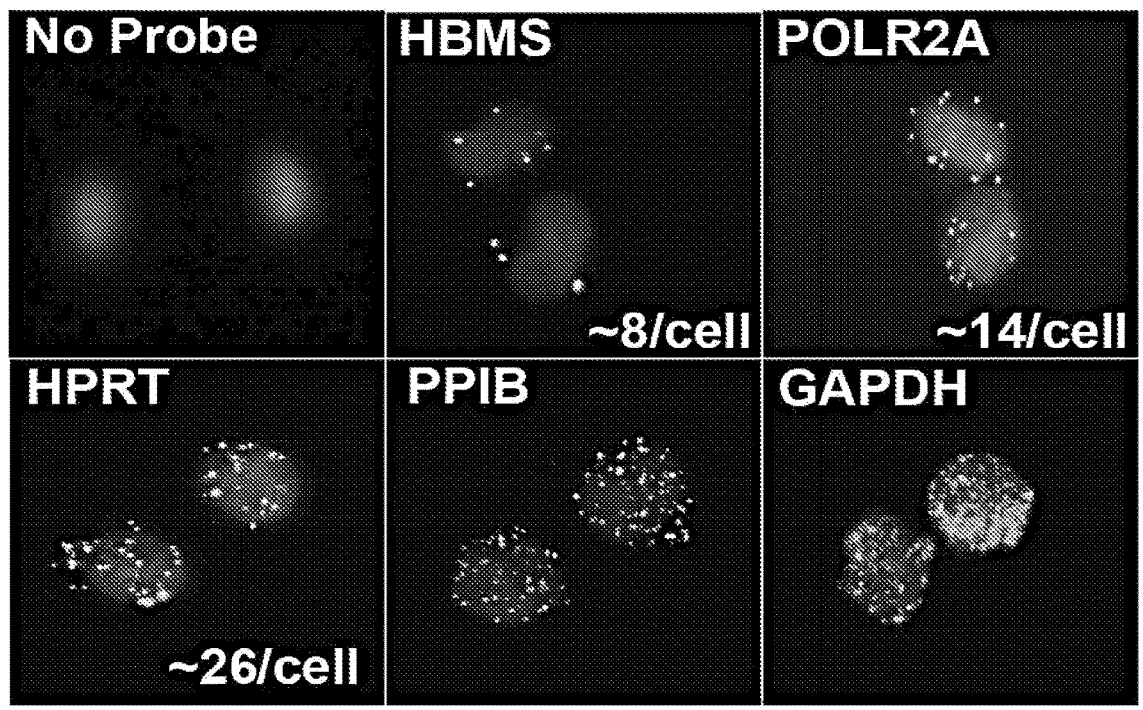

Methods of assaying cells of a cellular sample for the presence of a target nucleic acid are provided. Aspects of the methods include evaluating a cellular sample that has been contacted with a nuclease inhibitor for the presence of a target nucleic acid. Also provided are devices and kits that find use in practicing the methods described herein.

Before the present invention is described in greater detail, it is to be understood that this invention is not limited to particular embodiments described, as such may, of course, vary. The invention encompasses various alternatives, modifications, and equivalents, as will be appreciated by those of skill in the art. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

Any publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Methods

Aspects of the invention include methods of assaying a cellular sample for the presence of a target nucleic acid (e.g., deoxyribonucleic acid, ribonucleic acid). As such, methods of the invention are methods of evaluating the amount (i.e., level) of a target nucleic acid in a cell of a cellular sample. In some embodiments, methods of the invention are methods of evaluating whether a target nucleic acid is present in a sample, where the detection of the target nucleic acid is qualitative. In some embodiments, methods of the invention are methods of evaluating whether a target nucleic acid is present in a sample, where the detection of the target nucleic acid is quantitative. The methods can include determining a quantitative measure of the amount of a target nucleic acid in a cell of a cellular sample. In some embodiments, quantifying the level of expression of a target nucleic acid includes comparing the level of expression of one nucleic acid to the level of expression of another nucleic acid in order to determine a relative level of expression. In some embodiments, the methods include determining whether a target nucleic acid is present above or below a predetermined threshold in a cell of a cellular sample. As such, when the detected signal is greater than a particular threshold (also referred to as a "predetermined threshold"), the amount of target nucleic acid of interest is present above the predetermined threshold in the cell of a cellular sample. When the detected signal is weaker than a predetermined threshold, the amount of target nucleic acid of interest is present below the predetermined threshold in the cell of a cellular sample.

The term "cellular sample," as used herein means any sample containing one or more individual cells in suspension at any desired concentration. For example, the cellular sample can contain $10^{11}$ or less, $10^{10}$ or less, $10^9$ or less, $10^8$ or less, $10^7$ or less, $10^6$ or less, $10^5$ or less, $10^4$ or less, $10^3$ or less, 500 or less, 100 or less, 10 or less, or one cell per milliliter. The sample can contain a known number of cells or an unknown number of cells. Suitable cells include eukaryotic cells (e.g., mammalian cells) and/or prokaryotic cells (e.g., bacterial cells or archaeal cells).

In practicing the methods of the invention, the cellular sample can be obtained from an in vitro source (e.g., a suspension of cells from laboratory cells grown in culture) or from and in vivo source (e.g., a mammalian subject, a human subject, etc.). In some embodiments, the cellular sample is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the sample is obtained from an in vivo source and can include samples obtained from tissues (e.g., cell suspension from a tissue biopsy, cell suspension from a tissue sample, etc.) and/or body fluids (e.g., whole blood, fractionated blood, plasma, serum, saliva, lymphatic fluid, interstitial fluid, etc.). In some cases, cells, fluids, or tissues derived from a subject are cultured, stored, or manipulated prior to evaluation. In vivo sources include living multi-cellular organisms and can yield non-diagnostic or diagnostic cellular samples.

Cellular samples can be obtained from a variety of different types of subjects. In some embodiments, a sample is from a subject within the class mammalia, including e.g., the orders carnivore (e.g., dogs and cats), rodentia (e.g., mice, guinea pigs, and rats), lagomorpha (e.g. rabbits) and primates (e.g., humans, chimpanzees, and monkeys), and the like. In certain embodiments, the animals or hosts, i.e., subjects (also referred to herein as patients) are humans.

A target nucleic acid can be any polynucleotide nucleic acid molecule (e.g., DNA molecule; RNA molecule, modified nucleic acid, etc.). In some embodiments, the target nucleic acid is a coding RNA (e.g., mRNA). In some embodiments, the target nucleic acid is a non-coding RNA (e.g., tRNA, rRNA, microRNA (miRNA), mature miRNA, immature miRNA; etc). In some embodiments, the target nucleic acid is an RNA molecule that is not normally spliced (e.g., mRNA, rRNA, etc.) in the context of a cell. In some embodiments, the target nucleic acid is an RNA molecule that is normally spliced (e.g., mRNA, rRNA, etc.) in the context of a cell. A suitable target nucleic acid can therefore be an unspliced RNA (e.g., mRNA), a partially spliced RNA (e.g., an mRNA where one or more introns have yet to be removed), or a fully spliced RNA (e.g., mRNA, "mature" mRNA), etc.

In some cases, the target sequence (i.e., the sequence with which a probe hybridizes) is present in more than one species of the target nucleic acid (e.g., the same sequence may be present in an unspliced, a partially spliced, and/or a fully spliced RNA). In such cases, the subject methods can be used to simultaneously detect more than one species of the target nucleic acid. For example, in some embodiments, the subject methods can be used to detect a specific splice variant of a target nucleic acid (e.g., mRNA) and/or a specific subset of splice variants of the target nucleic acid.

In some cases, the target sequence within the target nucleic acid is located at a splice junction of an mRNA molecule. In such cases, the subject method can be used to detect spliced and/or partially spliced species (i.e., versions) of the target nucleic acid. For example, in some cases, the target sequence spans a splice junction such that the target sequence was generated by the process of mRNA splicing (e.g., prior to splicing, the target sequence as a whole did not exist, and the sequences that make up the target sequence were brought together via splicing). In some such cases, the target sequence is equally distributed across the splice junction (e.g., each side of the splice junction has the same (or similar) number of targeted nucleotides). In some cases, the target sequence is non-equally distributed across the splice junction (e.g., each side of the splice junction does not have same number of targeted nucleotides). In some cases, one side of the splice junction has all targeted nucleotides except for one nucleotide (the one nucleotide being introduced as the result of splicing).

In some cases, the target sequence is present in an unspliced RNA (and/or partially spliced RNA)(e.g., mRNA), but is removed by the process of splicing. In such cases, the subject method can be used to detect unspliced and/or partially spliced species (i.e., versions) of the target nucleic acid. For example, in some cases, the target sequence spans a future splice junction such that the target sequence is destroyed by the process of mRNA splicing (e.g., prior to splicing, the target sequence exists, but the sequences that make up the target sequence are removed and/or rearranged via splicing). In some such cases, the target sequence is equally distributed across the future splice junction (e.g., each side of the future splice junction has the same (or similar) number of targeted nucleotides). In some cases, the target sequence is non-equally distributed across the future splice junction (e.g., each side of the future splice junction does not have same number of targeted nucleotides). In some cases, one side of the future splice junction has all targeted nucleotides except for one nucleotide (the one nucleotide being removed as the result of splicing).

In some embodiments, the target nucleic acid is a splice variant. The term "splice variant" is used herein to mean a species (i.e., version)(spliced, alternatively spliced, partially spliced, and/or unspliced version) of an RNA (e.g., an mRNA) that is not the most prevalent species under normal circumstances. For example, in some cases, a splice variant is a fully spliced RNA (e.g., mRNA), but is a variant species (or species of low abundance or non-existent under normal circumstances) (e.g., an alternatively spliced mRNA). In some cases, a splice variant is an unspliced or partially spliced RNA (e.g., mRNA), and can be considered to be a species of low abundance under normal circumstances. In some contexts, a splice variant may be the most prevalent species of target nucleic acid (e.g., RNA) under a particular context (e.g., disease, altered metabolism, experimental manipulation, e.g., drug stimulation, change in temperature, change in oxygen, etc.), but is still considered a splice variant because the species is not the most prevalent species under normal circumstances.

In some embodiments, the target sequence spans the junction of a fusion molecule (i.e., a fusion junction). For example, in some cases, a target nucleic acid (e.g., DNA, mRNA) is a fusion molecule (i.e., two nucleic acid molecules that are normally separate molecules)(e.g., a fusion gene transcript). For example, a fusion molecule can be a fusion DNA or a fusion mRNA molecule that codes for a fusion protein (two proteins that are normally separate and normally coded for by separate mRNA molecules). In some such cases, the target sequence spans the junction between the normally separated nucleic acid molecules (i.e., the fusion junction). In such cases, the subject methods can be used to specifically detect a fusion nucleic acid molecule (e.g., where the target sequence is only present in the targeted fusion nucleic acid molecule). For example, the subject methods can be used to detect DNA and/or RNA fusion molecules that result from disease-associated fusion events (e.g., cancer-associated gene fusions), DNA and/or RNA fusion molecules that result from human intervention (e.g., heterologous fusions such as DNA and/or mRNAs that encode fusion proteins, e.g., proteins that may or may not be fused to a tag), etc.

Suitable target nucleic acid molecules include polynucleotides of a wide range of lengths. In some instances, a target nucleic acid molecule is 10 or more, 15 or more, 20 or more, 25 or more, 30 or more, 35 or more, 40 or more, 60 or more, 80 or more, 100 or more, 150 or more, 200 or more, 300 or more, 400 or more, 500 or more, or 1,000 or more, 5,000 or more, or 10,000 more nucleotides in length. In some instances, the target nucleic acid includes 10 or more consecutive nucleotides of known sequence. For example, a target nucleic acid molecule can include 15 or more, 20 or more, 25 or more, 30 or more, 35 or more, 40 or more, 60 or more, 80 or more, 100 or more, 150 or more, 200 or more, 300 or more, 400 or more, 500 or more, or 1,000 or more consecutive nucleotides of known sequence. In some instances, the sequence of the target nucleic acid molecule is unknown.

In some cases, the target nucleic acid (e.g., miRNA, mature miRNA, etc.) has a length in the range of from 10 nucleotide (nt) to 50 nt (e.g., from 10 nt to 45 nt, from 10 nt to 40 nt, from 10 nt to 35 nt, from 10 nt to 30 nt, from 10 nt to 25 nt, from 15 nt to 45 nt, from 15 nt to 40 nt, from 15 nt to 35 nt, from 15 nt to 30 nt, from 15 nt to 25 nt, or from 17 nt to 23 nt).

In some cases, the target nucleic acid (e.g., immature miRNA, some mRNAs, etc.) has a length in the range of from 100 nt to 1500 nt (e.g., from 100 nt to 1200 nt, from 100 nt to 1000 nt, from 100 nt to 800 nt, from 100 nt to 600 nt, from 100 nt to 400 nt, from 250 nt to 1500 nt, from 400 nt to 1500 nt, from 600 nt to 1500 nt, from 800 nt to 1500 nt, from 1000 nt to 1500 nt, from 1200 nt to 1500 nt, from 200 nt to 1400 nt, from 300 nt to 1300 nt, from 500 nt to 1100 nt, from 600 nt to 1000 nt, or from 700 nt to 1000 nt).

In some cases, the target sequence of a target nucleic acid (e.g., miRNA, mature miRNA, splice junction, fusion junction, and the like) has a length in the range of from 10 nt to 50 nt (e.g., from 10 nt to 45 nt, from 10 nt to 40 nt, from 10 nt to 35 nt, from 10 nt to 30 nt, from 10 nt to 25 nt, from 15 nt to 45 nt, from 15 nt to 40 nt, from 15 nt to 35 nt, from 15 nt to 30 nt, from 15 nt to 25, or from 17 nt to 23 nt).

As will be described in greater detail below, aspects of the methods can include fixation, permeabilization, dehydration, rehydration, post-fixation, nuclease inhibition, sample storage, target detection, signal amplification, and signal detection. In some instances, the methods include contacting a cellular sample with a fixation reagent and a permeabilization reagent to produce a fixed/permeabilized cellular sample; contacting the fixed/permeabilized cellular sample with an aqueous post-fixation reagent to produce a rehydrated/fixed cellular sample; contacting the rehydrated/fixed cellular sample with a nuclease inhibitor; and evaluating the nuclease-contacted rehydrated/fixed cellular sample for the presence of the target nucleic acid (e.g., ribonucleic acid, deoxyribonucleic acid).

Fixation

Aspects of the invention include "fixing" a cellular sample. The term "fixing" or "fixation" as used herein is the process of preserving biological material (e.g., tissues, cells, organelles, molecules, etc.) from decay and/or degradation. Fixation may be accomplished using any convenient protocol. Fixation can include contacting the cellular sample with a fixation reagent (i.e., a reagent that contains at least one fixative). Cellular samples can be contacted by a fixation reagent for a wide range of times, which can depend on the temperature, the nature of the sample, and on the fixative(s).

For example, a cellular sample can be contacted by a fixation reagent for 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes.

A cellular sample can be contacted by a fixation reagent for a period of time in a range of from 5 minutes to 24 hours (e.g., from 10 minutes to 20 hours, from 10 minutes to 18 hours, from 10 minutes to 12 hours, from 10 minutes to 8 hours, from 10 minutes to 6 hours, from 10 minutes to 4 hours, from 10 minutes to 2 hours, from 15 minutes to 20 hours, from 15 minutes to 18 hours, from 15 minutes to 12 hours, from 15 minutes to 8 hours, from 15 minutes to 6 hours, from 15 minutes to 4 hours, from 15 minutes to 2 hours, from 15 minutes to 1.5 hours, from 15 minutes to 1 hour, from 10 minutes to 30 minutes, from 15 minutes to 30 minutes, from 30 minutes to 2 hours, from 45 minutes to 1.5 hours, or from 55 minutes to 70 minutes).

A cellular sample can be contacted by a fixation reagent at various temperatures, depending on the protocol and the reagent used. For example, in some instances a cellular sample can be contacted by a fixation reagent at a temperature ranging from −22° C. to 55° C., where specific ranges of interest include, but are not limited to: 50 to 54° C., 40 to 44° C., 35 to 39° C., 28 to 32° C., 20 to 26° C., 0 to 6° C., and −18 to −22° C. In some instances a cellular sample can be contacted by a fixation reagent at a temperature of −20° C., 4° C., room temperature (22-25° C.), 30° C., 37° C., 42° C., or 52° C.

Any convenient fixation reagent can be used. Common fixation reagents include crosslinking fixatives, precipitating fixatives, oxidizing fixatives, mercurials, and the like. Cross-linking fixatives chemically join two or more molecules by a covalent bond and a wide range of cross-linking reagents can be used. Examples of suitable cross-liking fixatives include but are not limited to aldehydes (e.g., formaldehyde, also commonly referred to as "paraformaldehyde" and "formalin"; glutaraldehyde; etc.), imidoesters, NHS (N-Hydroxysuccinimide) esters, and the like. Examples of suitable precipitating fixatives include but are not limited to alcohols (e.g., methanol, ethanol, etc.), acetone, acetic acid, etc. In some embodiments, the fixative is formaldehyde (i.e., paraformaldehyde or formalin). A suitable final concentration of formaldehyde in a fixation reagent is 0.1 to 10%, 1-8%, 1-4%, 1-2%, 3-5%, or 3.5-4.5%. In some embodiments the cellular sample is fixed in a final concentration of 4% formaldehyde (as diluted from a more concentrated stock solution, e.g., 38%, 37%, 36%, 20%, 18%, 16%, 14%, 10%, 8%, 6%, etc.). In some embodiments the cellular sample is fixed in a final concentration of 10% formaldehyde. In some embodiments the cellular sample is fixed in a final concentration of 1% formaldehyde. In some embodiments, the fixative is glutaraldehyde. A suitable concentration of glutaraldehyde in a fixation reagent is 0.1 to 1%.

A fixation reagent can contain more than one fixative in any combination. For example, in some embodiments the cellular sample is contacted with a fixation reagent containing both formaldehyde and glutaraldehyde.

Permeabilization

Aspects of the invention include "permeabilizing" a cellular sample. The terms "permeabilization" or "permeabilize" as used herein refer to the process of rendering the cells (cell membranes etc.) of a cellular sample permeable to experimental reagents such as nucleic acid probes, antibodies, chemical substrates, etc. Any convenient method and/or reagent for permeabilization can be used. Suitable permeabilization reagents include detergents (e.g., Saponin, Triton X-100, Tween-20, etc.), organic fixatives (e.g., acetone, methanol, ethanol, etc.), enzymes, etc. Detergents can be used at a range of concentrations. For example, 0.001%-1% detergent, 0.05%-0.5% detergent, or 0.1%-0.3% detergent can be used for permeabilization (e.g., 0.1% Saponin, 0.2% tween-20, 0.1-0.3% triton X-100, etc.).

In some embodiments, the same solution can be used as the fixation reagent and the permeabilization reagent. For example, in some embodiments, the fixation reagent contains 0.1%-10% formaldehyde and 0.001%-1% saponin. In some embodiments, the fixation reagent contains 1% formaldehyde and 0.3% saponin.

A cellular sample can be contacted by a permeabilization reagent for a wide range of times, which can depend on the temperature, the nature of the sample, and on the permeabilization reagent(s). For example, a cellular sample can be contacted by a permeabilization reagent for 24 or more hours (see storage described below), 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes. A cellular sample can be contacted by a permeabilization reagent at various temperatures, depending on the protocol and the reagent used. For example, in some instances a cellular sample can be contacted by a permeabilization reagent at a temperature ranging from −82° C. to 55° C., where specific ranges of interest include, but are not limited to: 50 to 54° C., 40 to 44° C., 35 to 39° C., 28 to 32° C., 20 to 26° C., 0 to 6° C., −18 to −22° C., and −78 to −82° C. In some instances a cellular sample can be contacted by a permeabilization reagent at a temperature of −80° C., −20° C., 4° C., room temperature (22-25° C.), 30° C., 37° C., 42° C., or 52° C.

In some embodiments, a cellular sample is contacted with an enzymatic permeabilization reagent. Enzymatic permeabilization reagents that permeabilize a cellular sample by partially degrading extracellular matrix or surface proteins that hinder the permeation of the cellular sample by assay reagents. Contact with an enzymatic permeabilization reagent can take place at any point after fixation and prior to target detection. In some instances the enzymatic permeabilization reagent is proteinase K, a commercially available enzyme. In such cases, the cellular sample is contacted with proteinase K prior to contact with a post-fixation reagent (described below). Proteinase K treatment (i.e., contact by proteinase K; also commonly referred to as "proteinase K digestion") can be performed over a range of times at a range of temperatures, over a range of enzyme concentrations that are empirically determined for each cell type or tissue type under investigation. For examples, a cellular sample can be contacted by proteinase K for 30 or less minutes, 25 or less minutes, 20 or less minutes, 15 or less minutes, 10 or less minutes, 5 or less minutes, or 2 or less minutes. A cellular sample can be contacted by 1 ug/ml or less, 2 ug/ml or less, 4 ug/ml or less, 8 ug/ml or less, 10 ug/ml or less, 20 ug/ml or less, 30 ug/ml or less, 50 ug/ml or less, or 100 ug/ml or less proteinase K. A cellular sample can be contacted by proteinase K at a temperature ranging from 2° C. to 55° C., where specific ranges of interest include, but are not limited to: 50 to 54° C., 40 to 44° C., 35 to 39° C., 28 to 32° C., 20 to 26° C., and 0 to 6° C. In some instances a cellular sample can be contacted by proteinase K at a temperature of 4° C., room temperature (22-25° C.), 30° C., 37° C., 42° C., or 52° C. In some embodiments, a cellular sample is not contacted with an enzymatic permeabilization reagent. In some embodiments, a cellular sample is not contacted with proteinase K.

Contact of a cellular sample with at least a fixation reagent and a permeabilization reagent results in the production of a fixed/permeabilized cellular sample.

Dehydration

Aspects of the invention include "dehydrating" a cellular sample. The term "dehydration" as used herein refers to the replacement of an aqueous sample diluent with a non-aqueous diluent (i.e., a dehydration reagent, e.g., an alcohol). In some embodiments, dehydration refers to the replacement of aqueous solution from a cellular sample with an alcohol (e.g., methanol, ethanol).

A cellular sample can be contacted by a dehydration reagent for 12 months or less, 6 months or less, 2 months or less, 2 weeks or less, 24 hours or less, 18 hours or less, 12 hours or less, 8 hours or less, 6 hours or less, 4 hours or less, 2 hours or less, 60 minutes or less, 45 minutes or less, 30 minutes or less, 25 minutes or less, 20 minutes or less, 15 minutes or less, 10 minutes or less, 5 minutes or less, or 2 minutes or less. A cellular sample can be contacted by a dehydration reagent at various temperatures, depending on the protocol. For example, in some instances a cellular sample can be contacted by a dehydration reagent at a temperature ranging from −82° C. to 55° C., where specific ranges of interest include, but are not limited to: 50 to 54° C., 40 to 44° C., 35 to 39° C., 28 to 32° C., 20 to 26° C., 0 to 6° C., −18 to −22° C., and −78 to −82° C. In some instances a cellular sample can be contacted by a dehydration reagent at a temperature of −80° C., −20° C., 4° C., room temperature (22-25° C.), 30° C., 37° C., 42° C., or 52° C.

In cases where an alcohol (e.g., methanol or ethanol) is used as a permeabilization reagent (see previous section), permeabilization and dehydration occur simultaneously and the step can simply be referred to as a permeabilization step. As such, when an alcohol is used as a permeabilization reagent, the cellular sample is a dehydrated fixed/permeabilized cellular sample. Therefore, the term "fixed/permeabilized cellular sample" can be used to describe either a cellular sample that has not been dehydrated (e.g., when the permeabilization reagent is not an alcohol) or a cellular sample that has been dehydrated (e.g., when the permeabilization reagent is an alcohol). As described below, a cellular sample that has been dehydrated can be stored prior to rehydration.

Rehydration

Aspects of the invention include "rehydrating" a cellular sample. The term "rehydration" as used herein refers to the replacement of a non-aqueous solution such as alcohol (e.g., methanol, ethanol, etc.) with an aqueous solution (i.e., a rehydration reagent). The replacement can be accomplished by centrifugation to pellet the cells of the cellular sample, removing the supernatant, and replacing the alcohol with a new solution. Rehydration can be performed in one step by replacing the alcohol with a fully aqueous solution (e.g., a solution that does not contain alcohol) or it can be performed in more than one step by re-suspending the cells in a series of solutions with decreasing alcohol content. For example, a two-step rehydration can include the replacement of 100% methanol with 50% methanol, followed by replacement with a fully aqueous solution; and a four-step rehydration can include the replacement of 100% methanol with 75% methanol, followed by replacement with 50% methanol, followed by replacement with 25% methanol, followed by replacement with a fully aqueous solution.

A cellular sample can be contacted by a rehydration reagent for 60 minutes or less, 45 minutes or less, 30 minutes or less, 25 minutes or less, 20 minutes or less, 15 minutes or less, 10 minutes or less, 5 minutes or less, or 2 minutes or less. A cellular sample can be contacted by a rehydration reagent at various temperatures, depending on the protocol. For example, a cellular sample can be contacted by a rehydration reagent at a temperature ranging from 2° C. to 55° C., where specific ranges of interest include, but are not limited to: 50 to 54° C., 40 to 44° C., 35 to 39° C., 28 to 32° C., 20 to 26° C., and 0 to 6° C. In some instances a cellular sample can be contacted by a rehydration reagent at a temperature of 4° C., room temperature (22-25° C.), 30° C., 37° C., 42° C., or 52° C.

Once rehydrated, the sample can be referred to as a rehydrated cellular sample. Contact of a cellular sample with at least a fixation reagent, a dehydration reagent, and a rehydration reagent results in the production of a rehydrated/fixed cellular sample. The term "rehydrated/fixed cellular sample" can therefore be used to describe either a cellular sample that has been post-fixed (see below, e.g., when the rehydration reagent includes a fixative) or a cellular sample that has not been post-fixed (e.g., when the rehydration reagent does not include a fixative).

Post-Fixation

Aspects of the invention include "post-fixing" a cellular sample The term "post-fixation" as used herein refers to the process of re-contacting a cellular sample with at least one post-fixation reagent (i.e., a reagent containing at least one fixative). This step can also be considered a "secondary fixation" step because the cellular sample has previously been contacted by a fixation reagent. Suitable post-fixation reagents are the same as the suitable fixation reagents and the cellular sample can be contacted by a post-fixation reagent at the same concentrations (e.g., same range of concentrations), for the same periods of time (e.g., range of times), at the same temperatures (e.g., ranges of temperatures) as for the fixation step. The post-fixation protocol (i.e., the reagent used, the contact time, the temperature, etc) can be the same as that used for the fixation step or it can be different than the fixation step. For example, the cellular sample can be contacted by a post-fixation reagent that is the same as or different than the fixation reagent which it previously contacted.

In some embodiments the cellular sample is post-fixed (i.e., contacted by a post-fixation reagent, e.g., an aqueous post-fixation reagent) after a rehydration step. In some embodiments, the aqueous solution (i.e., rehydration reagent) used to replace the alcohol during rehydration is also a fixation reagent (i.e., an aqueous post-fixation reagent that contains a fixative, e.g., 1% formaldehyde, 4% formaldehyde, etc.) and the rehydration step is therefore also a post-fixation step.

Nuclease Inhibition

Aspects of the invention include contacting a cellular sample with a nuclease inhibitor. As used herein, a "nuclease inhibitor" is any molecule that can be used to inhibit nuclease activity within the cellular sample such that integrity of the nucleic acids within the cells of the cellular sample is preserved. In other words, degradation of the nucleic acids within the cells of the cellular sample by nuclease activity is inhibited by contacting the cellular sample with a nuclease inhibitor. In some embodiments, the nuclease inhibitor is an RNase inhibitor (i.e., the inhibitor inhibits RNase activity). Examples of suitable commercially available nuclease inhibitors include, but are not limited to non-protein based inhibitors (e.g., aurintricarboxylic acid (ATA); Diethyl Pyrocarbonate (DEPC); RNAsecure™ Reagent from Life Technologies; and the like) and protein based inhibitors (e.g., ribonuclease inhibitor from EMD Millipore; RNaseOUT™ Recombinant Ribonuclease Inhibitor, SUPERaseIn™, ANTI-RNase, and RNase Inhibitor from Life Technologies; RNase Inhibitor and Protector RNase Inhibitor from Roche; RNAsin from Promega, and the like). Nuclease inhibitors can be used at a range of concentrations as recommended by their commercial sources.

A cellular sample can be contacted by a nuclease inhibitor at any time prior to the target nucleic acid detection step (see below). For example, a cellular sample can be contacted with a nuclease inhibitor after the sample is rehydrated and post-fixed to produce a nuclease inhibitor-contacted rehydrated/fixed cellular sample.

Storage

A cellular sample can be stored, when desired, for an extended period of time prior to the target nucleic acid detection step. In some instances, the extended period of time is 1 week or longer, e.g., 1 month or longer, including 6 months or longer, e.g., 1 year or longer. In some instances, the extended period of time ranges from 1 week to 5 years, e.g., 2 weeks to 4 years, 4 weeks to 3 years, 8 weeks to 2 years, or 12 weeks to 1 year. In some instances, the cellular sample can be stored at a temperature below 0° C. (e.g., below −19° C., below −79° C., etc.) as a dehydrated cellular sample (i.e., while being contacted by a dehydration reagent and prior to rehydration). In some embodiments, the sample can be stored as a nuclease inhibitor-contacted rehydrated/fixed cellular sample, prior to target nucleic acid detection. In such cases, the cellular sample is stored at 2-6° C. in an aqueous buffer that includes a nuclease inhibitor.

Protein Detection Reagents

Aspects of the invention may include contacting the cellular sample with a protein detection reagent. The term "protein detection reagent" as used herein refers to any reagent that specifically binds to a target protein (e.g., a target protein of a cell of the cellular sample) and facilitates the qualitative and/or quantitative detection of the target protein. The terms "specific binding," "specifically binds," and the like, refer to the preferential binding to a molecule relative to other molecules or moieties in a solution or reaction mixture. In some embodiments, the affinity between protein detection reagent and the target protein to which it specifically binds when they are specifically bound to each other in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower $K_d$.

In some embodiments, a protein detection reagent includes a label or a labeled binding member. A "label" or "label moiety" is any moiety that provides for signal detection and may vary widely depending on the particular nature of the assay. Label moieties of interest include both directly and indirectly detectable labels. Suitable labels for use in the methods described herein include any moiety that is indirectly or directly detectable by spectroscopic, photochemical, biochemical, immunochemical, electrical, optical, chemical, or other means. For example, suitable labels include biotin for staining with labeled streptavidin conjugate, a fluorescent dye (e.g., fluorescein, Texas red, rhodamine, a flurochrome label such as an ALEXA FLUOR® label, and the like), a radiolabel (e.g., $^3$H, $^{125}$I, $^{35}$S, $^{14}$C, or $^{32}$P), an enzyme (e.g., peroxidase, alkaline phosphatase, galactosidase, and others commonly used in an ELISA), a fluorescent protein (e.g., green fluorescent protein, red fluorescent protein, yellow fluorescent protein, and the like), a metal label, a colorimetric label, and the like. Fluorescent labels can be detected using a photodetector (e.g., in a flow cytometer) to detect emitted light. Enzymatic labels are typically detected by providing the enzyme with a substrate and detecting the reaction product produced by the action of the enzyme on the substrate, and colorimetric labels are detected by simply visualizing the colored label.

Metal labels (e.g., $Sm^{152}$, $Tb^{159}$, $Er^{170}$, $Nd^{146}$, $Nd^{142}$, and the like) can be detected (e.g., the amount of label can be measured) using any convenient method, including, for example, mass cytometry (see, for example: (i) U.S. Pat. No. 7,479,630; (ii) Wang et al., Cytometry A. 2012 July; 81(7): 567-75: "Human CD4+ lymphocytes for antigen quantification: characterization using conventional flow cytometry and mass cytometry"; (iii) Bandura et. al., Anal Chem. 2009 Aug. 15; 81(16):6813-22: "Mass cytometry: technique for real time single cell multitarget immunoassay based on inductively coupled plasma time-of-flight mass spectrometry"; and (iv) Ornatsky et. al., J Immunol Methods. 2010 Sep. 30; 361(1-2):1-20: "Highly multiparametric analysis by mass cytometry"; all of which are hereby incorporated by reference in their entirety), which, as with flow cytometry, is a method of single cell analysis. As described above, mass cytometry is a real-time quantitative analytical technique whereby cells or particles are individually introduced into a mass spectrometer (e.g., Inductively Coupled Plasma Mass Spectrometer (ICP-MS)), and a resultant ion cloud (or multiple resultant ion clouds) produced by a single cell is analyzed (e.g., multiple times) by mass spectrometry (e.g., time of-flight mass spectrometry). Mass cytometry can use elements (e.g., a metal) or stable isotopes, attached as label moieties to a detection reagent (e.g., an antibody and/or a nucleic acid detection agent).

In some instances, a protein detection reagent is a polyclonal or monoclonal antibody or a binding fragment thereof (i.e., an antibody fragment that is sufficient to bind to the target of interest, e.g., the protein target). Antibody fragments (i.e., binding fragments) can be, for example, monomeric Fab fragments, monomeric Fab' fragments, or dimeric F(ab)'$_2$ fragments. Also within the scope of the term "antibody or a binding fragment thereof" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

Stimulating Agents

Aspects of the invention may include contacting the cellular sample with a "stimulating agent", also referred to herein as a "stimulator." By stimulating agent it is meant any compound that affects at least one cellular activity or that alters the cellular steady state (i.e., induced or reduced in abundance or activity). Contacting a cellular sample with a stimulating agent can be used to ascertain the cellular response to the agent. By "effective amount" of a stimulating agent, it is meant that a stimulating agent is present in an amount to affect at least one cellular activity that alters the cellular steady state (i.e., induced or reduced in abundance or activity). A stimulating agent can be provided as a powder or as a liquid. As such, a stimulating agent can include various compounds and formulations, such as intracellular signal inducing and immunomodulatory agents. Examples include small molecule drugs as well as peptides, proteins, lipids carbohydrates and the like. Of particular interest are compounds such as type I interferons (e.g., IFN-α, IFN-β), interleukins (e.g., interleukin-2 (IL-2), IL-4, IL-6, IL-7, IL-10, IL-12, IL-15, IL-21), tumor necrosis factor alpha (TNF-α), gamma interferon (IFN-γ), transforming growth factor β, and the like. In some embodiments, the stimulating agent includes an immunomodulatory cytokine, such as immunomodulatory cytokines represented by interferons, interleukins, and chemokines among others. Interferon alpha is of specific interest.

Target Nucleic Acid Detection and Signal Amplification

The subject methods are methods of assaying for the presence of a target nucleic acid. As such, the subject methods are methods (when a target nucleic acid is present in a cell of a cellular sample) of detecting the target nucleic acid, producing a signal in response to target nucleic acid detection, and detecting the produced signal. The signal produced by a detected target nucleic acid can be any detectable signal (e.g., a fluorescent signal, an amplified fluorescent signal, a chemiluminescent signal, etc.)

Aspects of the invention include methods of detecting a target nucleic acid (i.e., target nucleic acid detection). In some embodiments, the cellular sample is contacted with a nucleic acid detection agent. As used herein, the term "nucleic acid detection agent" means any reagent that can specifically bind to a target nucleic acid. For example, suitable nucleic acid detection agents can be nucleic acids (or modified nucleic acids) that are at least partially complementary to and hybridize with a sequence of the target nucleic acid. In some embodiments, the nucleic acid detection agent includes a probe or set of probes (i.e., probe set), each of which specifically binds (i.e., hybridizes to) a sequence (i.e., target sequence) of the target nucleic acid.

A nucleic acid is "complementary" or "hybridizable" to another nucleic acid, such as a cDNA, genomic DNA, or RNA, when a single stranded form of the nucleic acid can "base-pair" with or "anneal" to the other nucleic acid in a sequence specific manner (i.e., a nucleic acid specifically binds to a complementary nucleic acid) under the appropriate in vitro or in vivo conditions of temperature and solution ionic strength. Hybridization requires that the two nucleic acids contain complementary sequences although mismatches between bases are possible such that 100% complementarity is not an absolute requirement. The conditions appropriate for hybridization between two nucleic acids depend on the length of the nucleic acids and the degree of complementarity, where the greater the degree of complementarity, the stronger the hybridization (i.e., the greater the value of the melting temperature (Tm)). In some instances, suitable hybridizable nucleic acids are composed of 10 or more, 15 or more, 20 or more, 25 or more, or 30 or more nucleotides. The skilled artisan will recognize that the strength (i.e., degree) of hybridization also depends on temperature and wash solution salt concentration, both of which may be adjusted as necessary. Percent complementarity between particular stretches of nucleic acid sequences within nucleic acids can be determined routinely using readily available sequence alignment programs (e.g., BLAST (basic local alignment search tools)).

In some embodiments, a nucleic acid detection agent includes a signal producing system. A signal producing system can have one or more components and can be any system that provides a signal when the nucleic acid detection agent detects a target nucleic acid. In some instances, a signal producing system includes a labeled nucleic acid probe. A labeled nucleic acid probe is a nucleic acid that is labeled with any label moiety. As such, a nucleic acid detection agent can include a signal producing system that includes a labeled nucleic acid probe. In some embodiments, the nucleic acid detection agent is a single labeled molecule (i.e., a labeled nucleic acid probe) that specifically binds to the target nucleic acid. In some embodiments, the nucleic acid detection agent includes multiple molecules, one of which specifically binds to the target nucleic acid. In such embodiments, when a labeled nucleic acid probe is present, the labeled nucleic acid probe does not specifically bind to the target nucleic acid, but instead specifically binds to one of the other molecules of the nucleic acid detection agent.

A "label" or "label moiety" for a nucleic acid probe is any moiety that provides for signal detection and may vary widely depending on the particular nature of the assay. Label moieties of interest include both directly and indirectly detectable labels. Suitable labels for use in the methods described herein include any moiety that is indirectly or directly detectable by spectroscopic, photochemical, biochemical, immunochemical, electrical, optical, chemical, or other means. For example, suitable labels include antigenic labels (e.g., digoxigenin (DIG), fluorescein, dinitrophenol (DNP), etc.), biotin for staining with labeled streptavidin conjugate, a fluorescent dye (e.g., fluorescein, Texas red, rhodamine, a flurochrome label such as an ALEXA FLUOR® label, and the like), a radiolabel (e.g., $^3$H, $^{125}$I, $^{35}$S, $^{14}$C, or $^{32}$P), an enzyme (e.g., peroxidase, alkaline phosphatase, galactosidase, and others commonly used in an ELISA), a fluorescent protein (e.g., green fluorescent protein, red fluorescent protein, yellow fluorescent protein, and the like), a metal label, a colorimetric label, and the like. An antigenic label can be incorporated into the nucleic acid on any nucleotide (e.g., A,U,G,C).

Fluorescent labels can be detected using a photodetector (e.g., in a flow cytometer) to detect emitted light. Enzymatic labels are typically detected by providing the enzyme with a substrate and detecting the reaction product produced by the action of the enzyme on the substrate, colorimetric labels can be detected by simply visualizing the colored label, and antigenic labels can be detected by providing an antibody (or a binding fragment thereof) that specifically binds to the antigenic label. An antibody that specifically binds to an antigenic label can be directly or indirectly detectable. For example, the antibody can be conjugated to a label moiety (e.g., a fluorophore) that provides the signal (e.g., fluorescence); the antibody can be conjugated to an enzyme (e.g., peroxidase, alkaline phosphatase, etc.) that produces a detectable product (e.g., fluorescent product) when provided with an appropriate substrate (e.g., fluorescent-tyramide, FastRed, etc.); etc.

Metal labels (e.g., $Sm^{152}$, $Tb^{159}$, $Er^{170}$, $Nd^{146}$, $Nd^{142}$, and the like) can be detected (e.g., the amount of label can be measured) using any convenient method, including, for example, mass cytometry (see, for example: (i) U.S. Pat. No. 7,479,630; (ii) Wang et al., Cytometry A. 2012 July; 81(7): 567-75: "Human CD4+ lymphocytes for antigen quantification: characterization using conventional flow cytometry and mass cytometry"; (iii) Bandura et. al., Anal Chem. 2009 Aug. 15; 81(16):6813-22: "Mass cytometry: technique for real time single cell multitarget immunoassay based on inductively coupled plasma time-of-flight mass spectrometry"; and (iv) Ornatsky et. al., J Immunol Methods. 2010 Sep. 30; 361(1-2):1-20: "Highly multiparametric analysis by mass cytometry"), which, as with flow cytometry, is a method of single cell analysis. As described above, mass cytometry is a real-time quantitative analytical technique whereby cells or particles are individually introduced into a mass spectrometer (e.g., Inductively Coupled Plasma Mass Spectrometer (ICP-MS)), and a resultant ion cloud (or multiple resultant ion clouds) produced by a single cell is analyzed (e.g., multiple times) by mass spectrometry (e.g., time of-flight mass spectrometry). Mass cytometry can use elements (e.g., a metal) or stable isotopes, attached as label moieties to a detection reagent (e.g., an antibody and/or a nucleic acid detection agent).

In some cases the signal produced by the detection of the target nucleic acid is amplified prior to signal detection. As such, a signal producing system of a nucleic acid detection agent can include a signal amplification component. A signal amplification component is any component that facilitates the amplification of signal. Examples of signal amplification components include but are not limited to enzymes (either unconjugated or conjugated to an antibody for fragment thereof) that produce detectable products when contacted with appropriate substrate; branched nucleic acids; and the like. In some instances, a signal amplification component is a branched nucleic acid. In such cases, the signal amplification can be referred to as branched nucleic acid (e.g., DNA) signal amplification (e.g., bDNA signal amplification). A branched nucleic acid (e.g., bDNA) is a series of nucleic acids (and/or modified nucleic acids, as described below) that hybridize to each other (e.g., in multiple locations), thus taking on a branch-shaped structure.

In some bDNA assays for gene expression analysis, a target nucleic acid (e.g., an RNA, e.g., an mRNA, a microRNA, etc.) whose expression is to be detected is released from cells and captured by a Capture Probe (CP) on a solid surface (e.g., a well of a microtiter plate) through synthetic oligonucleotide probes called Capture Extenders (CEs). Each capture extender has a first polynucleotide sequence that can hybridize to the target nucleic acid and a second polynucleotide sequence that can hybridize to the capture probe. In some cases, two or more capture extenders are used. Probes of another type, called Label Extenders (LEs), hybridize to different sequences on the target nucleic acid and to sequences on an amplification multimer. Additionally, Blocking Probes (BPs), which hybridize to regions of the target nucleic acid not occupied by CEs or LEs, can be used to reduce non-specific target probe binding. A probe set for a given nucleic acid thus consists of CEs, LEs, and/or BPs for the target nucleic acid. The CEs, LEs, and BPs are complementary to nonoverlapping sequences in the target nucleic acid, and can be contiguous.

Signal amplification begins with the binding of the LEs to the target nucleic acid. An amplification multimer can then be hybridized to the LEs. The amplification multimer can have multiple copies of a sequence that is complementary to a label probe (the amplification multimer can be a branched-chain nucleic acid; for example, the amplification multimer can be a branched, forked, or comb-like nucleic acid or a linear nucleic acid). A label can be covalently attached to each label probe, as discussed above for a nucleic probe (e.g., a fluorescent label, e.g., a fluorescent dye, a fluorochrome label, etc.; an enzyme, e.g., peroxidase, alkaline phosphatase, galactosidase, etc.; a metal label; and the like). Alternatively, the label can be noncovalently bound to the label probes. Labeled complexes can then be detected (e.g., by fluorescence detection; by the alkaline phosphatase-mediated degradation of a chemilumigenic substrate, e.g., dioxetane; etc.). Luminescence and/or fluorescence can be reported in any convenient way (e.g., as relative fluorescence units, as relative light unit (RLUs) on a microplate reader, etc.). The amount of chemiluminescence is proportional to the level of target nucleic acid.

In the preceding example, the amplification multimer and the label probes comprise a label probe system. In another example, the label probe system also comprises a preamplifier, e.g., as described in U.S. Pat. Nos. 5,635,352 and 5,681,697, which further amplifies the signal from a single target nucleic acid. In yet another example, the label extenders hybridize directly to the label probes and no amplification multimer or preamplifier is used, so the signal from a single target nucleic acid molecule is only amplified by the number of distinct label extenders that hybridize to the target nucleic acid.

Basic bDNA assays have been well described. See, e.g., U.S. Pat. No. 4,868,105 to Urdea et al. entitled "Solution phase nucleic acid sandwich assay"; U.S. Pat. No. 5,635,352 to Urdea et al. entitled "Solution phase nucleic acid sandwich assays having reduced background noise"; U.S. Pat. No. 5,681,697 to Urdea et al. entitled "Solution phase nucleic acid sandwich assays having reduced background noise and kits therefor"; U.S. Pat. No. 5,124,246 to Urdea et al. entitled "Nucleic acid multimers and amplified nucleic acid hybridization assays using same"; U.S. Pat. No. 5,624, 802 to Urdea et al. entitled "Nucleic acid multimers and amplified nucleic acid hybridization assays using same"; U.S. Pat. No. 5,849,481 to Urdea et al. entitled "Nucleic acid hybridization assays employing large comb-type branched polynucleotides"; U.S. Pat. No. 5,710,264 to Urdea et al. entitled "Large comb type branched polynucleotides"; U.S. Pat. No. 5,594,118 to Urdea and Horn entitled "Modified N-4 nucleotides for use in amplified nucleic acid hybridization assays"; U.S. Pat. No. 5,093,232 to Urdea and Horn entitled "Nucleic acid probes"; U.S. Pat. No. 4,910,300 to Urdea and Horn entitled "Method for making nucleic acid probes"; U.S. Pat. Nos. 5,359,100; 5,571,670; 5,614,362; 6,235,465; 5,712,383; 5,747,244; 6,232,462; 5,681,702; 5,780,610; 5,780,227 to Sheridan et al. entitled "Oligonucleotide probe conjugated to a purified hydrophilic alkaline phosphatase and uses thereof"; U.S. patent application Publication No. US2002172950 by Kenny et al. entitled "Highly sensitive gene detection and localization using in situ branched-DNA hybridization"; Wang et al. (1997) "Regulation of insulin preRNA splicing by glucose" Proc Nat Acad Sci USA 94:4360-4365; Collins et al. (1998) "Branched DNA (bDNA) technology for direct quantification of nucleic acids: Design and performance" in Gene Quantification, F Ferre, ed.; and Wilber and Urdea (1998) "Quantification of HCV RNA in clinical specimens by branched DNA (bDNA) technology" Methods in Molecular Medicine: Hepatitis C 19:71-78.

Additional exemplary publications that describe branched nucleic acids and methods that use bDNA assays (including multiplex assays) also include, for example, U.S. patent applications: 2006/0263769, 2009/0081688, 2010/0099175, 2012/0003648, 2012/0004132, 2012/0052498, 2012/0172246, 2012/0071343, 2012/0214152, 2012/0100540, 2013/0023433, and 2013/0171621; as well as U.S. Pat. Nos. 7,033,758; 7,709,198; 7,803,541; and 8,114,681, all of which are hereby incorporated by reference in their entirety.

FIG. 1A schematically depicts an embodiment of the invention that includes a branched nucleic acid signal amplification component 3 and 4 to detect a target nucleic acid 1. The nucleic acid detection agent 2-5 of FIG. 1A includes a probe set 2 and a signal producing system 3-5 having both a labeled nucleic acid probe 5 (i.e., detector) and a branched nucleic acid 3 (i.e., pre-amplifier) and 4 (i.e., amplifier). The steps and elements of the target detection and signal production depicted in FIG. 1A are described in U.S. applications US 2010/0099175 and US 2009/0081688. In FIG. 1A the target nucleic acid 1 is detected by the probe set 2, which is made up of multiple oligonucleotides (probes) that hybridize to various predetermined segments along the target nucleic acid 1. Several molecules 3 (i.e., pre-amplifier) and 4 (i.e., amplifier) of the branched nucleic acid hybridize to each other, thus creating a branched nucleic acid structure. A labeled nucleic acid probe 5 (i.e., detector) specifically binds to the branched nucleic acid 3 and 4. Thus, each oligonucleotide of the probe set 2 will be marked by several labeled nucleic acid probes 5 via signal amplification by the branched nucleic acid 3 and 4.

Modified Nucleic Acids

In some embodiments, a nucleic acid detection agent (e.g., a probe) is a modified nucleic acid. A modified nucleic acid has one or more modifications, e.g., a base modification, a backbone modification, etc, to provide the nucleic acid with a new or enhanced feature (e.g., improved stability). A nucleoside can be a base-sugar combination, the base portion of which is a heterocyclic base. Heterocyclic bases include the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In some cases, the respective ends of this linear polymeric compound can be further joined to form a circular compound. In addition, linear compounds may have internal nucleotide base complementarity and may therefore fold in a manner as to produce a fully or partially double-stranded compound. Within oligonucleotides, the phosphate groups can be referred to as forming the internucleoside backbone of the oligonucleotide. The linkage or backbone of RNA and DNA can be a 3' to 5' phosphodiester linkage.

—Modified Backbones and Modified Internucleoside Linkages—

Examples of suitable nucleic acids containing modifications include nucleic acids with modified backbones or non-natural internucleoside linkages. Nucleic acids having modified backbones include those that retain a phosphorus atom in the backbone and those that do not have a phosphorus atom in the backbone. Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity include a single 3' to 3' linkage at the 3'-most internucleotide linkage i.e. a single inverted nucleoside residue which may be abasic (the nucleobase is missing or has a hydroxyl group in place thereof). Various salts (such as, for example, potassium or sodium), mixed salts and free acid forms are also included.

In some embodiments, a subject nucleic acid has one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some embodiments, a subject nucleic acid includes a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

—Mimetics—

A detection nucleic acid can be a nucleic acid mimetic. The term "mimetic" as it is applied to polynucleotides encompasses polynucleotides where only the furanose ring or both the furanose ring and the internucleotide linkage are replaced with non-furanose groups, replacement of only the furanose ring is also referred to as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of suitable polynucleotide mimetic is based on linked morpholino units (morpholino nucleic acid) having heterocyclic bases attached to the morpholino ring. A number of linking groups have been reported that can link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

Another suitable class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). The incorporation of CeNA monomers into a DNA chain increases the stability of a DNA/RNA hybrid. CeNA oligoadenylates formed complexes with RNA and DNA complements with similar stability to the native complexes. The incorporation CeNA structures into natural nucleic acid structures was shown by NMR and circular dichroism to proceed with conformational adaptation.

Also suitable as modified nucleic acids are Locked Nucleic Acids (LNAs) and/or LNA analogs. In an LNA, the 2'-hydroxyl group is linked to the 4' carbon atom of the sugar ring thereby forming a 2'-C,4'-C-oxymethylene linkage, and thereby forming a bicyclic sugar moiety. The linkage can be a methylene ($-CH_2-$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO98/39352 and WO99/14226, both of which are hereby incorporated by reference in their entirety. Exemplary LNA analogs are described in U.S. Pat. Nos. 7,399,845 and 7,569,686, both of which are hereby incorporated by reference in their entirety.

In some cases (e.g., when the target nucleic acid is a miRNA, when the target sequence of the target nucleic acid spans a splice junction or a fusion junction, etc.), the nucleic acid detection agent is an LNA.

—Modified Sugar Moieties—

A detection nucleic acid can also include one or more substituted sugar moieties. Suitable polynucleotides include a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are $O((CH_2)_nO)_m$ $CH_3$, $O(CH_2)_nOCH_3$, $O(CH_2)_nNH_2$, $O(CH_2)_nCH_3$, $O(CH_2)_n$ $ONH_2$, and $O(CH_2)_nON((CH_2)_nCH_3)_2$, where n and m are from 1 to about 10. Other suitable polynucleotides include a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, and other substituents having similar properties. A suitable modification can include 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A suitable modification can include 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also referred to as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2$ $CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

—Base Modifications and Substitutions—

A detection nucleic acid may also include a nucleobase (also referred to as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Modified nucleobases also include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), and pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

—Conjugates—

Another suitable modification of a subject nucleic acid involves chemically linking to the polynucleotide one or more moieties or conjugates. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, and polyethers. Suitable conjugate groups include, but are not limited to, cholesterols, lipids, phospholipids, biotin, phenazine, folate, phenanthridine, anthraquinone, acridine, fluoresceins, rhodamines, coumarins, and dyes.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

Signal Detection and Detection Devices

Aspects of the invention include detecting a signal resulting from the detection of a target nucleic acid. Signal detection can be carried out using any instrument (e.g., liquid assay device) that can measure the fluorescent, luminescent, light-scattering or colorimetric signal(s) output from the subject methods. In some embodiments, the signal resulting from the detection of a target nucleic acid is detected by a flow cytometer.

Aspects of the invention include a liquid assay device containing a fixed, permeabilized, and rehydrated cellular sample containing a nuclease inhibitor (e.g., RNase inhibitor) and a nucleic acid detection agent (see above). In some embodiments, the liquid assay device further includes a protein detection reagent (see above).

In some embodiments, the liquid assay device for evaluating a cellular sample for the presence of the target nucleic acid is a flow cytometer. As such, in some instances, the evaluation of whether a target nucleic acid is present in a cell of a cellular sample includes flow cytometrically analyzing the cellular sample. In flow cytometry, cells of a cellular sample are suspended in a stream of fluid, which is passed, one cell at a time, by at least one beam of light (e.g., a laser light of a single wavelength). A number of detectors, including one or more fluorescence detectors, detect scattered light as well as light emitted from the cellular sample (e.g., fluorescence). In this way, the flow cytometer acquires data that can be used to derive information about the physical and chemical structure of each individual cell that passes through the beam(s) of light. If a signal specific to the detection of a target nucleic acid is detected in a cell by the flow cytometer, then the target nucleic acid is present in the cell. In some embodiments, the detected signal is quantified using the flow cytometer.

Utility

The methods, devices, compositions and kits of the invention find use in a variety of different applications. Methods of the invention are methods of evaluating cells of a cellular sample, where the target nucleic acid may or may not be present. In some cases, it is unknown prior to performing the assay whether a cell of the cellular sample expresses the target nucleic acid. In other instances, it is unknown prior to performing the assay whether a cell of the cellular sample expresses the target nucleic acid in an amount (or relative amount, e.g., relative to another nucleic acid or relative to the amount of the target nucleic acid in a normal cell) that is greater than (exceeds) a predetermined threshold amount (or relative amount). In such cases, the methods are methods of evaluating cells of a cellular sample in which the target nucleic acid of interest may or may not be present in an amount that is greater than (exceeds) or below than a predetermined threshold. In some embodiments, the methods of the invention can be used to determine the expression level (or relative expression level) of a nucleic acid in one or more (or all) individual cell(s) of a cellular sample.

The methods of the invention can be used to identify a cell of a cell sample as aberrant or non-aberrant. For example, some mRNAs (and/or miRNAs) are known to be expressed above a particular level, or relative level, (i.e., above a predetermined threshold) in aberrant cells (e.g., cancerous cells). Thus, when the level (or relative level) of signal (as detected using the subject methods) for a particular target nucleic acid (e.g., mRNA) of a cell of the cellular sample indicates that the level (or relative level) of the target nucleic acid is equal to or greater than the level (or relative level) known to be associated with an aberrant cell, then the cell of the cellular sample is determined to be aberrant. To the contrary, some mRNAs (and/or miRNAs) are known to be expressed below a particular level, or relative level, (i.e., below a predetermined threshold) in aberrant cells (e.g., cancerous cells). Thus, when the level (or relative level) of signal (as detected using the subject methods) for a particular target nucleic acid of a cell of the cellular sample indicates that the level (or relative level) of the target nucleic acid is equal to or less than the level (or relative level) known to be associated with an aberrant cell, then the cell of the cellular sample is determined to be aberrant. Therefore, the subject methods can be used to detect and count the number and/or frequency of aberrant cells in a cellular sample. Any identified cell of interest can be isolated for further study.

In some instances, it is unknown whether the expression of a particular target nucleic acid varies in aberrant cells and the methods of the invention can be used to determine whether expression of the target nucleic varies in aberrant cells. For example, a cellular sample known to contain no aberrant cells can be evaluated and the results can be compared to an evaluation of a cellular sample known (or suspected) to contain aberrant cells.

In some instances, an aberrant cell is a cell in an aberrant state (e.g., aberrant metabolic state; state of stimulation; state of signaling; state of disease; e.g., cell proliferative disease, cancer; etc.). In some instances, an aberrant cell is a cell that contains a prokaryotic, eukaryotic, or viral pathogen. In some cases, an aberrant pathogen-containing cell (i.e., an infected cell) expresses a pathogenic mRNA or a host cell mRNA at a level above cells that are not infected. In some cases, such a cell expresses a host cell mRNA at a level below cells that are not infected.

In embodiments that employ a flow cytometer to flow cytometrically analyze the cellular sample, evaluation of cells of the cellular sample for the presence of a target nucleic acid can be accomplished quickly, cells can be sorted, and large numbers of cells can be evaluated. Gating can be used to evaluate a selected subset of cells of the cellular sample (e.g., cells within a particular range of morphologies, e.g., forward and side-scattering characteristics; cells that express a particular combination of surface proteins; cells that express particular surface proteins at particular levels; etc.) for the presence or the level (or relative level) of expression of a target nucleic acid.

In some embodiments, the methods are methods of determining whether an aberrant cell is present in a diagnostic cellular sample. In other words, the sample has been obtained from or derived from an in vivo source (i.e., a living multi-cellular organism, e.g., mammal) to determine the presence of a target nucleic acid in one or more aberrant cells in order to make a diagnosis (i.e., diagnose a disease or condition). Accordingly, the methods are diagnostic methods. As the methods are "diagnostic methods," they are methods that diagnose (i.e., determine the presence or absence of) a disease (e.g., cancer, circulating tumor cell(s), minimal residual disease (MRD), a cellular proliferative disease state, viral infection, e.g., HIV, etc.) or condition (e.g., presence of a pathogen) in a living organism, such as a mammal (e.g., a human). As such, certain embodiments of the present disclosure are methods that are employed to determine whether a living subject has a given disease or condition (e.g., cancer, circulating tumor cell(s), minimal residual disease (MRD), a cellular proliferative disease state, a viral infection, presence of a pathogen, etc.). "Diagnostic methods" also include methods that determine the severity or state of a given disease or condition based on the level (or relative level) of expression of at least one target nucleic acid.

In some embodiments, the methods are methods of determining whether an aberrant cell is present in a non-diagnostic cellular sample. A non-diagnostic cellular sample is a cellular sample that has been obtained from or derived from any in vitro or in vivo source, including a living multi-cellular organism (e.g., mammal), but not in order to make a diagnosis. In other words, the sample has been obtained to determine the presence of a target nucleic acid, but not in order to diagnose a disease or condition. Accordingly, such methods are non-diagnostic methods.

Compositions and Kits

Also provided are reagents, compositions and kits thereof for practicing one or more of the above-described methods. The subject reagents, compositions and kits thereof may vary greatly and can include any of: a fixed, permeablized, and rehydrated cellular sample (e.g., including a nuclease inhibitor, e.g., a RNase inhibitor); a probe set for detecting a target nucleic acid; a cellular fixation reagent; a cellular permeabilization reagent; an aqueous cellular post-fixation reagent; a nuclease inhibitor (e.g., an RNase inhibitor); a nucleic acid detection agent or reagent (e.g., a nucleic acid detection agent including a signal producing system that includes a labeled nucleic acid probe); a signal amplification component (e.g., a branched nucleic acid); a protein detection reagent (e.g., an antibody or a or binding fragment thereof); buffers appropriate for sample stabilization, dilution, storage (i.e., storage buffer), washes (i.e., wash buffer), and/or dissolution; a stimulating agent (e.g., a stimulator); etc. The various components of the reagents, compositions and kits may be present in separate containers, or some or all of them may be pre-combined into a single reagent mixture or single container.

In some embodiments, a composition includes a fixed, permeablized, and rehydrated cellular sample with a nuclease inhibitor (e.g., an RNase inhibitor). In some instances, the composition further includes a protein detection reagent (see above), a stimulating agent, and/or a nucleic acid detection agent (see above).

In some embodiments, a kit includes a cellular fixation reagent, a cellular permeabilization reagent, an aqueous cellular post-fixation reagent; and a nuclease inhibitor (e.g., an RNase inhibitor). In some instances, the kit further includes a protein detection reagent (see above), a stimulating agent, a nucleic acid detection agent (see above), and/or a buffer.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. In addition, common laboratory protocol abbreviations may be used (e.g., hr=hours, min=minutes, ml=milliliters, ul=microliters, rpm=revolutions per minute, g (in the context of centrifugation)=times the force of gravity, etc.).

Example 1

A single cell RNA flow (SCRF) methodology is presented that allows sensitive multiplexed co-detection of protein-based markers along with mRNA transcripts at a concentration of as few as one copy (e.g., as few as 5 copies, as few as 10 copies, as few as 15 copies, etc.) per cell.

Materials and Methods

Primary Cells and Cell Lines

Human U937 cells were cultured in RPMI supplemented with 10% fetal calf serum (FCS). For stimulations, cells were incubated in culture medium supplemented with 50 ng/ml of phorbol myristate acetate (PMA) for 24 hours. The B16 melanoma cell line stably transfected with mouse FMS-like tyrosine kinase 3 ligand (Flt3L) was a kind gift from Dr. Edgar Engleman, Stanford University. Flt3L-conditioned media was harvested from these B16 melanoma cells after 3-5 days culture in RPMI 1640 supplemented with 10% FCS, antibiotics, β-mercaptoethanol, and stored at −20° C. Concentration was determined by enzyme linked immunosorbent assay (ELISA) (antibody pairs purchased from R&D Systems). Primary bone marrow cells were collected from femur, tibia, pelvis, and spine of 5-10 week-old female BALB/c mice obtained from The Jackson Laboratory. All animal studies were done in compliance with the Stanford Administrative Panel on Laboratory Animal Care Protocol 15986.

Isolation of Splenocytes and Bone Marrow Cells; Generation of Bone Marrow-Derived Flt3L Dendritic Cells Splenocytes were isolated by dispersing the spleen through a 70-µm cell strainer with the plunger from a 3-mL syringe in ice cold Hank's Balanced Salt Solution (HBSS, Gibco). Red blood cells were lysed with ACK lysis buffer (150 mM NH4Cl, 1 mM KHCO3, 100 uM EDTA in PBS), washed twice, then resuspended in RPMI 1640 supplemented with 10% FCS, antibiotics, and β-mercaptoethanol. Bone marrow cells cultured with Flt3L (FLDCs) were prepared by crushing and flushing the femur, tibia, pelvis, and spine, using a 5-mL syringe tip, pouring the single cell suspension through a 70-um cell strainer, lysing red blood cells with ACK lysis buffer, washing twice, then resuspending at $1.5 \times 10^6$ cells/mL in RPMI 1640 supplemented with 10% FCS, antibiotics, β-mercaptoethanol, and 15 ng/mL Flt3L (from conditioned media) for 8 days.

DC Enrichment, CpG Stimulation, and Cytokine Staining

Whole bone marrow or splenocytes were isolated as described above, and then enriched with Miltenyi Biotec's Plasmacytoid Dendritic Cell Kit II. Dendritic cells (DCs) were stimulated at $10^5$ cells/mL, and whole splenocytes were stimulated at $10^7$ cells/mL at 1 µM final concentration of CpG-A 2216 (Invivogen). FLDCs were stimulated at $1.5 \times 10^6$ cells/mL with 1 µM final concentration of CpG-A 2336 (Invivogen) for 9-11 hours at 37° C.; Brefeldin A (Ebioscience) was added after 5-7 hours. After stimulation, cells were pelleted, dead cells were stained with Live/Dead Aqua (Invitrogen), and cells were fixed/permeabilized with Ebioscience's Foxp3 kit. Cells were then stained with IgM-biotin, B220-PeCy7, CD11b-PercpCy5.5 (BD Biosciences), 120g8-PE, IFNα-FITC (clone RMMA-1, PBL Interferon Source), and TNF-700 (BD Biosciences) for 30 minutes on ice, followed by a streptavidin-Qdot605 (Invitrogen).

SCRF (Single Cell RNA Flow) Protocol

When necessary, live cells were pre-stained for 30 min on ice with an antibody mix in PBS supplemented with 0.5% BSA or in RPMI supplemented with 2% FCS. After staining, cells were washed twice with PBS, 0.5% BSA and fixed for 10-20 min at room temperature by adding formaldehyde up to final 4% directly to the staining medium. When antibody pre-staining was not performed, cells were fixed directly by adding formaldehyde up to final 4% directly to the culture medium. Following fixation, fixed cells were pelleted by centrifugation at 600 g for 5 min and resuspended in at least 10 ul residual volume by vortexing. Cells were placed on ice and permeabilized by incubation in more than 20 residual volumes of ice-cold methanol for 10 min. Following permeabilization, cells were stored at −80° C. in methanol.

Figure 13:
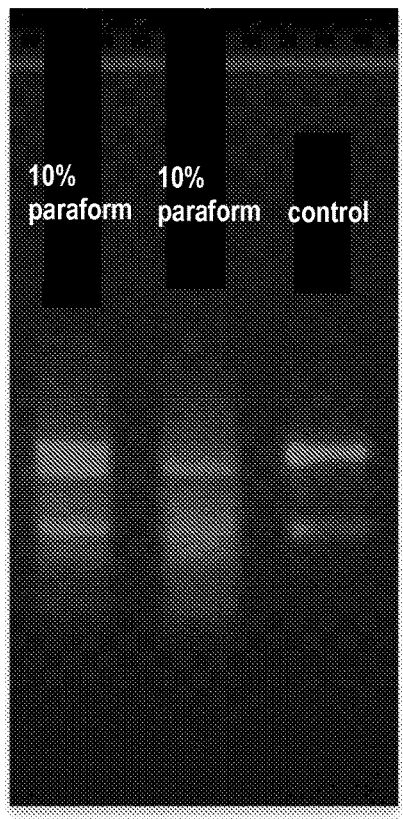
FIG. 13 Postfixation allows preservation of RNA in fixed and permeabilized cells (A) U937 cell line RNA was purified by Trizol from fresh cells (right lane) or by RecoverALL kit (Ambion) from fixed, permeabilized and post-fixed cells (see protocol in Materials and Methods section) and were analyzed on an 1.5% agarose gel (lanes 1-3). Either 4% or 10% formaldehyde in PBST was used for post-fixation (middle and left lane). Skipping the postfixation step resulted in full degradation of RNA (not shown). (B) Live human monocytes (CD33+) were sorted from PBMCs of normal donor 1 (ND1) and ND2. RNA from live ND1 monocytes was prepared using Trizol reagent. ND2 monocytes were fixed, permeablized and postfixed. RNA from ND2 monocytes was prepared by RecoverALL kit (Ambion). Microarray hybridization probes were synthesized from total RNA using an Ovation Pico WTA kit (NuGEN) and were biotin labeled using the Encore Biotin Module (NuGEN). Affymetrix microarrays U133 Plus2 were used to determine levels of gene expression in RNA from live and fixed cells. High correlation between the gene expression values in fixed and permeabilized ND2 (y-axis) versus live (x-axis) ND1 monocytes were observed by microarray screening.
Figure 13:
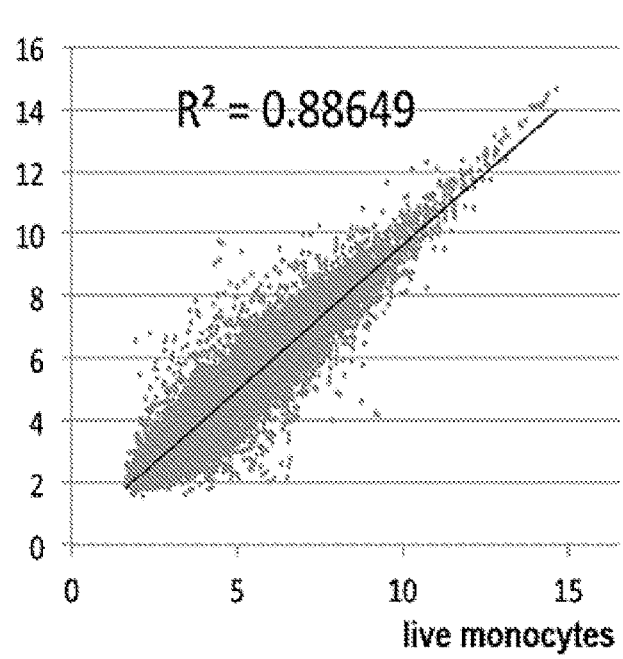

Before the hybridization, cells were pelleted at 600 g for 5 min (all subsequent spins were at this speed and duration), thoroughly vortexed in the residual volume, and post-fixed as follows: First, cells were resuspended and incubated for 5 min in an ice-cold 1:1 methanol/4% formaldehyde in PBS, 0.1% Tween 20 (PBST). Cells were then pelleted again and resuspended in 4% formaldehyde in PBST (For the post-fixation step, either 4% or 10% formaldehyde in PBST was used, see FIG. 13). Following a 20 min incubation with rotation at room temperature, cells were pelleted and washed twice with PBST and 1 U/ml RNasin. Finally, cells were resuspended in 1 volume of PBST and 3 volumes of Protease Stop Buffer (Affymetrix QuantiGene ViewRNA kit). Cells were split into aliquots (up to 5 million cells per 60 µl) and placed into hybridization tubes.

Hybridizations were performed according to instructions supplied with the QuantiGene ViewRNA kit. Briefly, 1.2 µl of probe in 60 µl of Probe-Diluent were added to each tube. Samples were incubated either 3 hours or overnight at 40° C. with shaking. Hybridizations were then spun and all but 30 µl of supernatant was removed. Cells were washed three times with 150 µl of Affymetrix Wash Buffer, each time leaving 30 µl of volume. After the last wash, 30 µl PreHybridization buffer, 1.2 µl Pre-Amplifier, and 28.8 µl Amplifier Diluent were added to the 30 µl of cells. After 2 hours at 40° C., 200 µl of Affymetrix Wash Buffer was added. After the solution was mixed thoroughly, cells were spun, and supernatant was removed except for 30 µl. Cells were washed twice with 150 µl of Affymetrix Wash Buffer, each time leaving 30 µl liquid. Following the second wash, 30 µl Pre-Hybridization buffer, 1.2 µl Amplifier, and 28.8 µl Amplifier Diluent were added to the 30 µl of cells. After 2 hours of hybridization at 40° C., 200 µl of Affymetrix Wash Buffer were added straight to the hybridization mixtures. After the solution was mixed thoroughly, cells were spun, and the supernatant was removed leaving 30 µl of residual volume. Cells were washed twice with 150 µl Affymetrix Wash Buffer, each time leaving 30 µl of residual volume. After the last wash, 30 µl Pre-Hybridization buffer, 1.2 µl labeled probe (LP), and 28.8 µl Labeled Probe Diluent were added to the 30 µl of cells. After 2 hours of hybridization at 40° C., samples were spun and all but 30 µl of the hybridization mix was removed. Cells were washed twice with 150 µl Affymetrix Wash Buffer, each time leaving 30 µl of residual volume. If post-staining for protein markers was necessary, the cells were washed once with 150 µl PBST, pelleted, and stained in 100 µl PBST with antibody. Cells were washed twice with PBST and analyzed on an LSRII or a FACSAria (BD Bioscience).

Antibodies Used for Flow Cytometry and Cell Sorting

The following antibodies were purchased from BD Biosciences: pStat3 (pY705), pStat5 (pY694), CD11a, CD36, QDot605-labeled anti-CD45, Pacific Blue-labeled anti-CD3, FITC-labeled anti-CD34, PerCP-Cy5.5-labeled anti-CD33. Purified CD321 was purchased from eBiosciences. Conjugation of NHS-Ax488 and NHS-Ax647 dyes (Invitrogen) to purified antibodies was performed using protocols supplied by manufacturer. For sorting of blast cells, fixed, permeabilized, stained PBMCs were gated as $SSC^{medium-high}$, $CD45^{medium}$, $CD3^{negative}$. Signaling subsets were sorted from gated blast cells based on pStat5 and pStat3 staining. CD3-positive T cells were sorted for RNA quality control.

Three Different Optional Steps (1) Prior to fixation, live cells can be contacted with an antibody that specifically binds a surface marker (A labeled antibody can be used as long as the label and antibody resist the subsequent methanol treatment). To do this, live cells are contacted with ice cold antibody solution for 30 minutes. The antibody solution contains the antibody diluted in either (i) phosphate buffered saline (PBS) supplemented with 0.5% bovine serum albumin (BSA) or (ii) RPMI supplemented with 2% fetal calf serum (FCS). After contact with the antibody solution, the cells are washed twice with same solution (minus the antibody). Proceed to Fixation step.

(2) After fixation and prior to permeabilization, cells can be contacted with an antibody that specifically binds a cellular protein (A labeled antibody can be used as long as the label and antibody resist the subsequent methanol treatment). To do this, fixed cells are pelleted by centrifugation at 600 g for 5 minutes. Cells are then be re-suspended in residual volume by vortexing. Cells are contacted with a solution of 0.1% Saponin and 4% formaldehyde in PBS for 10 minutes at room temperature. Cell are centrifuged, followed by 3 washes in a solution of 0.1% Saponin and RNas inhibitor (1/1000 dilution) in PBS at 4° C. Cells are incubated for 5 minutes at room temperature in staining solution (minus antibody) supplemented with RNase inhibitor (1/50 dilution). Antibody is added and samples are incubated for 30 minutes at 4° C. with periodic shaking. Three quick washes are performed with 1.5 ml of 0.1% Saponin supplemented with RNase inhibitor (1/500 dilution) in PBS. Solution is replaced with 0.1% Saponin supplemented with 4% formaldehyde in PBS for 10 minutes at room temperature. Proceed to permeabilization step.

(3) After the hybridization step used here, and prior to the flow cytometry detection step used here, the cellular sample can be contacted with an antibody that specifically binds a cellular protein. To do this, cells are spun down via centrifugation, and resuspended and incubated in an antibody-containing solution of PBST and RNas inhibitor (diluted 1/100) for 30 minutes at room temperature. Cells are then washed twice with the same solution (minus the antibody). Proceed to flow cytometry step.

Results

Branched DNA Cascades Allow Sensitive Detection of RNA by Flow Cytometry

RNA in situ hybridization is a well-established technique that produces reliable data in adherent cells and whole mount embryos of various organisms. Yet application of this technique in the context of flow cytometry (Mosiman et al. (2000) In Situ Hybridization in Flow Cytometry, G. B. Faguet, Editor, Humana Press Inc.: Totowa, N.J. p. 231-251) is rarely reported. In the course of initial experiments performed in this study extensive RNA degradation was observed when fixed and permeabilized cells were moved to a water phase for subsequent hybridization or antibody-based staining (data not shown). In protocols where RNA in situ hybridization is followed by microscopy this step is preceded by air-drying, which apparently aids in preserving the RNA. The air-drying though is not compatible with flow cytometry. Using cell lines and human PBMCs as models, a protocol was developed to inactivate RNases that remain active in fixed cells. Cells were first fixed and then permeabilized by methanol. Importantly, following the methanol step post-fixation by paraformaldehyde was performed. We have found that this additional fixation step allows recovery of intact RNA from fixed and stained cells. Post-fixation enables the paraformaldehyde based inactivation of RNAses (Jonsson, N. et al. (1959) Histochemie, 1(4): p. 251-256) in underfixed intracellular compartments rendered permeable by methanol treatment. The reliability of this procedure is supported by comparative microarray analysis that shows linear correlation of expression values obtained in live and fixed cells.

A combination of post-fixation based cell pretreatment and "branched DNA" based fluorescent signal amplification (QuantiGene View RNA) (Piotrowska, J., et al., (2010) Journal of virology, 84(7): p. 3654-65; Taylor, A. M., et al., (2009) The Journal of neuroscience, 29(15): p. 4697-707) herein called "SCRF" (Single Cell RNA Flow) was used for cytometric mRNA detection. Branched DNA signal amplification works by exponential build-up of a tree-like detection structure (FIG. 1A) such that every next probe of a cascade generates more templates for the steps to follow. To examine the quantitative performance of the SCRF protocol, a panel of target genes (GAPDH, PPIB, HPRT, POLR2A, HMBS) known to be constitutively expressed at different levels ranging from thousands of copies of transcript per cell (GAPDH) (Bustin, S. A., (2000) Journal of molecular endocrinology, 25(2): p. 169-93; Wilkening, S., et al. (2003) Drug metabolism and disposition: the biological fate of chemicals, 31(8): p. 1035-42) to ten (HPRT, PoIR2A) (Steen, A. M., et al., (1990) Experimental cell research, 186(2): p. 236-44), to fewer (HMBS) was assembled based on literature and database searches (Carter, M. G., et al., (2005) Genome Biology, 6(7): p. R61). For each gene, 10 to 20 short antisense DNA probes incorporating a target-specific regions and a dedicated sequence for proximity-based generation of a landing site for the amplification cascade were synthesized. The detection of transcripts in the panel was performed in U937 human cancer cell line. Branched DNA detection cascades were assembled by four sequential hybridizations of fixed, permeabilized and postfixed U937 cells with detection probes, preamplifier, amplifier and detector labeled with Ax (ALEXA FLUOR®) 647 dye as recommended in QuantiGene View RNA protocol. Application of the full cascade without addition of pre-amplifier probes was used as a control. The hybridized samples were concurrently analyzed by both flow cytometry (FIG. 1B) and microscopy (FIG. 1D). Average number of fluorescent signals per cells was estimated from confocal stacks collected for 100 cells for each type of transcript. As expected from previous studies (Femino, A. M., et al. (2003) Methods in enzymology, 361: p. 245-304; Itzkovitz, S. et al. (2011) Nature Methods, 8(4 Suppl): p. S12-9; Raj, A., et al., (2008) Nature Methods, 5(10): p. 877), the number of fluorescent spots per cell agreed with the number of transcripts per cell calculated based on absolute quantification by qPCR (data not shown) and reports in the literature (Pannetier, C., et al., (1993) Nucleic Acids Research, 21(3): p. 577-83). The distribution of the flow cytometric signal from the least expressed gene HMBS (average 8 transcripts per cell) was clearly different from control where the first step probe was omitted. A linear correspondence between the relative medium fluorescence intensity rMFI (rMFI=MFIgene/MFI-control) and the average number of spots-transcripts per cells was observed, indicating the wide dynamic range of the SCRF detection (FIG. 1C). Considering the ability of flow cytometry to discern the signal with rMFI>2, we estimated that with Ax647 labeled detection cascade the lowest number of transcript detectable by SCRF to be around 5 molecules per cell. Same panel of genes was detected with branched DNA cascades labeled with other fluorophores (Ax 546, Ax488, Ax 750). With all the dyes it was possible to detect the lowest expressed genes yet the best resolution was achieved with Ax647 labeled cascade.

Using SCRF to Map the Expression Domains of Hematopoietic TFs.

Figure 2:
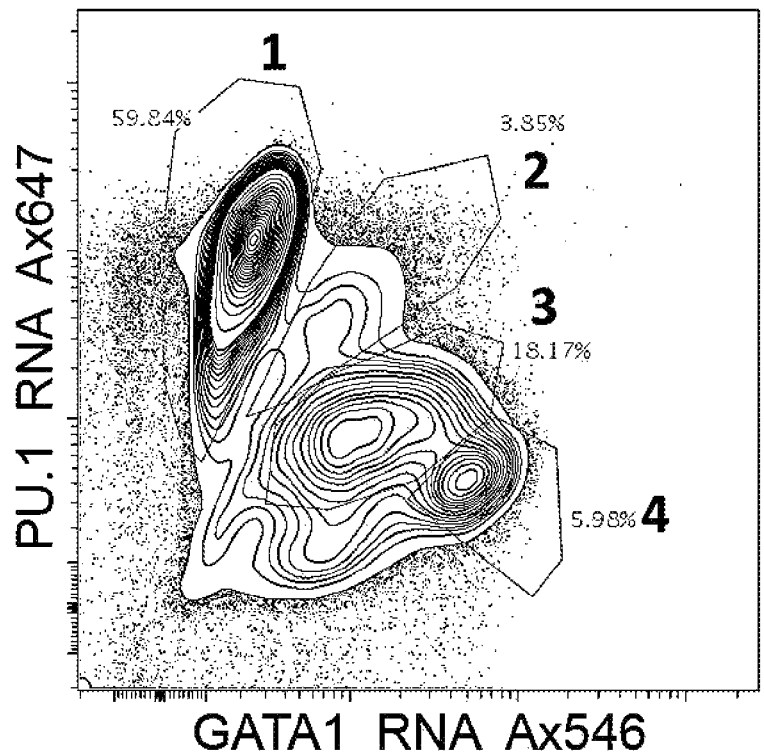
FIG. 2 Co-expression of PU.1 and GATA1 in committed hematopoietic progenitors. (A) lin⁻SCA1⁺cKIT⁺ cells were sorted live from mouse bone marrow cells enriched by lineage depletion. PU.1 and GATA1 were simultaneously detected by SCRF cytometry. (B) Populations marked with numbered gates in Panel A were analyzed by microscopy. Projection of confocal Z-stacks are shown. Blue corresponds to nuclear membrane stained with anti-lamin antibodies conjugated with Ax 488. Red corresponds to GATA1 detected with antibody conjugated to Ax546. Yellow corresponds to PU.1 detected with antibody conjugated to Ax647.
Figure 2:
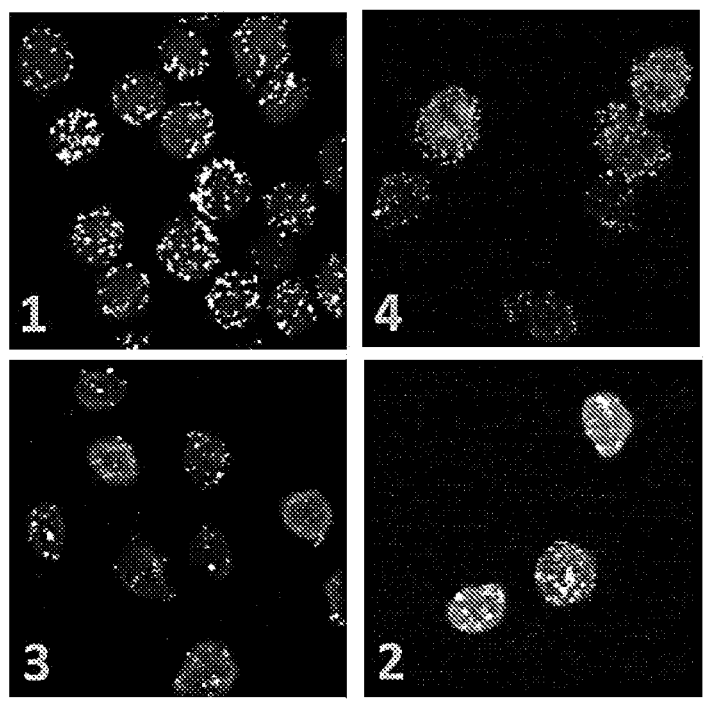
Figure 4:
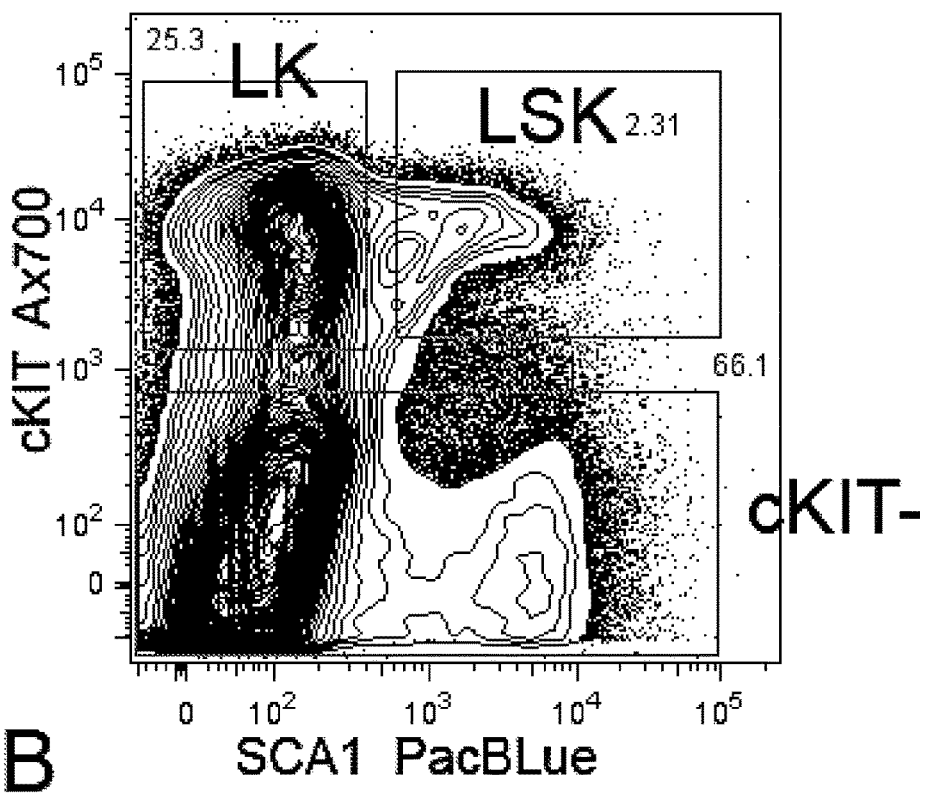
FIG. 4 PU.1 and GATA expression in sorted subsets of lineage depleted mouse bone marrow. A. Population as defined by cKIT and SCA1 staining in lineage negative (lin−) bone marrow cells were enriched by magnetic depletion. B,C,D, Co-expression of PU.1 and GATA1 transcripts in lin−cKIT−, lin−SCA1+cKIT+ (LSK) and lin−SCA1−cKIT+ (LK) subsets sorted from lin− bone marrow and treated according to RNA flow protocol.
Figure 4:
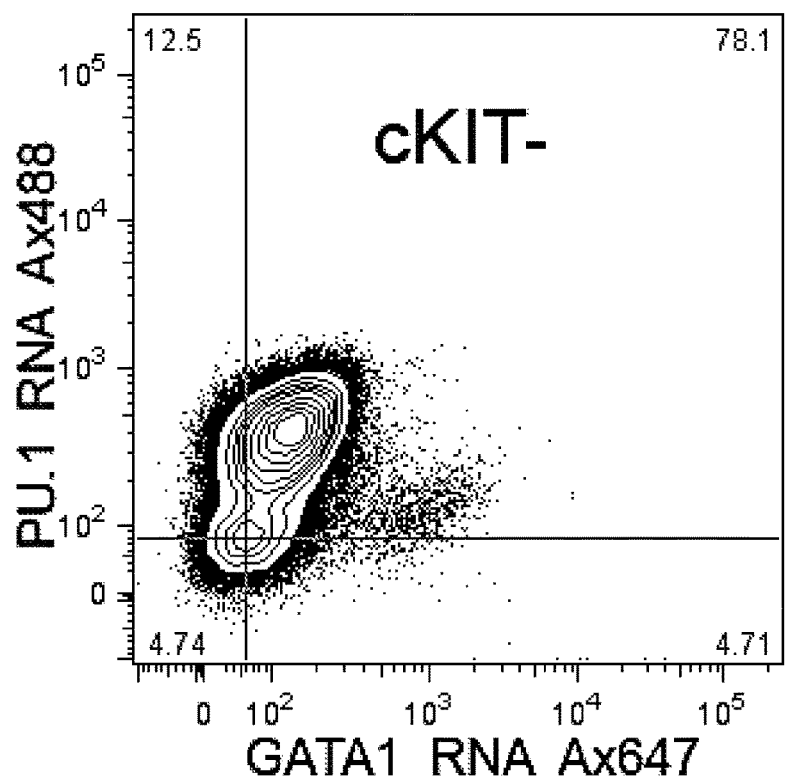
Figure 4:
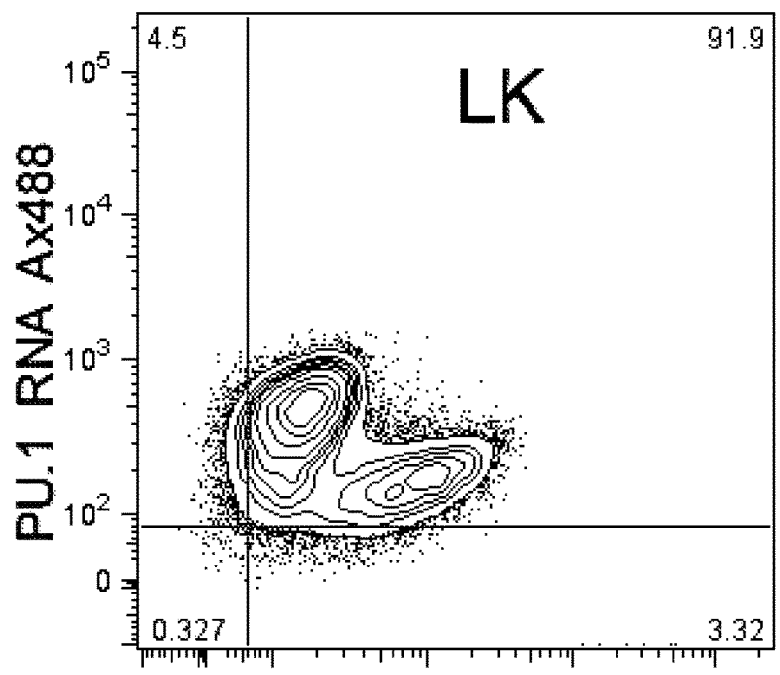
Figure 4:
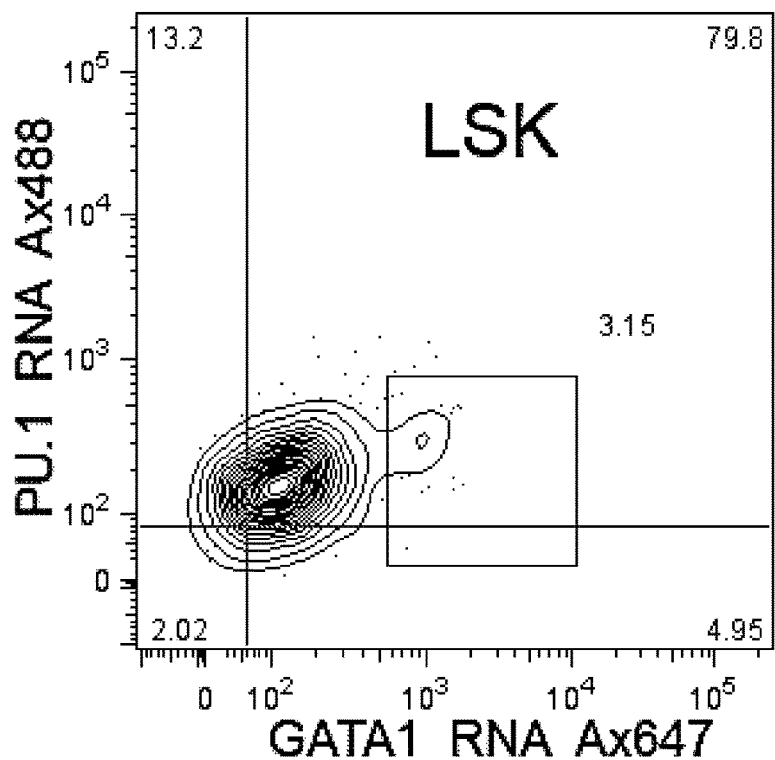

To examine the performance of SCRF for multiplexed transcript detection, subsets of lineage depleted mouse bone marrow were analyzed for PU.1 and GATA1 mRNA expression. These genes encode transcription factors involved in regulation of the early hematopoietic lineage split into common myelo-erythroid and common granulocyte-monocyte-lymphoid progenitors (CMPs and GMLPs, respectively) (Iwasaki, H. et. al. (2007) Oncogene, 26(47): p. 6687-6696). Lineage negative (lin$^-$) bone marrow cells were enriched by magnetic depletion; stained with antibodies against cKIT and SCA1; sorted into lin$^-$cKIT$^-$, lin$^-$SCA1$^+$ cKIT$^+$ (LSK), and lin$^-$SCA1$^-$cKIT$^+$ (LK) subsets (FIG. 4A); fixed; and treated according to the SCRF protocol for simultaneous detection of PU.1 and GATA1 mRNAs with branched DNA cascades labeled with Ax488 and Ax647 accordingly. In concurrence with prior reports (Arinobu, Y., et al (2007) Cell stem cell, 1(4): p. 416-427; Zhang, P., et al., (2000) Blood, October 15; 96(8):2641-8; Nerlov, C., et al. (2000) Blood, April 15; 95(8):2543-51; Koschmieder, S., et al. (2005) International journal of hematology, 81(5): p. 368-377), we observed an overall opposing pattern of PU.1 and GATA1 expression in LK cells (FIG. 4C, long identified as committed hematopoietic progenitors (Akashi, K., et al., (2000) Nature, 404(6774): p. 193-7). The LSK cells, which generally are believed to include mouse hematopoietic stem cells (Osawa, M., et al., (1996) Science, 273(5272): p. 242-5; Spangrude, G. J. et al. (1998) Science, 241(4861): p. 58-62) showed co-expression of low levels of PU.1 and GATA1 mRNA (FIG. 4D). Such co-expression of master regulators opposing lineages is thought to represent so-called "multilineage priming" phenomenon (Miyamoto, T., et al. (2002) Developmental cell, 3(1): p. 137-147; Miyamoto, T. et al. (2005) International journal of hematology, 81(5): p. 361-367; Laslo, P., et al., (2006) Cell, 126(4): p. 755-766). A small subset of LSK cells exhibited high levels of GATA1 expression (FIG. 4D, blue gate), in agreement with a previous analysis demonstrating that these cells are CMPs (Arinobu, Y., et al (2007) Cell stem cell, 1(4): p. 416-427). To further co-examine PU.1 and GATA1 expression in LK subsets by microscopy in a separate experiment expression PU.1 and GATA1 mRNA was detected in sorted LK cells with cascade labeled by Ax647 and Ax546 (a combination of dyes which provided the highest resolution in SCRF). Four distinct sub-populations of LK cells defined by PU.1 and GATA1 mRNA expression (FIG. 2A) were further sorted and examined by confocal microscopy. As expected, cells that expressed high levels of PU.1 exhibited no GATA1 staining (FIG. 2B, panel 1). With the exception of cells that expressed very high levels of GATA1 (about 6% of the LK cells) (FIG. 2B, panel 4), GATA1-expressing cells expressed low levels of PU.1 transcript (FIG. 2B, panel 3). In addition, we detected a small population (4%) that co-expressed the two transcripts at high levels (FIG. 2B, panel 2).

Figure 5:
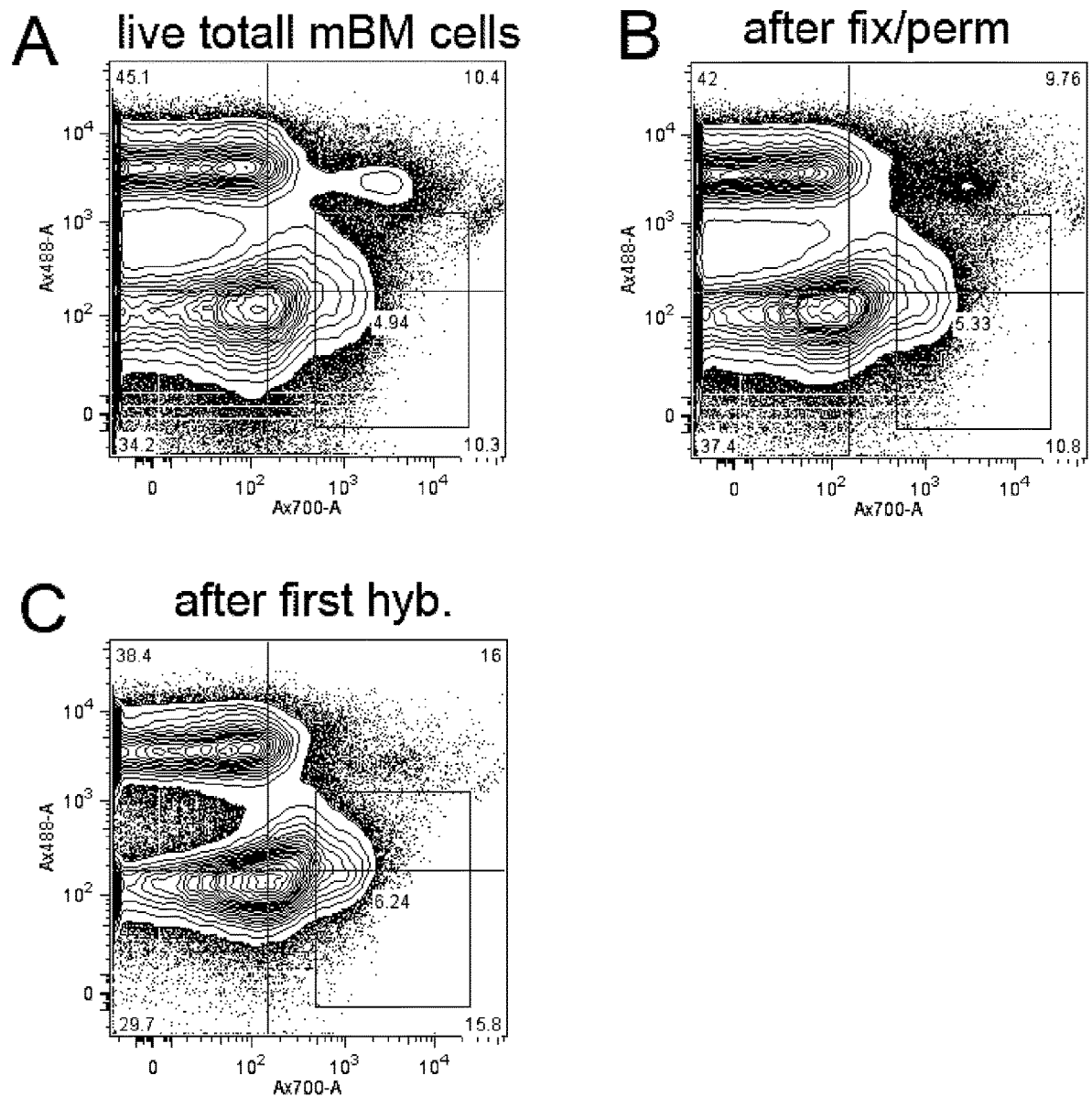
FIG. 5 Resilience of surface staining during the RNA flow hybridizations. Total mouse Bone Marrow was stained live with cocktail of biotinylated lineage antibodies (B220, TCRb, CD3, CD4, Ter119, CD19) followed by staining with streptavidin-Ax488 and CD34-Ax700. The cells were then analyzed by flow cytometry, either immediately (A) after fixation and permeabilization (B) or after first (C), second (D) and forth (E) RNA flow hybridizations. Rectangular gate marks CD34+lin− cells encompassing the population of hematopoietic progenitors. Note the preservation of the CD34 and lineage staining in the course of the protocol.
Figure 5:
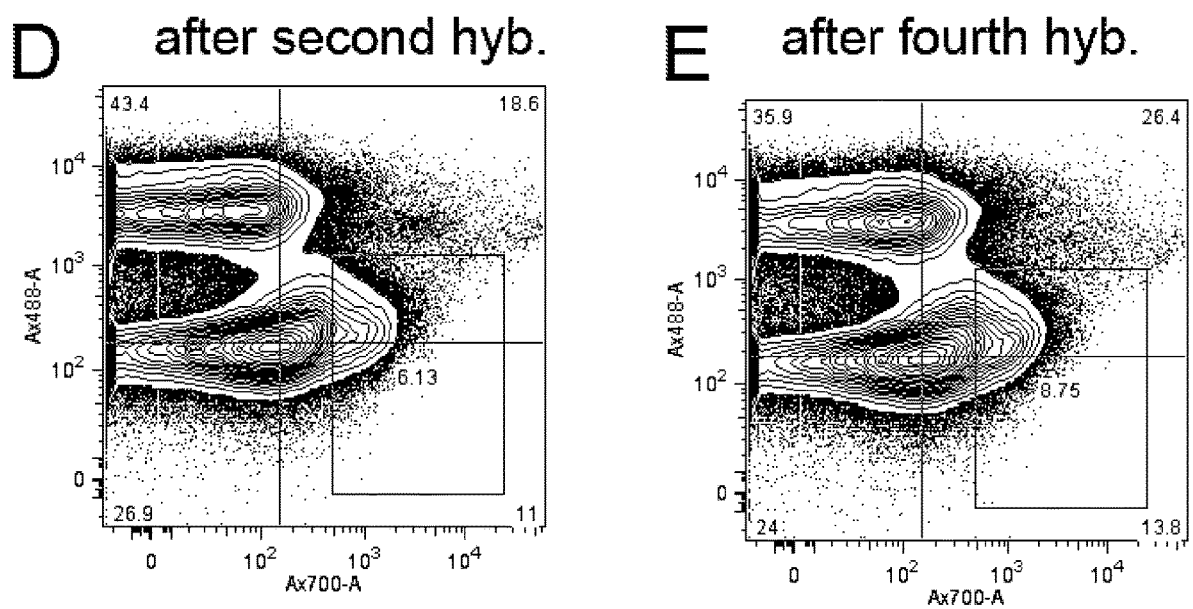
Figure 6:
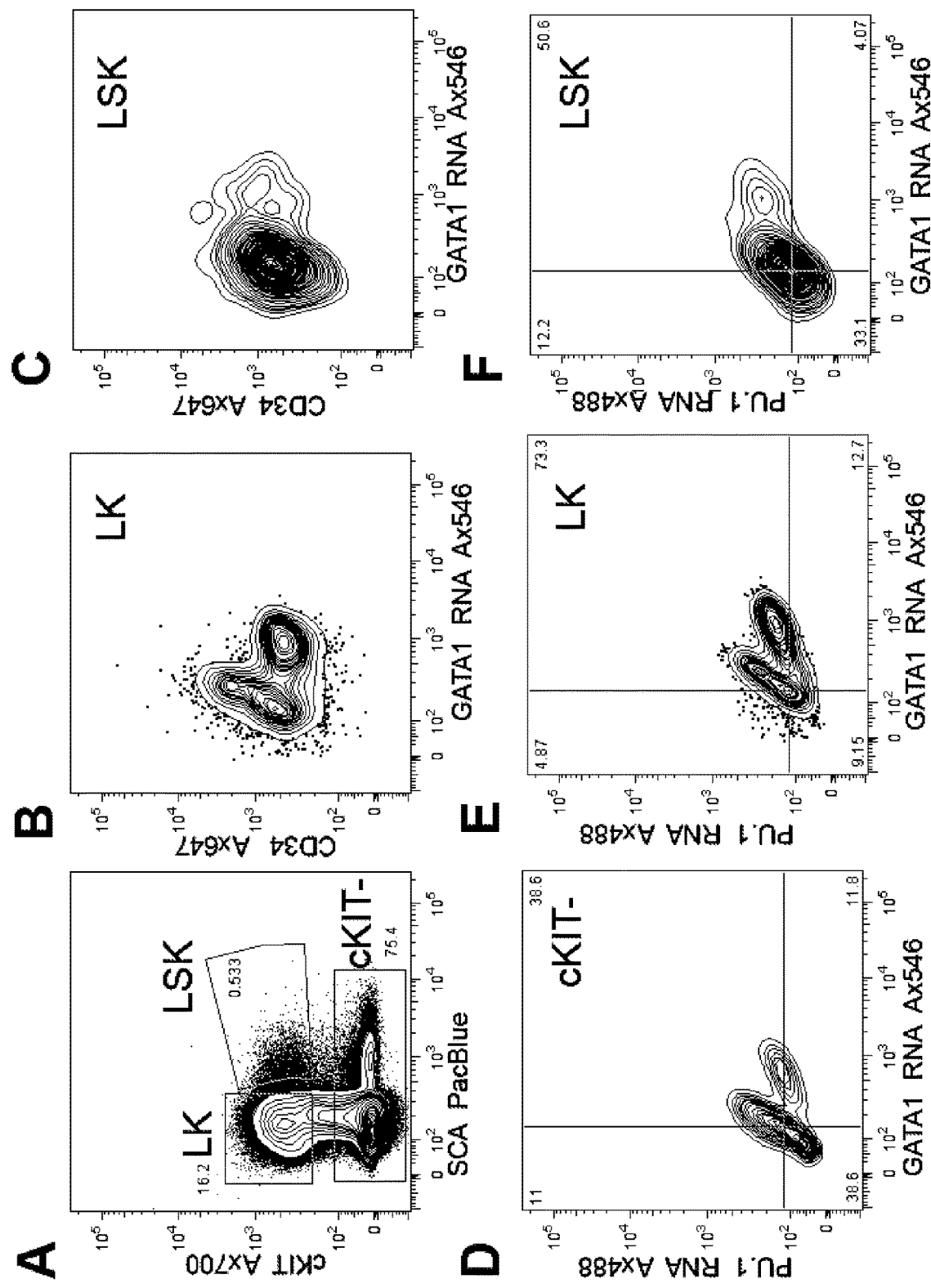
FIG. 6 Co-detection of GATA1 and PU.1 expression in lin− mouse bone marrow subsets as defined by CD34 and Flt3 protein expression. A. lin− subsets defined by surface expression of SCA1 and cKIT protein epitopes. Lineage depleted mouse bone marrow cells were stained live with SCA1, cKIT, CD34 (B,C) or Flt3 (G-L) antibodies and further subjected to RNA flow protocol for the detection of PU.1 and GATA1 transcripts. B,C Gata1 RNA positive cells of the LK and LSK subset do not express CD34. D,E GATA1 and PU.1 are expressed in mutually exclusive patterns in cKIT− and LK subsets of lin− cells. F GATA1 and PU.1 are co-expressed in LSK cells. G-I Flt3 high cells manifest broad range of PU.1 expression. J-L GATA1 transcript and Flt3 are expressed in mutually exclusive patterns in all subsets of lin– cells.
Figure 6:
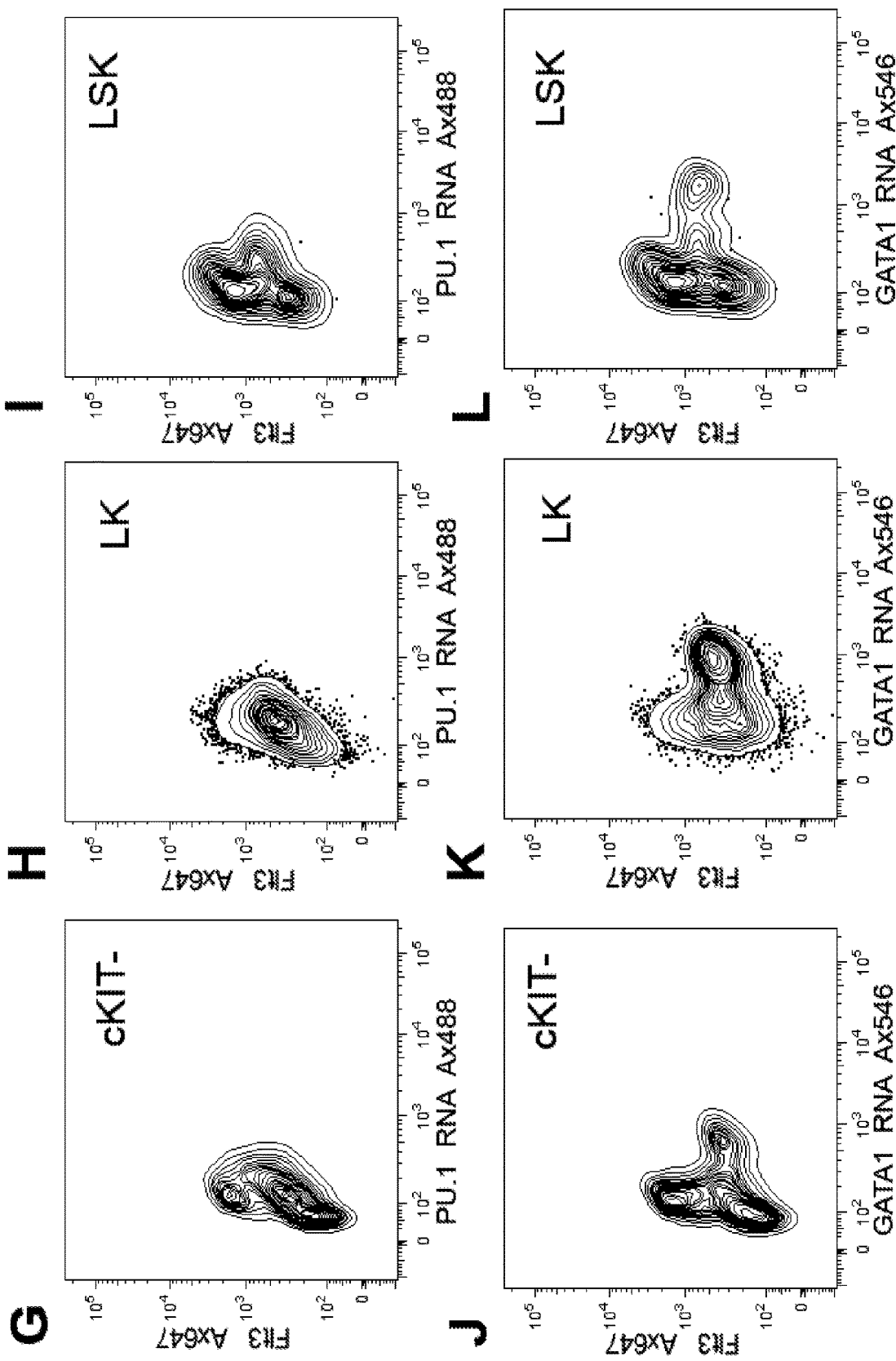
Figure 7:
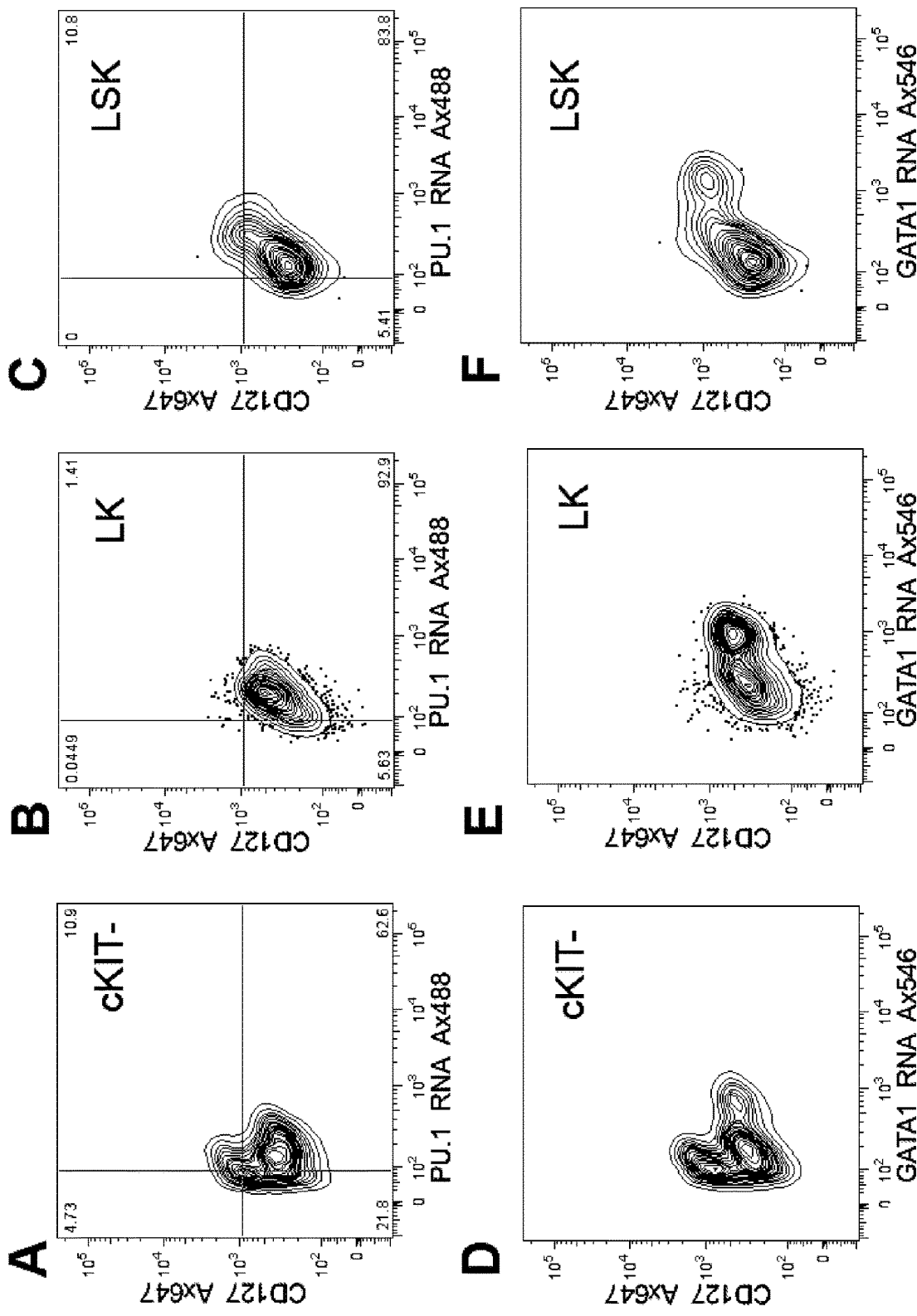
FIG. 7 Co-detection of GATA1 and PU.1 expression in lin– mouse bone marrow subsets as defined by CD127 and FcgammaR protein expression. A-C. Expression of PU.1 transcript in cellular subsets defined by CD127 levels. Majority of CD127 positive cells (containing the commonly defined CLP) are in cKIT– population. Notably PU.1 high cells of LSK subset (combining both myeloid and lymphoid potential) produce elevated levels of CD127, due to "priming" phenomenon. D-F. Expression of GATA1 transcript in cellular subsets defined by CD127 levels. Except for co-expression in a GATA1 high subset of LSK cells GATA1 and CD127 manifest mutually exclusive expression patterns. G-I. Expression of PU.1 transcript in cellular subsets defined by FcgammaR levels. Majority FcgammaR positive cells are in cKIT– population. FcgammaR high cells of the LK subset express high PU.1 matching their function as GMPs. J-L. Expression of GATA1 transcript in cellular subsets defined by FcgammaR levels. GATA1 and FcgammaR manifest largely mutually exclusive expression patterns.
Figure 7:
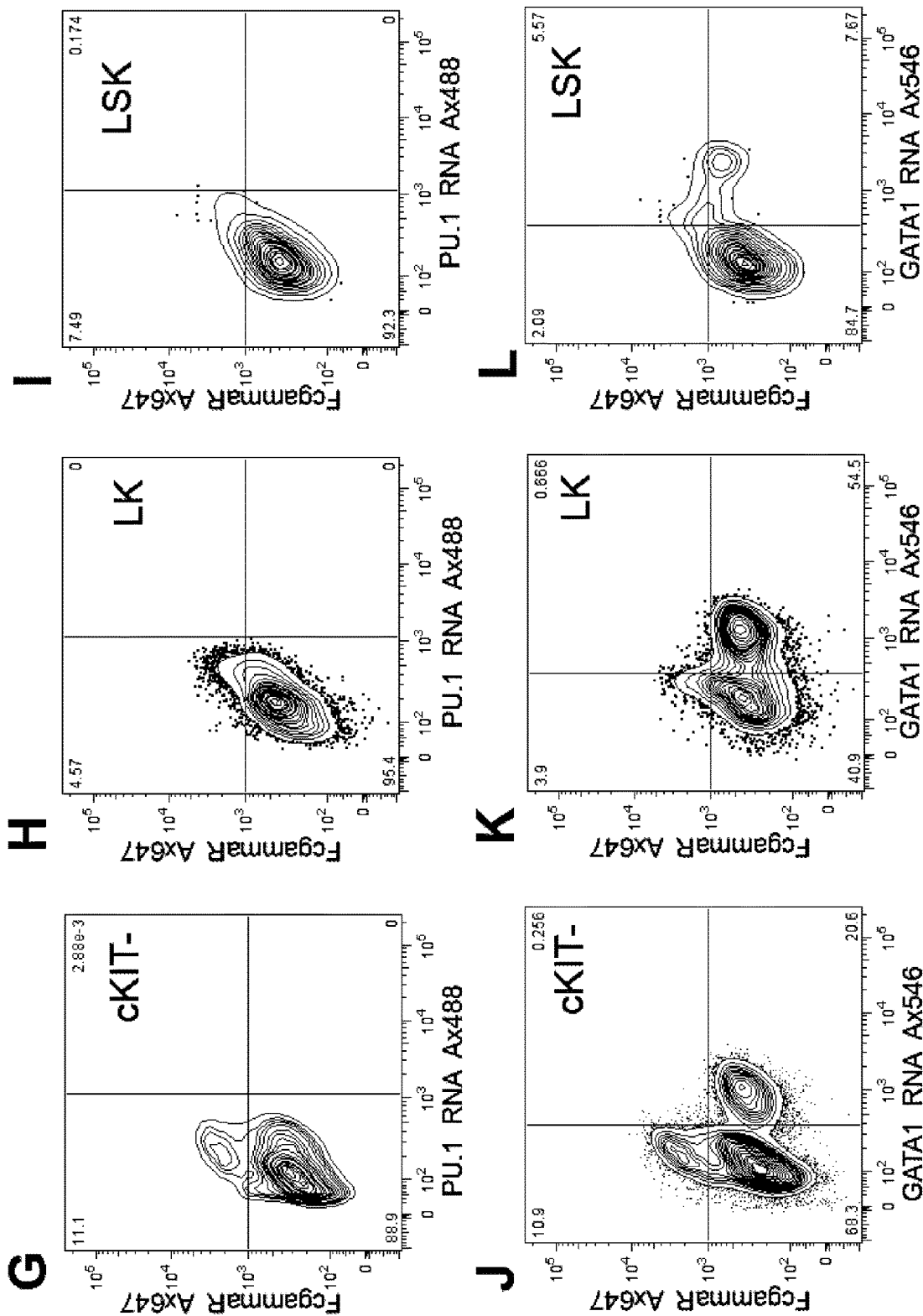
Figure 8:
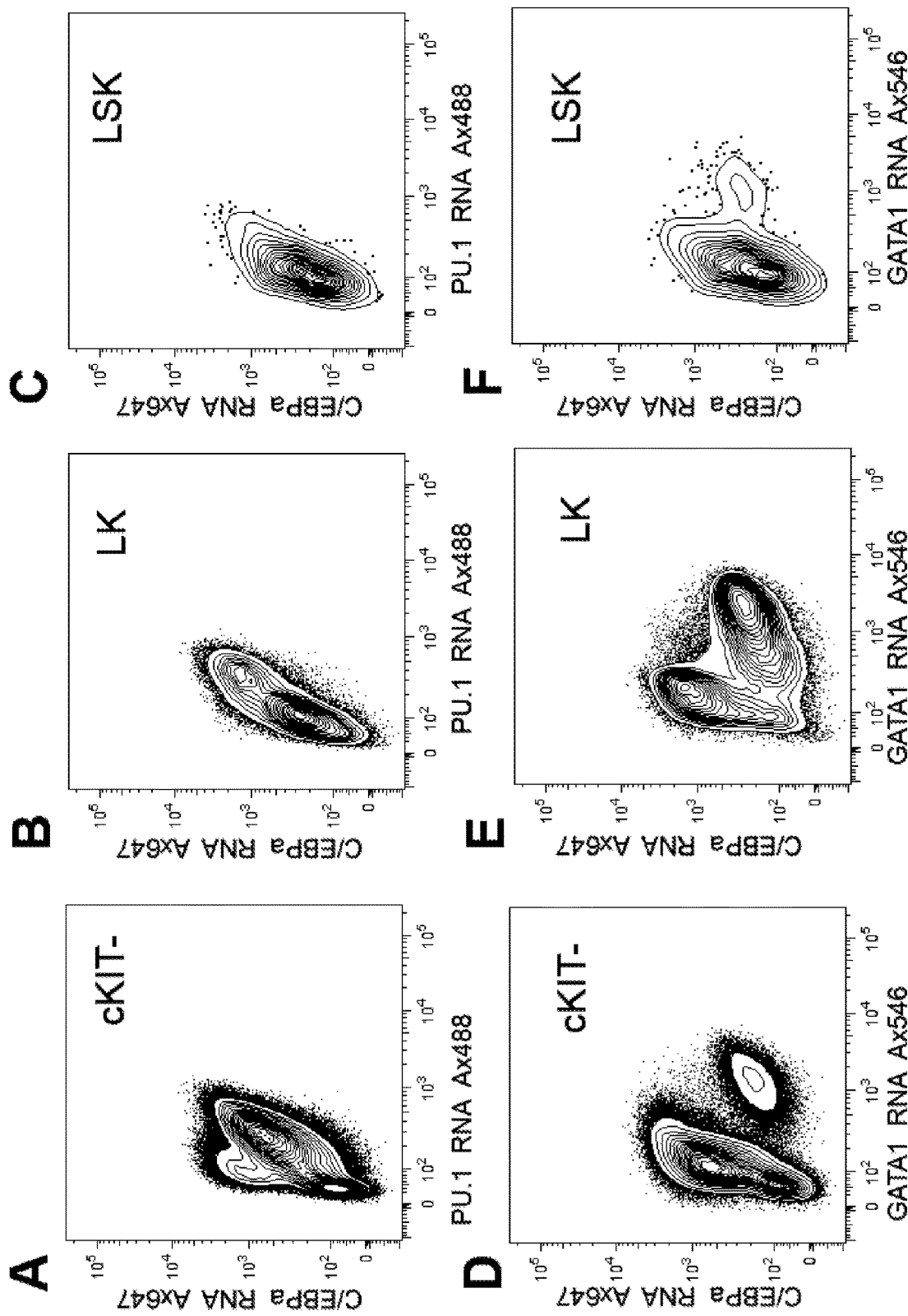
FIG. 8 Co-detection of C/EBPa (A-F) or GFI1B (G-L) with GATA1 (D-F, J-L) and PU.1 (A-C, G-I) expression in lin– mouse bone marrow subsets: cKIT– cells (A,D,G,J), LK cells (B,E,H,K) and LSK cells (C,F,I,L).
Figure 9:
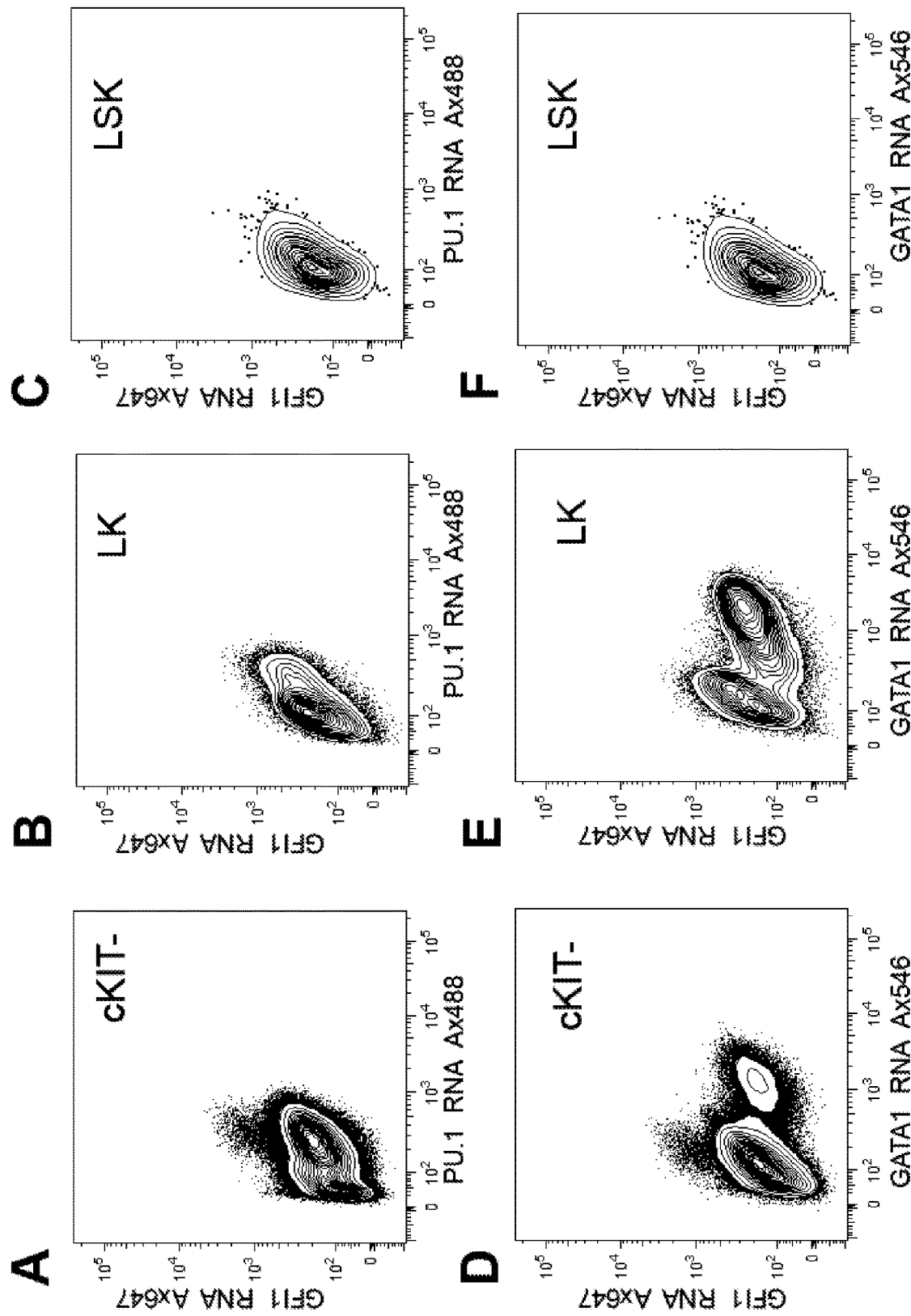
FIG. 9 Co-detection of GFI1 (A-F) or GATA2 (G-L) with GATA1 (D-F, J-L) and PU.1 (A-C, G-I) expression in lin– mouse bone marrow subsets: cKIT– cells (A,D,G,J), LK cells (B,E,H,K) and LSK cells (C,F,I,L).
Figure 10:
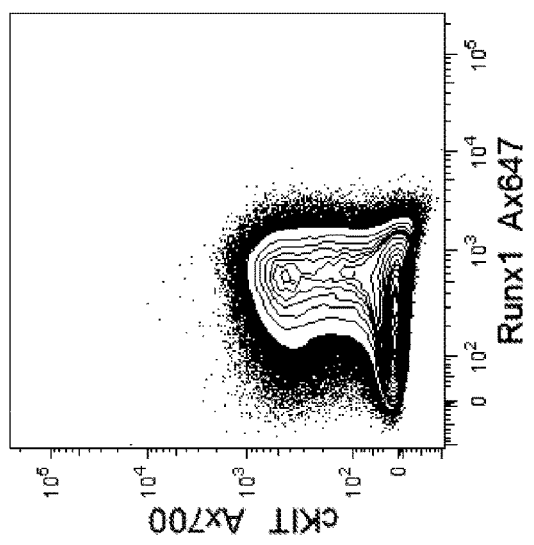
FIG. 10 Co-detection of MEIS1, MYB and Runx1 with GATA1 and PU.1 expression in lin– mouse bone marrow subsets. A-C. Co-expression of MEIS1 and PU.1 in cKIT–, LK and LSK cells. D-F. Co-expression of MEIS1 and GATA1 in cKIT–, LK and LSK cells. G. Background RNA flow signal in lin– cell subsets defined by cKIT levels (no primary probe was supplied during the first step of the RNA flow protocol, the rest of cascade was applied as in RNA flow with specific probes) H-I. Expression of Myb and Runx1 in lin– cell subsets defined by cKIT levels.
Figure 10:
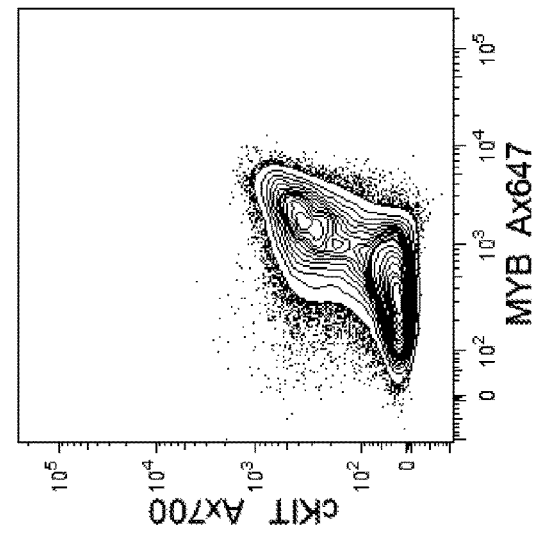
Figure 10:
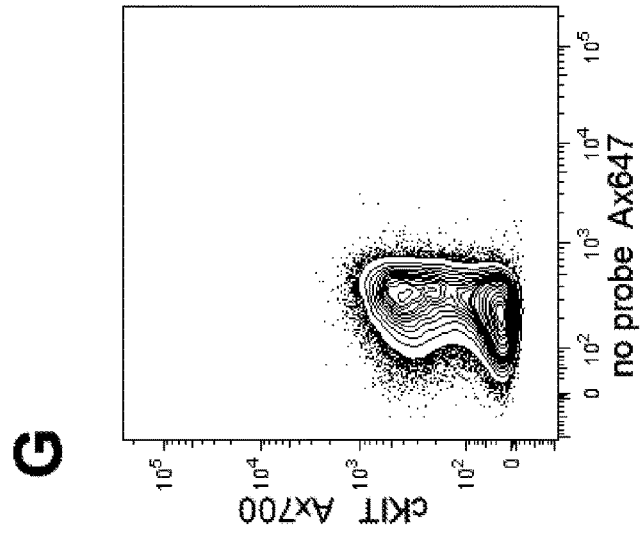

Pre-sorting the populations based on protein staining was not necessary prior to SCRF analysis. Generally, protein staining could be performed at three steps during the protocol. For sensitive epitopes that did not survive the hybridization conditions cells had to be stained live and fixed after staining, in which case the surface staining survived well through the course of several hybridizations (FIG. 5). Otherwise intracellular epitopes could be stained after the post-fixation and before the hybridizations (data not shown) or after the hybridizations (see below). A number of surface markers (FcγRII/III, CD34, CD127, Flt3) used for classic delineation of the branches of early hematopoietic differentiation cascade were detected simultaneously with PU.1 and GATA1 transcripts (FIG. 6, 7) using the prestaining of live lineage depleted bone marrow cells. In contrast to the data obtained with a fluorescent GATA1 reporter, which suggests that 35% of CMPs express GATA1 protein (Arinobu, Y., et al (2007) Cell stem cell, 1(4): p. 416-427), all CD34$^+$ cells in LK populations were found to be GATA1 mRNA negative (FIG. 6B). The Flt3$^{high}$ subset of cKIT$^-$ cells showed intermediate levels of PU.1 (FIG. 6G), consistent with previous data indicating that these cells are common lymphoid progenitors (CLPs) (Arinobu, Y., et al (2007) Cell stem cell, 1(4): p. 416-427). A subset of LSK cells expressed high levels of Flt3 (FIG. 6I), in accordance with early separation of Flt3$^+$ lymphoid-primed multipotent progenitors (LMPP) and Flt3$^-$ CMPs (Adolfsson, J., et al., (2005) Cell, 121(2): p. 295-306). It has been suggested that there is a distinct population of PU.1$^{high}$ cells within the Flt3$^{high}$ subset (Arinobu, Y., et al (2007) Cell stem cell, 1(4): p. 416-427), but no evidence for this population was detected in this analysis. In agreement with prior reports, CD16/32$^{high}$ cells in the LK population expressed the highest levels of PU.1 of the subsets analyzed (FIG. 7H).

A number of RNAs encoding important hematopoietic transcription factors (C/EBP, GFI1, GFI1 b, Pax5, E2A, MEIS, MYB, GATA2) were co-detected with PU.1 and GATA1 transcripts (FIGS. 7-12). There was a strong correlation between PU.1 and C/EBP levels (FIG. 7A-C) and between GATA1 and GFI1b levels (FIG. 7J-L) reflecting a direct regulatory connection (Kummalue, T. et al. (2003) Journal of Leukocyte Biology, 74(3): p. 464-70; Huang, D. Y., et al., (2004) Nucleic Acids Research, 32(13): p. 3935-46). Repression of PU.1 by GFI1 was previously demonstrated (Laslo, P., et al., (2006) Cell, 126(4): p. 755-766; Spooner, C. J., et al., (2009). Immunity, 31(4): p. 576-586), and yet curiously a correlation between PU.1 and GFI1 expression in cKIT$^-$ and LK cells was detected (FIG. 9A, B). Both genes are thought to be activated by C/EBP, therefore such discrepancy is due to a lag between the mRNA and the protein of GFI1 which is sufficient to inhibit PU.1 mRNA expression. Most lin$^-$ cells were Runx2$^{high}$ (FIG. 10I), and LK cells expressed high levels of MYB (FIG. 10H), reflecting the proliferative status of these "progenitor" cells.

Figure 11:
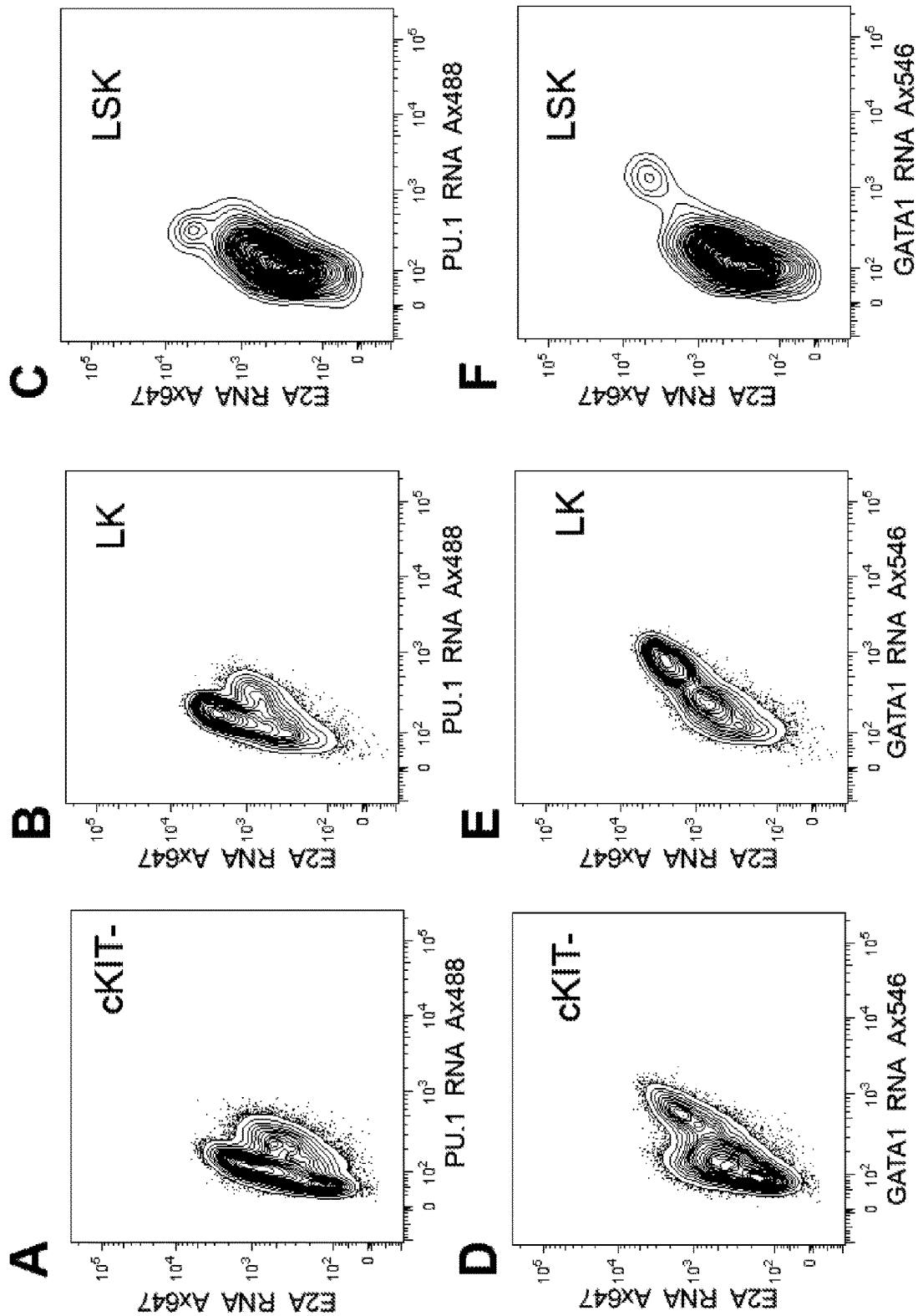
FIG. 11 Co-detection of E2A (A-F) or EBF1 (G-L) with GATA1 (D-F, J-L) and PU.1 (A-C, G-I) expression in lin– mouse bone marrow subsets: cKIT– cells (A,D,G,J), LK cells (B,E,H,K) and LSK cells (C,F,I,L).
Figure 11:
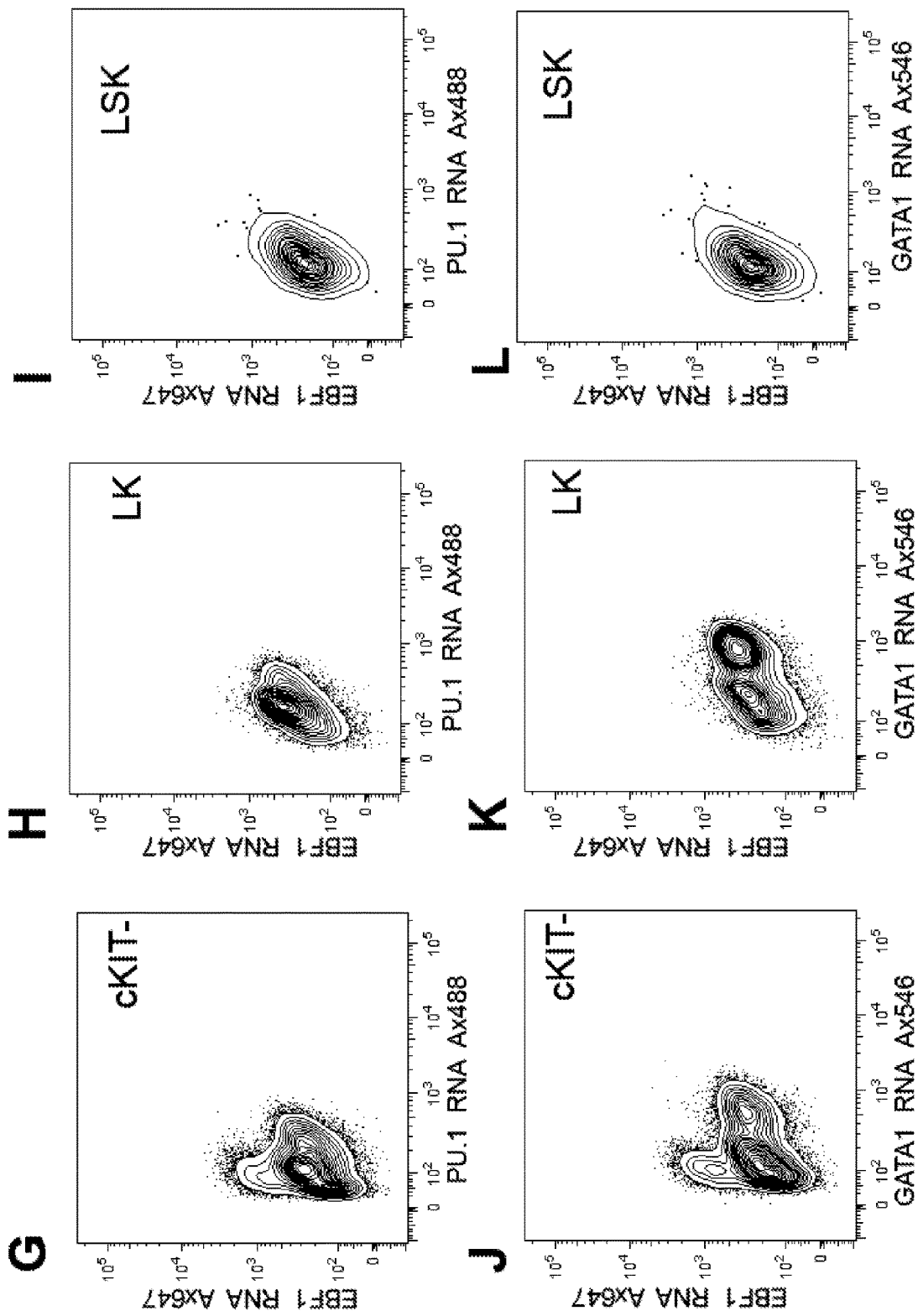
Figure 12:
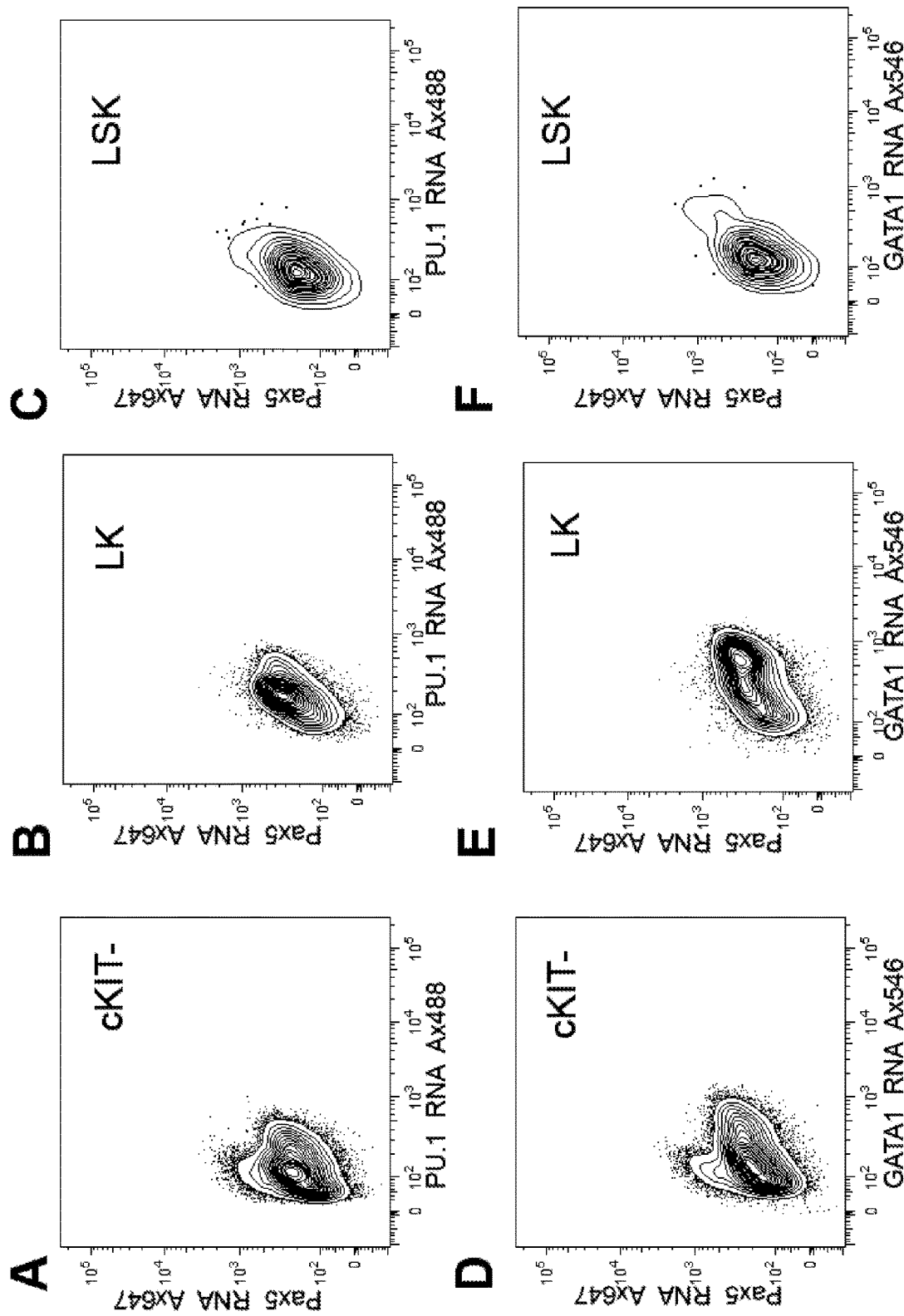
FIG. 12 Co-detection of Pax5 (A-F) or Id2 (G-L) with GATA1 (D-F, J-L) and PU.1 (A-C, G-I) expression in lin– mouse bone marrow subsets: cKIT– cells (A,D,G,J), LK cells (B,E,H,K) and LSK cells (C,F,I,L).

Using the same approach, we evaluated the expression of genes known to be involved in B cell development including EBF1, Id2, Pax5, and E2A/TCF3 (FIG. 11, 12). A positive correlation of E2A levels was observed with levels of both GATA1 and PU.1 expression (FIG. 11A-F), supporting the role of E2A in development of multiple hematopoietic lineages (Lin, Y. C., et al., (2010) Nature Immunology, 11(7): p. 635; Semerad, C. L., et al., (2009) Proceedings Of The National Academy Of Sciences Of The United States Of America, 106(6): p. 1930-5). In concurrence with commonly accepted lineage classification framework, EBF1 and Pax5 were detected in the cells of the cKIT$^-$ population (FIG. 11G-L, 12A-F) with low levels of GATA1 and PU.1 expression (FIG. 5D). In agreement with previous detection in both myeloid (Reizis, B (2010) Current opinion in immunology, 22(2): p. 206-211) and lymphoid (Quong, M. W., et al. (2002) Annual Review Of Immunology, 20: p. 301-22) lineages, Id2 was detected in cKIT$^-$ cells with low levels of GATA1 and intermediate PU.1 expression (FIG. 12G-L)

Using SCRF to Study Cytokine Production by Activated pDC.

Figure 3:
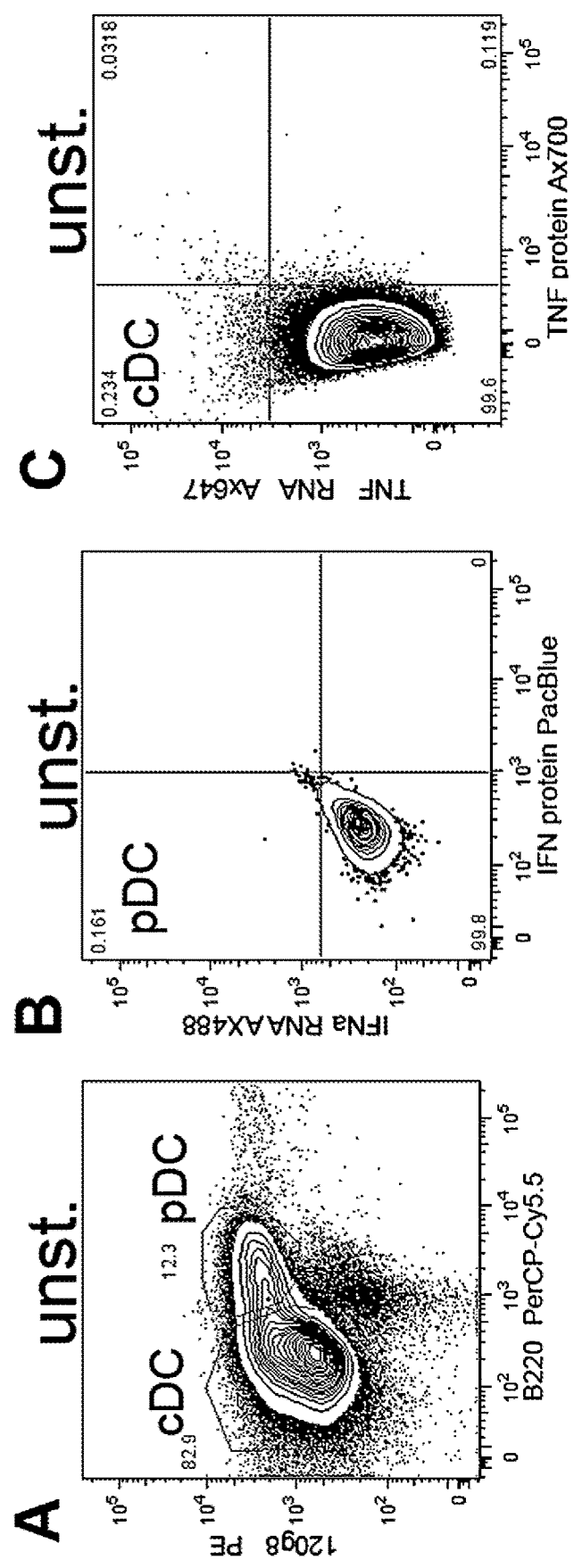
FIG. 3 Stochastic expression of IFNα by PDC. IFNα and TNF expression were measured at RNA and protein levels in unstimulated (A, B, C) FLDCs and in FLDCs stimulated for 11 hours in the presence of CpG (D, E, F). pDCs were identified as the $B220^{high}120g8^{high}$ population (see gating in A and D). IFN and TNF protein and RNA levels were simultaneously measured by SCRF in pDCs (B, E) and the rest of the culture ($B220^{low}$ cells largely correspond to conventional DCs).
Figure 3:
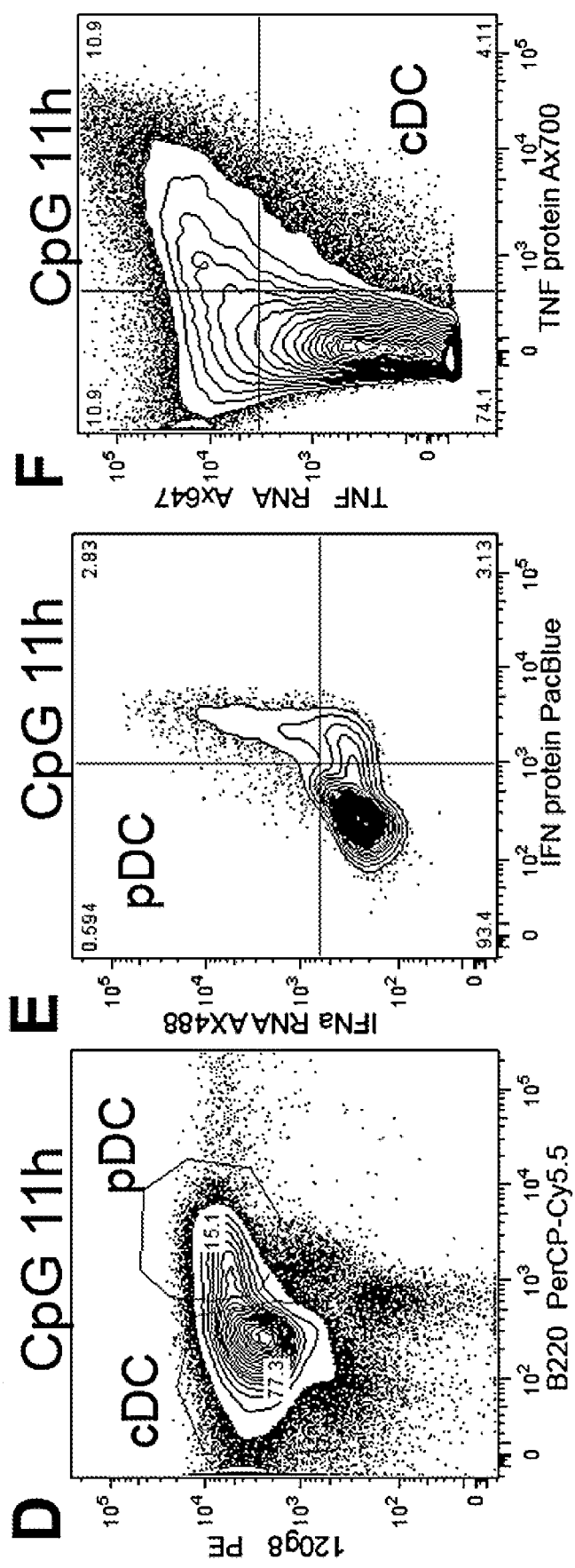
Figure 3:
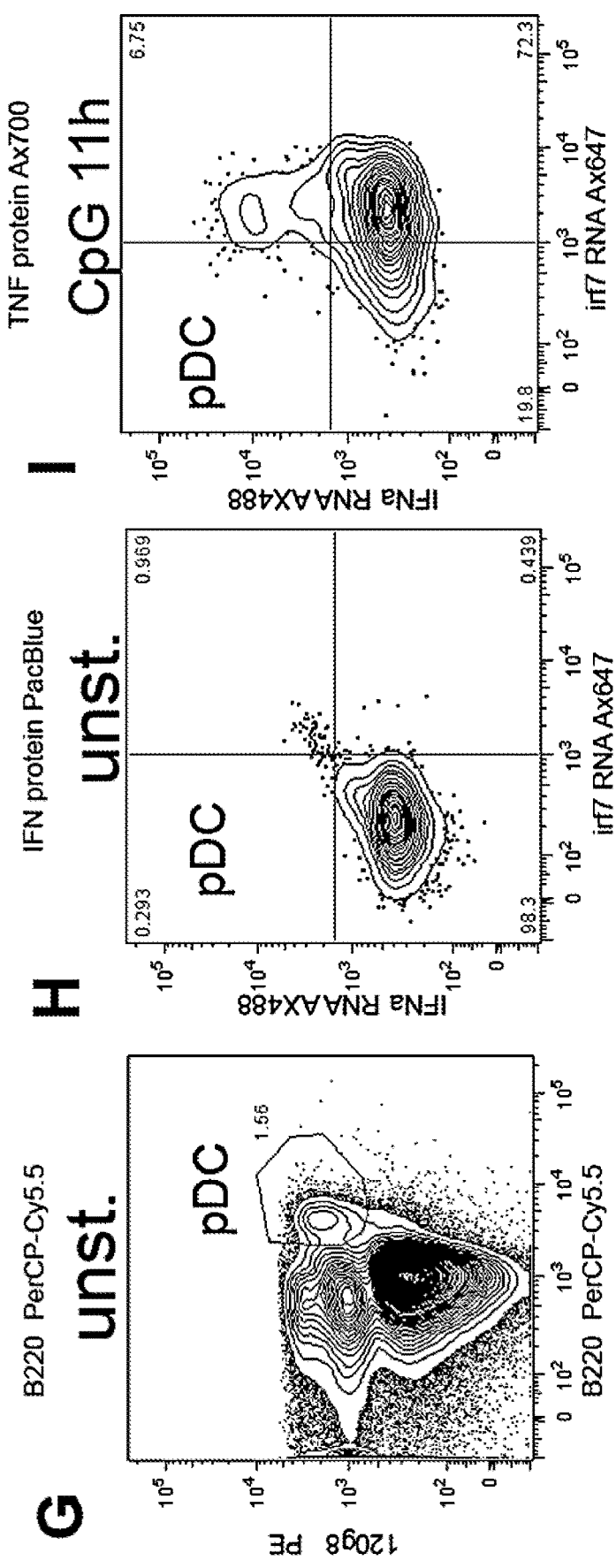

Some protein epitopes lost their antigenicity over the course of the several hybridizations composing the SCRF protocol; however, many proteins were successfully evaluated after SCRF. Staining with antibodies against B220 and 120g8 performed after the SCRF procedure was used to identify the population of plasmacytoid dendritic cells (pDCs) in primary mouse bone marrow as well as in cultures of bone marrow grown in the presence of Flt-3 ligand (FLDC) (FIG. 3A, D, G). Only a subset of pDCs produce type I IFN (Scheu, S., et al. (2008) Proceedings Of The National Academy Of Sciences Of The United States Of America, 105(51): p. 20416-20421; Olshalsky and Fitzgerald-Bocarsly, (2005) Methods Mol Med. 116:183-94.55). Accordingly we found that IFNα was highly expressed at mRNA and protein levels in a fraction of pDCs activated with CpG (FIG. 3E, I), which is commonly used as a mimic of viral infection. TNF mRNA and protein were detected in both pDC (not shown) and non-pDC subsets (FIG. 3F) of activated FLDC cultures.

The IFNα mRNA has a short half-life (Cavalieri, R. L., et al., (1977). Proceedings Of The National Academy Of Sciences Of The United States Of America, 74(10): p. 4415-9), and is the reason that IFNα transcripts were detected in only a portion of cells that expressed IFNα protein (FIG. 3E). In contrast, in all cells in which TNF RNA was detected, TNF was also detected at the protein level (FIG. 3F). Recently several studies have noted the small relative size of a population capable of producing type I IFNs even within a larger population of seemingly homogeneous cells (J Hu, S. I. et al. (2009). Biophysical Journal, 97(7): p. 1984; Jianzhong Hu et al. (2011) PLoS One. February 8; 6(2):e16614; Zhao, M., et al., (2012) PLoS biology, 10(1): p. e1001249). Some reports attribute this phenomenon to general features of basal transcriptional mechanisms implicated in IFN production (J Hu, S. I. et al. (2009). Biophysical Journal, 97(7): p. 1984); one study showed that the heterogeneity of cells with respect to IFN production is largely alleviated upon ectopic overexpression of IRF7 (Zhao, M., et al., (2012) PLoS biology, 10(1): p. e1001249). It has been suggested before that IRF7 is produced at high basal levels in pDCs (Izaguirre, A., et al., (2003) Journal of Leukocyte Biology, 74(6): p. 1125-1138). Using SCRF levels of IRF7 and IFNα transcripts were co-determined in activated bone marrow pDCs. Strong upregulation of IRF7 RNA was detected in all activated pDCs, yet only a subset of cells with high IRF7 levels also expressed IFN RNA (FIG. 3H, I).

Discussion

The single cell RNA flow (SCRF) method described in this study allows flow cytometric multiplexed co-detection, in both immortalized and primary cells, of proteins and mRNA transcripts. Two innovations allowed specific and sensitive detection of mRNA by flow cytometry. The first was the addition of a second fixation after the initial "fixation/permeabilization" steps. This led to a dramatic reduction in the activity of RNases that otherwise would have degraded mRNA and other transcripts when cells are placed in aqueous buffer. The second key is signal amplification by branched DNA cascades. Protein staining can be done before or after mRNA amplification. The SCRF method currently allows multiplexed branched chain DNA-based detection of up to four mRNA transcripts (three were detected simultaneously in this study) together with antibody-based protein detection. As more branched DNA cascades are designed the number of transcripts that can be detected simultaneously will be limited only by the number of fluorometrically separable fluorophores available (currently 15).

In this study, SCRF was used for visualization of regulatory interactions in various subsets of mouse bone marrow. An early decision point in hematopoietic lineage progression is thought to rely on two self-activating and mutually inhibiting transcription factors, PU.1 and GATA1 (Graf, T. and T. Enver, Forcing cells to change lineages. Nature, 2009. 462(7273): p. 587-94). GATA1 establishes the identity of erythroid lineage. GATA1 expression is especially prominent in megakaryocyte-erythroid progenitor cells (MEPs), whereas high PU.1 levels are associated with differentiation along the myelomonocytic lineage. CMPs are most proximally defined as the GATA1$^+$Flt3$^-$CD34$^+$ subset of LSKs and further downstream as CD34$^+$FcγR$^-$ cells of the LK population. CMPs are able to differentiate both along erythroid and monocytic lineages. The bi-potency of CMP has been attributed to so-called "multilineage priming" state whereby the founder cells are able to co-express otherwise mutually exclusive lineage specific genes (Miyamoto, T., et al. (2002) Developmental cell, 3(1): p. 137-147; Miyamoto, T. et al. (2005) International journal of hematology, 81(5): p. 361-367). While GATA1 transcript levels were not tested in single cell co-expression experiments around 30% of CMP were shown to express GATA1 protein (Arinobu, Y., et al (2007) Cell stem cell, 1(4): p. 416-427). Yet our data indicated that none of the CD34$^+$ LK cells (a subset that contains the classically defined CMPs) express the GATA1 transcript. This observation demonstrates that the "multilineage primed" state exists due to asynchrony between the protein and transcript levels. Specifically in the case of CMPs, which originate from GATA1$^{high}$ cells of the LSK compartment, the downstream "primed" state corresponds to cells with induced CD34 expression that retain sufficient GATA1 protein for activity, but lack detectable GATA1 transcripts due to inhibition of GATA1 transcription and activation of CD34 expression by elevated levels of PU.1.

Mathematical modeling suggested that the behavior of PU.1-GATA1 system is analogous to that of a bi-stable switch, with addition of an extra-stable state characterized by intermediate expression levels of both of the cross-inhibitory factors. It has been hypothesized that lineage specification corresponds to transition of such a system from a state with three attractors to a state with two attractors; in this state only mutually exclusive expression patterns would be observed (Huang, S., et al., (2007) Developmental biology, 305(2): p. 695-713). Our data confirms the "multilineage primed" state of mouse LSK population, where intermediate levels of cross-inhibitory PU.1 and GATA1 were observed. Contrary to expected cancellation of this state in committed progenitors, however, we observed a significant population of cells co-expressing PU.1 and GATA1 within the LK cells. Interestingly, this population was largely confined to GATA1-expressing MEP cells, rather than to cells expressing high levels of PU.1. Notably, on average, there were no more then two fluorescent spots corresponding to the PU.1 transcript in MEP cells co-expressing PU.1 and GATA1. In most of the cells, at least one of these spots was located inside the nuclear perimeter; the other was proximal to nuclear periphery, but nuclear localization of this signal was not definitive. Thus, the PU.1 locus is active in the majority of GATA1-positive MEP cells. Transcriptional repression of PU.1 by GATA1 relies on an interaction between PU.1 and GATA; this complex is unable to activate transcription (Nerlov, C., et al., (2000) Blood, April 15; 95(8):2543-51; Rekhtman, N. et al (1999) Genes Dev. un 1; 13(11):1398-411; Rekhtman, N. et al (2003) Molecular and Cellular Biology, 23(21): p. 7460). It is plausible that repression of either gene could depend on its constant expression at levels sufficient to serve as a foundation for formation of repressive complexes. In such a scenario, minimal co-expression of GATA1 and PU.1 should be observed in cells with high PU.1 or high GATA1. However, our demonstration of the complete lack of GATA1 expression in PU.1$^{high}$ cells demonstrates the existence of specialized mechanisms of GATA1 repression in PU.1$^{high}$ LMPPs.

Use of RNA in situ hybridization has been instrumental in establishing the "transcriptional bursting" model which has been recently widely used to describe the heterogeneity (often manifested as bi-modality) in gene expression observed in homogeneous cell populations (Munsky, B., G. et al. (2012). Science 336(6078): p. 183-187). The bursting paradigm accommodates both expressional heterogeneity due to variable presence of the upstream activator (extrinsic bursting), and heterogeneity occurring even in the constant presence of the activator (intrinsic bursting, so far best explained by oscillatory behavior of the locus's permissive state (Lionnet, T. and R. H. Singer, (2012) EMBO reports, 13(4): p. 313-321). Most studies focusing on transcriptional bursting have been performed by manual transcript counting in individual cells. We used SCRF cytometry to examine the heterogeneous production of IFNα by activated plasmacytoid dendritic cells (pDC), which has been so far described at the protein level. Previous studies indicate that transcription of type I IFN genes is crucially dependent on the presence of the transcription factor IRF7 (Honda, K., A. et al. (2006) Immunity, 25(3): p. 349-360). It was shown that the expression of IFNb (Zawatzky, R., E. (1985) Proceedings Of The National Academy Of Sciences Of The United States Of America, 82(4): p. 1136-40) and of other cytokines (Hollander, G. A., et al. (1999) Seminars in immunology, 11(5): p. 357-67; Guo, L., et al. (2004) Immunity, 20(2): p. 193-203) is highly stochastic. A recent report from Maniatis' group (Zhao, M., et al., (2012) PLoS biology, 10(1): p. e1001249) suggests that variability in IRF7 levels is one of the main reasons for the heterogeneous response in activated cell cultures homogeneously capable of cytokine production. We sought to explore IFNα production in pDCs and its dependence on IRF7. Surprisingly, only a minor subset of the population was capable of IFNα RNA synthesis despite high induction of IRF7 expression in all pDC. This observation shows that additional mechanisms, not mediated by IRF7, account for the heterogeneity in IFN expression by pDCs. One such mechanism is an oscillatory behavior of IFNα locus.

In this study the procedure developed for analysis of mRNA by flow cytometry was used to characterize regulatory gene expression in developing hematopoietic system and to analyze stochastic behavior of a particular locus upon activation. As demonstrated, SCRF cytometry can be used for the detection of rare mRNAs, and finds application in analysis of clinically important cell subsets, such as virus-infected cells (HIV diagnostics) or circulating tumor cells (cancer diagnostics). SCRF cytometry can also be used for evaluation of bioactive transcripts that are not translated into proteins, such as of long non-coding RNAs. Wide dynamic range and strong correlation between the average number of molecules and the relative MFI as detected by flow cytometry observed in our study shows that SCRF can be successfully employed for single-cell based transcript counting in a multiplexed settings. These types of data are currently obtained by manual transcript counting in a limited number of cells. SCRF cytometry can also be used for analyses in which antibodies necessary for protein expression studies are not available.

Example 2—Detection of miRNA (Micro RNA)

Methods

A methanol based buffer was used for permeabilization and fixation (the same buffer used for mRNA (see Example 1) can also be used for miRNA). miRNA probe set design was similar to that used for the QG ViewRNA Cell assay (Affymetrix—Panomics). Reagents were used as in Example 1, including a methanol treatment, with the following details: one hour fixation with 4% PFA (as opposed to 10-20 minutes); one hour post-fixation (as opposed to 20 minutes); sequential pre-amplification and amplification hybridization was performed for 1.5 hours at 40° C.; the labeled probe (LP) was conjugated with alkaline phosphatase (AP) and hybridization was for one hour at 40° C.; Fast Red reagent (a substrate for AP) was used for signal detection; the Fast Red incubation was for 30-45 min at 40° C.; and cells were fixed with 4% formaldehyde for 10 min at room temperature after Fast Red incubation.

Results

Figure 14:
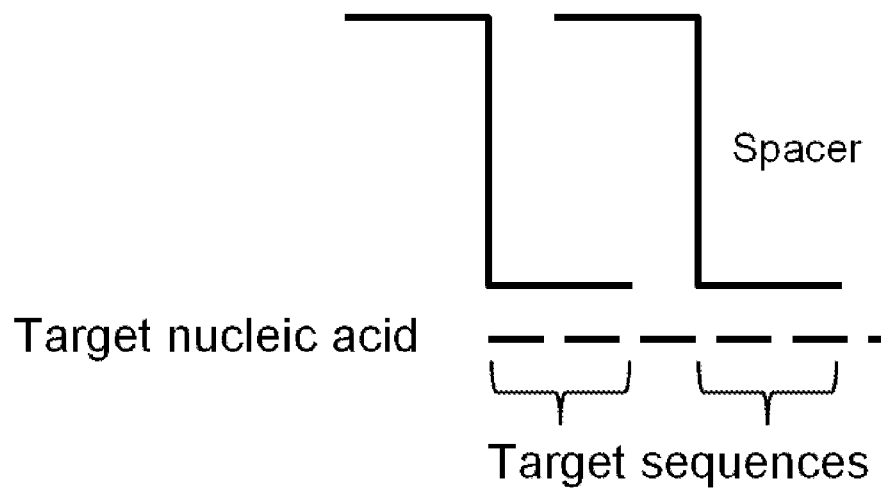
FIG. 14 presents a schematic diagram depicting one embodiment of the hybridization steps to detect a target nucleic acid (e.g., a miRNA).

A subject flow cytometry based analysis was performed to detect mature miRNA in single cells using branched DNA signal amplification (FIG. 14). Multiple different miRNAs (Let7a, miR223, miR15a, and miR155) were detected in human U937 cells (FIG. 15 and FIG. 16).

Figure 15:
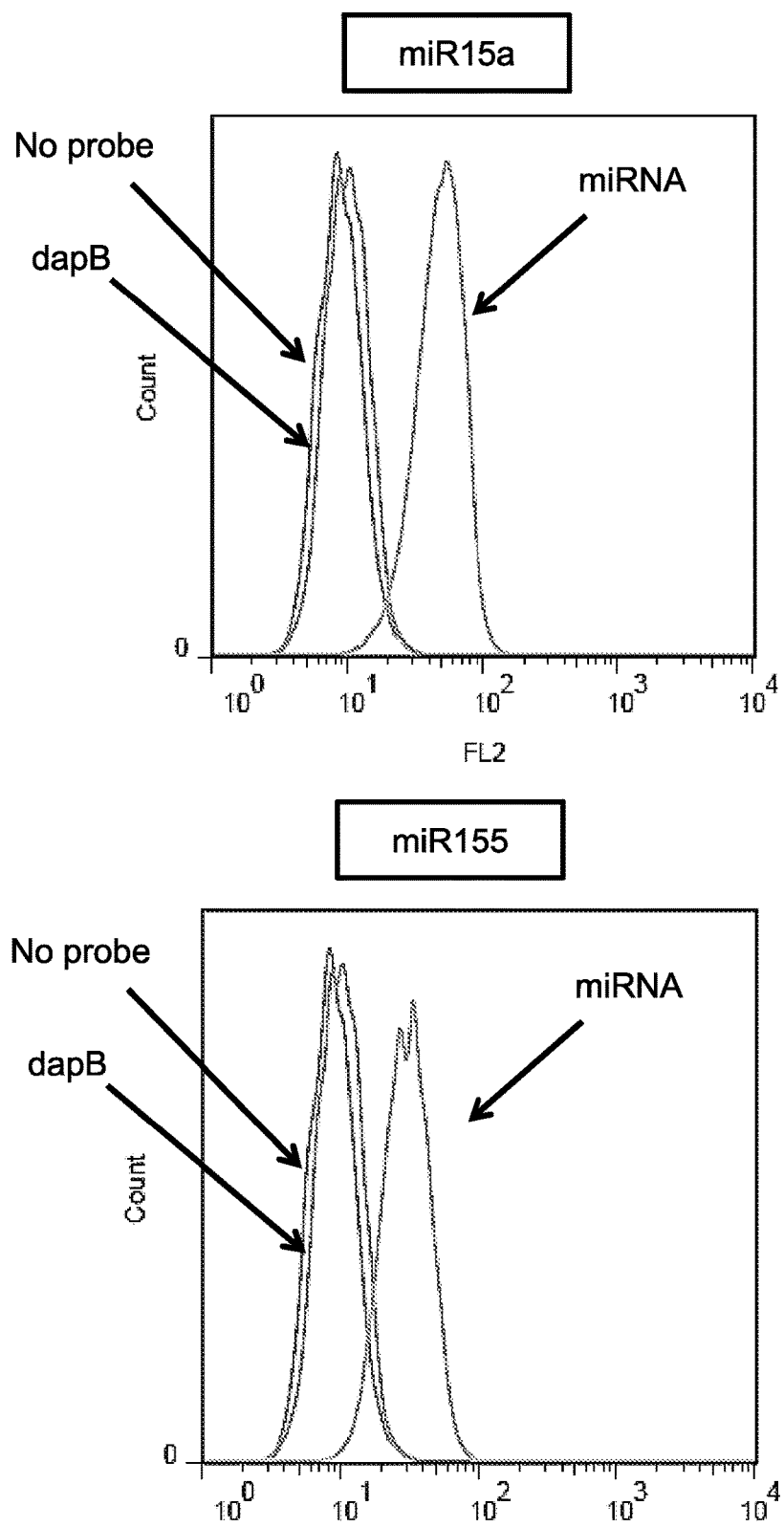
FIGS. 15A-B demonstrate successful detection of miRNAs in human U937 cells using a method according to an embodiment.

FIG. 15 demonstrates that the subject methods successfully detect miRNAs in human U937 cells. dapB (dihydrodipicolinate reductase) is a bacterial gene that is not present in human U937 cells and therefore serves as a negative control. (A) Let7a and miR223 were successfully detected using flow cytometry. (B) miR15a and miR155 were successfully detected using flow cytometry.

Figure 16:
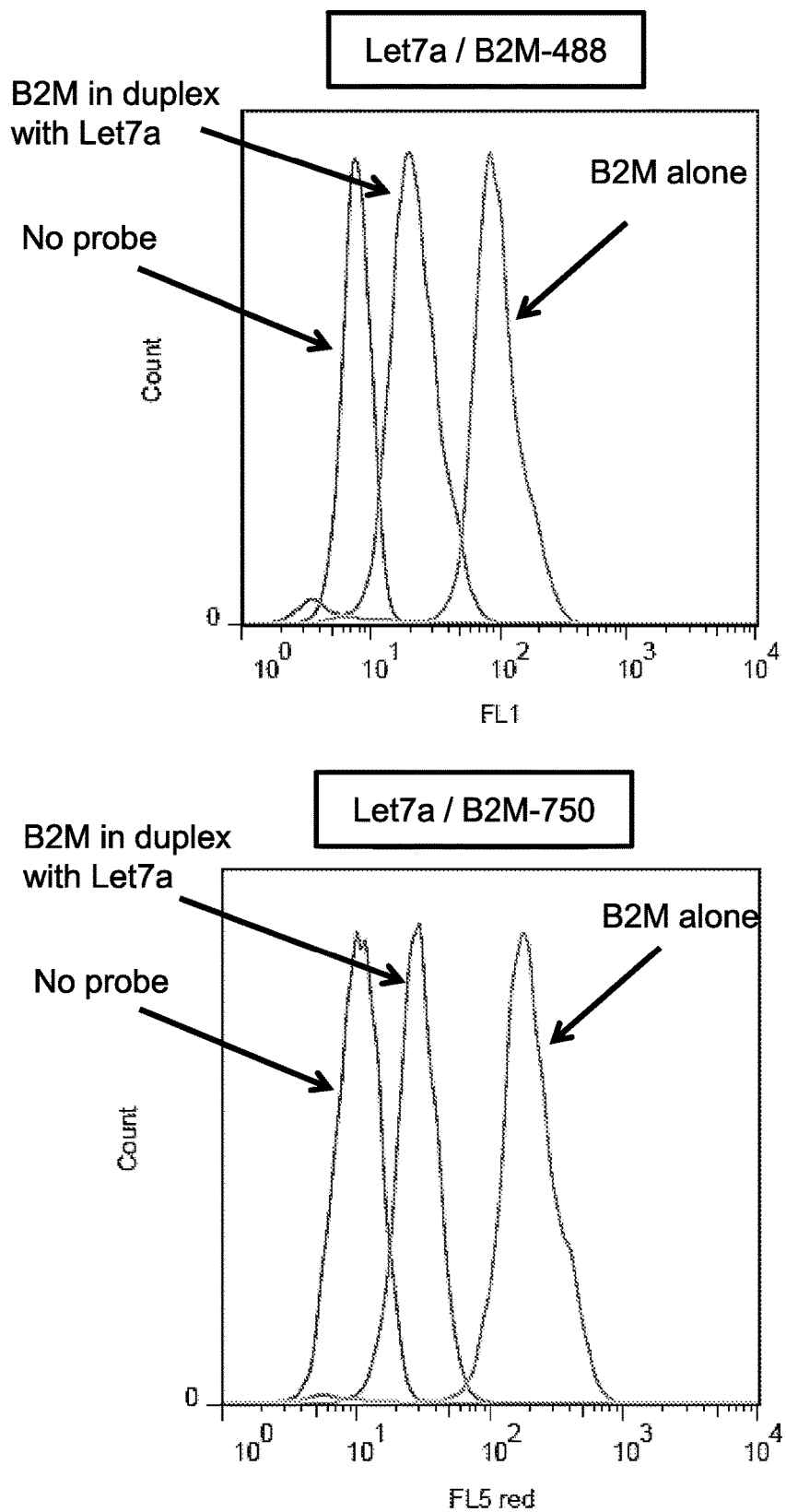
FIG. 16 demonstrates successful detection of miRNA and proteins simultaneously in the same cells using a method according to an embodiment.

FIG. 16 demonstrates simultaneous detection of a miRNA (Let7a) and a protein (beta-2 microglobulin; B2M) using branched DNA signal amplification (FIG. 14) and flow cytometry. In the top panel, B2M was conjugated with a label moiety and the detected signal was light emitted at a peak wavelength of 488 nm. In the bottom panel, B2M was conjugated with a label moiety and the detected signal was light emitted at a peak wavelength of 750 nm signal. The Let7a signal was similar when only Let7a was detected (single plex) or when Let7a was detected in combination (duplex) with B2M. The B2M signal was reduced when detected in duplex (in combination with Let7a) compared to when it was detected in single plex. The reduction in B2M signal was likely due to the long (45 minute) Fast Red incubation. Regardless, B2M signal was clearly detected in duplex with Let7a detection.

In summary, two experiments in U937 cells were performed and Let7a detection was reproduced consistently in both experiments (FIG. 15 and FIG. 16). miRNA targets successfully detected in U937 cells include Let7a and miR223 (FIG. 15A); and miR155 and miR15a (FIG. 15B). Moreover, as demonstrated here via the detection of mature miRNA targets, the subject methods can be used to detect target nucleic acids with short target sequences. Thus, the subject methods are also useful for the detection other target nucleic acids with short target sequences (e.g., fusion gene transcripts, splice variants, etc.). In addition, it is possible to simultaneously detect multiple different nucleic acid targets (e.g., mRNA, miRNA, fusion gene transcripts, splice variant transcripts, etc.) and proteins in a cell (FIG. 16) using the subject methods (e.g., using branched nucleic acid signal amplification and flow cytometry).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of assaying a cellular sample that comprises one or more cells in suspension for the presence of a target nucleic acid, the method comprising:
   contacting the cellular sample with, in order: (i) a fixation reagent; (ii) a permeabilization reagent; (iii) an aqueous fixative comprising one or more fixation reagents selected from the group consisting of: a cross-linking fixative, a precipitating fixative, an oxidizing fixative, and a mercurial fixative; and (iv) a nucleic acid detection agent comprising a signal producing system that comprises a branched nucleic acid signal amplification component, to produce a suspended hydrated/fixed detection agent-contacted cellular sample; and
   measuring a signal produced by the signal producing system to evaluate the suspended hydrated/fixed detection agent-contacted cellular sample for the presence of the target nucleic acid.

2. The method according to claim 1, wherein the target nucleic acid is a ribonucleic acid (RNA).

3. The method according to claim 2, wherein the RNA is a microRNA, a fusion gene transcript, or a splice variant.

4. The method according to claim 1, wherein the method further comprises contacting the cellular sample with a protein detection reagent.

5. The method according to claim 4, wherein the protein detection reagent comprises a labeled binding member that specifically binds to a target protein.

6. The method according to claim 5, wherein the labeled binding member comprises an antibody or binding fragment thereof.

7. The method according to claim 6, wherein the label is a metal.

8. The method according to claim 6, wherein the measuring comprises measuring the amount of label using mass cytometry.

9. The method according to claim 1, wherein the signal producing system comprises a nucleic acid probe comprising a label that produces the signal.

10. The method according to claim 9, wherein the label is a metal.

11. The method according to claim 10, wherein the measuring comprises mass cytometry.

12. The method according to claim 1, wherein the measuring comprises flow cytometry.

13. The method according to claim 1, wherein the method comprises, after contacting the cellular sample with the aqueous fixative, storing the cellular sample for a period of time prior to the measuring step.

14. The method according to claim 13, wherein the storing is in an aqueous buffer comprising a nuclease inhibitor.

15. The method according to claim 14, wherein the storing is at a temperature below 0° C.

16. The method according to claim 1, comprising contacting the cellular sample with a stimulating agent prior to contact with the fixation reagent.

17. The method according to claim 1, wherein the method further comprises obtaining the cellular sample.

18. The method according to claim 1, wherein the cellular sample is a human cellular sample.

19. The method according to claim 18, wherein the method further comprises employing a result of the evaluating step to diagnose a state of the human.

20. The method according to claim 18, wherein the state is a disease state.

21. The method according to claim 20, wherein the disease state is a cellular proliferative disease state.

22. The method according to claim 1, further comprising contacting the cellular sample with a nuclease inhibitor after step (iii).

23. The method according to claim 1, wherein the permeabilization reagent comprises methanol.

24. The method according to claim 1, wherein the aqueous fixative comprises an aldehyde fixative.

25. The method according to claim 1, wherein the aqueous fixative comprises at least one of: formaldehyde and glutaraldehyde.

26. A method comprising:
   contacting a cellular sample that comprises one or more cells in suspension with, in order: (i) a fixation reagent; (ii) a permeabilization reagent; (iii) an aqueous fixative comprising one or more fixation reagents selected from the group consisting of: a cross-linking fixative, a precipitating fixative, an oxidizing fixative, and a mercurial fixative;
   to produce a hydrated/fixed suspended cellular sample.

27. The method according to claim 26, wherein the method further comprises contacting the cellular sample with a protein detection reagent.

28. The method according to claim 27, wherein the protein detection reagent comprises a labeled binding member that specifically binds to a target protein.

29. The method according to claim 28, wherein the labeled binding member comprises an antibody or binding fragment thereof.

30. The method according to claim 26, wherein the method further comprises contacting the cellular sample with a stimulating agent.

31. The method according to claim 26, wherein the cellular sample is a human cellular sample.

32. The method according to claim 26, further comprising contacting the cellular sample with a nuclease inhibitor after step (iii).

33. The method according to claim 26, wherein the permeabilization reagent comprises methanol.

34. The method according to claim 26, wherein the aqueous fixative comprises an aldehyde fixative.

35. The method according to claim 26, wherein the aqueous fixative comprises at least one of: formaldehyde and glutaraldehyde.

36. The method according to claim 26, wherein the permeabilization reagent comprises methanol.

37. A method of assaying a cellular sample that comprises one or more cells in suspension for the presence of a target nucleic acid, the method comprising:

contacting the cellular sample with, in order: (i) a first aqueous fixative; (ii) a permeabilization reagent; (iii) a second aqueous fixative comprising one or more fixation reagents selected from the group consisting of: a cross-linking fixative, a precipitating fixative, an oxidizing fixative, and a mercurial fixative; and (iv) a nucleic acid detection agent comprising a signal producing system that comprises a branched nucleic acid, to produce a suspended hydrated/fixed detection agent-contacted cellular sample; and measuring a signal produced by the signal producing system to evaluate the suspended hydrated/fixed detection agent-contacted cellular sample for the presence of the target RNA, wherein the measuring comprises flow cytometry.

38. The method according to claim 37, wherein the first and/or second aqueous fixative comprises an aldehyde fixative.

39. The method according to claim 37, wherein the first and/or second aqueous fixative comprises at least one of: formaldehyde and glutaraldehyde.

40. The method according to claim 37, further comprising contacting the cellular sample with a nuclease inhibitor after step (iii).

41. The method according to claim 37, wherein the permeabilization reagent comprises methanol.

42. The method according to claim 1, wherein the cross-linking fixative is an imidoester or a N-Hydroxysuccinimide (NHS) ester.

43. The method according to claim 26, w wherein the cross-linking fixative is an imidoester or a N-Hydroxysuccinimide (NHS) ester.

44. The method according to claim 37, wherein the cross-linking fixative is an imidoester or a N-Hydroxysuccinimide (NHS) ester.

45. The method according to claim 1, wherein the precipitating fixative is an alcohol, acetic acid, or acetone.

46. The method according to claim 26, wherein the precipitating fixative is an alcohol, acetic acid, or acetone.

47. The method according to claim 37, wherein the precipitating fixative is an alcohol, acetic acid, or acetone.

* * * * *